United States Patent
Lively et al.

(10) Patent No.: US 7,067,516 B2
(45) Date of Patent: Jun. 27, 2006

(54) SERINE PROTEASE INHIBITORS

(75) Inventors: Sarah Elizabeth Lively, Congleton (GB); Martin James Harrison, Manchester (GB); Neil Jason Naylor, Macclesfield (GB); Christopher Neil Farthing, Macclesfield (GB); Bohdan Waszkowycz, Wilmslow (GB)

(73) Assignee: Tularik Limited, London (GB)

( * ) Notice: Subject to any disclaimer, the term of this patent is extended or adjusted under 35 U.S.C. 154(b) by 317 days.

(21) Appl. No.: 10/432,365

(22) PCT Filed: Dec. 12, 2001

(86) PCT No.: PCT/GB01/05526

§ 371 (c)(1),
(2), (4) Date: Jun. 2, 2003

(87) PCT Pub. No.: WO02/47762

PCT Pub. Date: Jun. 20, 2002

(65) Prior Publication Data

US 2004/0116439 A1    Jun. 17, 2004

(30) Foreign Application Priority Data

Dec. 13, 2000 (GB) ................... PCT/GB00/04764
Jun. 12, 2001 (GB) ................... 0114185.2

(51) Int. Cl.
| | |
|---|---|
| A61K 31/381 | (2006.01) |
| A61K 31/428 | (2006.01) |
| C07D 277/30 | (2006.01) |
| C07D 277/82 | (2006.01) |
| C07D 333/68 | (2006.01) |
| C07D 401/12 | (2006.01) |
| C07D 417/12 | (2006.01) |

(52) U.S. Cl. ............... 514/233.5; 514/301; 514/338; 514/342; 514/366; 514/371; 514/443; 544/145; 546/114; 546/270.1; 546/270.7; 548/163; 548/195

(58) Field of Classification Search ............ 544/145; 546/114, 270.1, 270.7; 548/163, 195; 549/48, 549/57; 514/233.5, 301, 338, 342, 366, 371, 514/443

See application file for complete search history.

(56) References Cited

U.S. PATENT DOCUMENTS 6,262,069 B1  7/2001  Liebeschuetz et al.
6,420,438 B1  7/2002  Liebeschuetz et al.

FOREIGN PATENT DOCUMENTS

| WO | WO98/47876 | 10/1998 |
|---|---|---|
| WO | WO99/11657 | 3/1999 |
| WO | WO99/11658 | 3/1999 |
| WO | WO99/55661 | 11/1999 |
| WO | WO00/76970 | 12/2000 |
| WO | WO00/76971 | 12/2000 |
| WO | WO00/77027 | 12/2000 |
| WO | WO01/44226 | 6/2001 |
| WO | WO01/96305 | 12/2001 |

OTHER PUBLICATIONS

Moses et al., Chemical Abstracts, 62:473c-e, 1965.*
Dorman et al., Chemical Abstracts, 126:282631, 1997.*
Mankad et al., Chemical Abstracts, 60:2919d-h, 1964.*
Khalaj et al., Chemical Abstracts, 129:272882, 1998.*
Golub et al., Science, 286, 1999, 531-537.*
Cairns, Pulmonary Pharmacology & Therapeutics, 18(1), Feb. 2005, 55-66, abstract.*
Costanzo et al., J. Med. Chem., 46, 3865-3876, 2003.*
Lee et al., Arterioscler. Thromb. Vasc. Biol., 2002, 22, 2086-2091.*
Rice et al., Curr. Pharm. Des., Oct. 1998, 4(5), 381-396, abstract.*
Dorman, Douglas E., et al., J. Pharm. Sci. (1997), 86(5), 540-549.
Moses et al; Chemical Abstracts, vol. 62, No. 1, 1965, Abstract No. 473c.
Al-Obaid, A.M., et al., Pharmazie (1998), 53(1), 24-28.

* cited by examiner

*Primary Examiner*—Fiona T. Powers
(74) *Attorney, Agent, or Firm*—Martin A. Hay

(57) ABSTRACT

Compounds of formula (I)

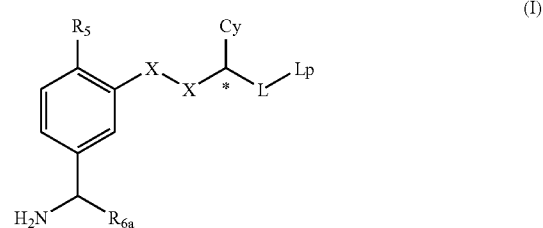

where $R_5$, $R_{6a}$, each X, L, Cy and Lp are as defined in the specification, are tryptase inhibitors useful as antiinflammatory agents.

41 Claims, No Drawings

SERINE PROTEASE INHIBITORS

This invention relates to compounds which are inhibitors of the serine protease, tryptase, to pharmaceutical compositions thereof and to their use in the treatment of the human or animal body. More particularly it relates to compounds for use in the treatment of mast cell mediated diseases such as asthma and other allergic and inflammatory conditions, to pharmaceutical compositions thereof and to their use in the treatment of the human or animal body.

Asthma, the most prevalent of all mast cell mediated conditions affects about 5% of the population in industrialised countries and there is evidence that its incidence and severity are on the increase. Furthermore, the incidence of childhood asthma is rising and there are suggestions of a link between environmental pollutants and the onset of the disease.

Initially, it was believed that bronchoconstriction, i.e. the narrowing of the airways in the lungs, was the major feature of asthma. However, it is now recognised that inflammation in the lungs is an integral part of the development of the disease.

The inhalation of an allergen by an asthmatic generates a strong immune system response which triggers release of various inflammatory mediators, including histamine and leukotrienes from inflammatory cells. These increase the permeability of the blood vessel walls, attract inflammatory cells into the tissues and contract the smooth muscle around the airways. As a result, fluid leaks from the blood and the tissues swell, further narrowing the airways. The inflammatory cells cause damage to the epithelial cells lining the airways exposing nerve endings which stimulates secretion of mucous as well as augmenting the inflammation by causing the release of neurokinins.

Thus asthma is a complex disease frequently characterised by progressive developments of hyper-responsiveness of the trachea and bronchi as a result of chronic inflammation reactions which irritate the epithelium lining the airway and cause pathological thickening of the underlying tissues.

Leukocytes and mast cells are present in the epithelium and smooth muscle tissue of the bronchi where they are activated initially by binding of specific inhaled antigens to IgE receptors. Activated mast cells release a number of preformed or primary chemical mediators of the inflammatory response in asthma as well as enzymes. Moreover, secondary mediators of inflammation are generated by enzymatic reactions of activated mast cells and a number of large molecules are released by degranulation of mast cells.

It has therefore been proposed that chemical release from mast cells probably accounts for the early bronchiolar constriction response that occurs in susceptible individuals after exposure to airborne allergens. The early asthmatic reaction is maximal at around 15 minutes after allergen exposure, recovery occurring over the ensuing 1 to 2 hours. In approximately 30% of individuals, the early asthmatic reaction is followed by a further decline in respiratory function which normally begins within a few hours and is maximal between 6 and 12 hours after exposure. This late asthmatic reaction is accompanied by a marked increase in the number of inflammatory cells infiltrating bronchiolar smooth muscle and epithelial tissues, and spilling into the airways. These cells are attracted to the site by release of mast cell derived chemotactic agents.

The most straightforward way of dealing with an asthma attack is with a bronchodilator drug which causes airways to expand. The most effective bronchodilators are the β-adrenergic agonists which mimic the actions of adrenalin. These are widely used and are simply administered to the lungs by inhalers. However, bronchoconstrictor drugs are primarily of use in short term symptomatic relief, and do not prevent asthma attacks nor deterioration of lung function over the long term.

Anti-inflammatory drugs such as cromoglycate and the corticosteroids are also widely used in asthma therapy. Cromoglycate has anti-inflammatory activity and has been found to be extremely safe. Although such cromolyns have minimal side effects and are currently preferred for initial preventive therapy in children, it is well known that they are of limited efficacy.

The use of corticosteroids in asthma therapy was a major advance since they are very effective anti-inflammatory agents, however, steroids are very powerful, broad spectrum anti-inflammatory agents and their potency and non-specificity means that they are seriously limited by adverse side effects. Localising steroid treatment to the lungs using inhaler technology has reduced side effects but the reduced systemic exposure following inhalation still results in some undesirable effects. Hence, there is a reluctance to use steroids early in the course of the disease.

There therefore still remains a need for an alternative asthma therapy which is a safe, effective, anti-inflammatory or immunomodulatory agent which can be taken to treat chronic asthma.

Tryptase is the major secretory protease of human mast cells and is proposed to be involved in neuropeptide processing and tissue inflammation. Tryptase is one of a large number of serine protease enzymes which play a central role in the regulation of a wide variety of physiological processes including coagulation, fibrinolysis, fertilization, development, malignancy, neuromuscular patterning and inflammation. Although a large number of serine proteases have been widely investigated, tryptase still remains relatively unexplored.

Mature human tryptase is a glycosylated, heparin-associated tetramer of catalytically active subunits. Its amino-acid structure appears to have no close counterpart among the other serine proteases which have been characterised. Tryptase is stored in mast cell secretory granules and after mast cell activation, human tryptase can be measured readily in a variety of biological fluids. For example, after anaphylaxis, tryptase appears in the blood stream where it is readily detectable for several hours. Tryptase also appears in samples of nasal and lung lavage fluid from atopic subjects challenged with specific antigen. Tryptase has been implicated in a variety of biological processes where activation and degranulation of mast cells occur. Accordingly, mast cell tryptase inhibition may be of great value in the prophylaxis and treatment of a variety of mast cell mediated conditions. Mast cells can degranulate by both IgE-dependent and independent mechanisms thereby implicating tryptase in both atopic and non-atopic inflammatory conditions. Tryptase can activate proteases such as pro-urokinase and pro-MMP3 (pro-matrix metalloprotease 3, pro-stromelysin), thereby indicating a pathological role in tissue inflammation and remodelling. Furthermore, the recent evidence that tryptase can activate certain G-protein coupled receptors (eg PAR2) and induce neurogenic inflammation points to a broader physiological role, for example in modulating pain mechanisms. Given tryptase's multiple mechanisms of action, it has been proposed that tryptase inhibitors may be beneficial in a broad range of diseases. These include conditions such as: asthma (specifically influencing the inflammatory component, the underlying hyperreactivity, and the chronic fibrotic damage due to smooth muscle thickening); chronic obstructive pulmonary disease (COPD) and pulmonary fibrotic diseases; rhinitis; psoriasis; urticaria; dermatitis; arthritis; Crohn's disease; colitis; angiogenesis; atherosclerosis; multiple sclerosis; interstitial cystitis; migraine headache; neurogenic inflammation and pain mechanisms; wound healing; cirrhosis of the liver; Kimura's disease; pre-eclampsia; bleeding problems associated with menstruation and the menopause; cancer (particularly melanoma and tumour metastasis); pancreatitis; and certain viral infections (Yong, Exp. Toxic Pathol, 1997, 49, 409; Steinhoff et al., Nat. Med., 2000, 6, 151; Downing and Miyan, Immunol. Today, 2000, 21, 281; Tetlow and Wooley, Ann. Rheum. Dis., 1995, 54, 549; Jeziorska, Salamonsen and Wooley, Biol. Reprod., 1995, 53, 312; Brain, Nat. Med., 2000, 6, 134; Olness et al., Headache, 1999, 39, 101.) The underlying principle is that a tryptase inhibitor should have utility where mast cells have being induced to degranulate by whatever mechanism, including anaphylactic reactions due to exogenous substances, e.g. morphine-induced bronchoconstriction (Bowman and Rand, Textbook of Pharmacology, $2^{nd}$ edt., 1980.)

In WO96/09297, WO95/32945, WO94/20527 and U.S. Pat. No. 5,525,623 a variety of peptide based compounds are suggested as potential inhibitors of the mast cell protease tryptase. In WO95/03333 a tryptase inhibitor is provided by a polypeptide obtainable from the leech *hirudo medicinalis*. In WO96/08275 secretory leukocyte protease inhibitor (SLPI) and active fragments thereof have been found to inhibit the proteolytic activity of tryptase. In WO99/55661 certain 4-aminomethylbenzoic ester derivatives are proposed as potential tryptase inhibitors.

We have now found that certain aromatic compounds carrying lipophilic side chains are particularly effective as inhibitors of the serine protease, tryptase. Certain of these compounds have further been found to have good oral bioavailability.

It is envisaged that the compounds of the invention will be useful not only in the treatment and prophylaxis of asthma but also of other allergic and inflammatory conditions mediated by tryptase such as allergic rhinitis, skin conditions such as eczema, psoriasis, atopic dermatitis and urticaria, rheumatoid arthritis, conjunctivitis, inflammatory bowel disease, neurogenic inflammation, atherosclerosis and cancer.

Thus viewed from one aspect the invention provides a tryptase inhibitor compound of formula (I)

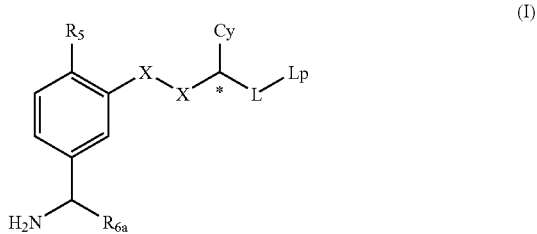

(I)

where:

$R_5$ represents amino, hydroxy, aminomethyl, hydroxymethyl or hydrogen;

$R_{6a}$ represents hydrogen or methyl;

X—X is selected from —CH=CH—, —CONR$_{1a}$—, —NH—CO—, —NR$_{1a}$—CH$_2$—, —CH$_2$—NR$_{1a}$—, —CH$_2$O—, —OCH$_2$—, —COO—, —OC=O— and —CH$_2$CH$_2$—;

$R_{1a}$ represents hydrogen, (1–6C)alkyl or phenyl(1–6C)alkyl;

L is CO or CONR$_{1d}$(CH$_2$)$_m$ in which m is 0 or 1 and $R_{1d}$ is hydrogen, (1–6C)alkyl or phenyl(1–6C)alkyl;

Cy represents cycloalkyl, piperidinyl, 3,4-methylenedioxyphenyl, furyl, thienyl, imidazolyl, oxazolyl, thiazolyl, pyridyl, pyrimidinyl, pyrazinyl, naphthyl, indolyl, indanyl, 3,4-dihydrobenzofuryl, benzofuryl or benzo[b]thienyl group, optionally substituted by $R_{3a}$ or $R_{3i}X_i$ in which $X_i$ is a bond, O, NH, CH$_2$, CO, CONH, NHCO, CO$_2$, NHSO$_2$ or SO$_2$NH and $R_{3i}$ is phenyl or pyridyl optionally substituted by $R_{3a}$;

each $R_{3a}$ independently is hydrogen, hydroxyl, (1–6C) alkoxy, (1–6C) alkyl, (2–6C)alkenyl, (2–6C)alkynyl, (1–6C) alkanoyl, (1–6C) alkylaminoalkyl, hydroxy(1–6C)alkyl, carboxy, (1–6C) alkoxyalkyl, (1–6C) alkoxycarbonyl, (1–6C) alkylaminocarbonyl, amino(1–6C)alkyl, CONH$_2$, CH$_2$CONH$_2$, aminoacetyl, (1–6C)alkanoylamino, hydroxy (1–6C)alkanoylamino, amino(1–6C)alkanoylamino, (1–6C) alkylamino(1–6C)alkanoylamino, di(1–6C)alkylamino (1–6C)alkanoylamino, (1–6C) alkoxycarbonylamino, amino, halo, cyano, nitro, thiol, (1–6C) alkylthio, (1–6C) alkylsulphonyl, (1–6C) alkylsulphenyl, imidazolyl, hydrazido, (1–6C)alkylimidazolyl, (1–6C) alkylsulphonamido, (1–6C) alkylaminosulphonyl, aminosulphonyl, (1–6C) haloalkoxy, or (1–6C) haloalkyl; and Lp is a lipophilic group;

or a physiologically tolerable salt thereof, e.g. a halide, phosphate or sulphate salt or a salt with ammonium or an organic amine such as ethylamine or meglumine.

Compounds of formula I have surprisingly been found to be particularly effective as inhibitors of tryptase and to show a surprising selectivity for tryptase over other serine proteases.

In the compounds of the invention, $R_5$ preferably represents amino or hydrogen, more preferably hydrogen.

$R_{6a}$ preferably represents hydrogen.

In the compounds of the invention, the alpha atom (*) preferably has the conformation that would result from construction from a D-α-aminoacid NH$_2$—CH(Cy)-COOH where the NH$_2$ represents part of X—X.

In the compounds of the invention, unless otherwise indicated, aryl groups preferably contain 5 to 10 ring atoms optionally including 1, 2 or 3 heteroatoms selected from O, N and S; alkyl, alkenyl or alkynyl groups or alkylene moieties preferably contain up to 6 carbons, e.g. $C_{1-6}$ or $C_{1-3}$; cyclic groups preferably have ring sizes of 3 to 8 atoms; and fused multicyclic groups preferably contain 8 to 16 ring atoms.

$R_{1a}$ is preferably hydrogen.

X—X may, for example, be selected from —CH=CH—, —CONR$_{1a}$—, —NH—CO—, —NH—CH$_2$—, —CH$_2$—NH—, —CH$_2$O—, —OCH$_2$—, —COO—, —OC=O— and —CH$_2$CH$_2$—.

Preferably, the X moiety nearest to the alpha atom is an NH or O atom, most preferably an NH group. The X moiety alpha to the aromatic ring is preferably a carbon based group such as CH$_2$ or CO, preferably CO. Thus a particularly preferred linker X—X is —CONH—.

Examples of particular values for $R_{1d}$ are: hydrogen; for (1–6C)alkyl: methyl or ethyl; and for phenyl(1–6C)alkyl: benzyl or phenylethyl.

$R_{1d}$ is preferably hydrogen.

Examples of particular values for L are CO, CONH, CON(CH$_3$) and CONHCH$_2$, more preferably CO, CONH or CON(CH$_3$).

It will be appreciated by those skilled in the art that a diverse range of organic groups are lipophilic, and that it is therefore impractical to define with precision each and every structure that may be incorporated into a serine protease inhibitor according to the invention. Accordingly, it is being assumed that the addressee of this specification will not require an exhaustive computer listing of structures of lipophilic groups, but will instead make use of the structures of lipophilic groups disclosed in the specification, especially those exemplified; the test systems described herein for identifying tryptase inhibitors; and common general knowledge of the lipophilicity, synthesis and stability of organic compounds, to obtain novel inhibitor compounds of formula (I).

The lipophilic group may be, for example, an alkyl, alkenyl, carbocyclic or heterocyclic group, or a combination of two or more such groups linked by a spiro linkage or a single or double bond or by C=O, O, OCO, COO, S, SO, $SO_2$, $CONR_{1e}$, $NR_{1e}$—CO— or $NR_{1e}$ linkage (where $R_{1e}$ is as defined for $R_{1a}$), optionally substituted by one or more oxo or $R_3$ groups in which $R_3$ is an amino acid residue, N-(1–6C)alkylaminocarbonyl, N,N-di(1–6C)alkylaminocarbonyl, N-(1–6C)alkylamino(1–6C)alkanoyl, N-(1–6C)alkanoylamino(1–6C)alkanonyl, C-hydroxyamino(1–6C)alkanoyl, hydroxy(2–6C)alkanoylamino(1–6C)alkanoyl, di(1–6C)alkylaminosulfonyl, hydrogen, hydroxyl, (1–6C)alkoxy, (1–6C)alkanoyloxy, (1–6C) alkyl, (2–6C)alkenyl (2–6C)alkynyl, (3–6C)alkenyloxycarbonyl, (1–6C)alkanoyl, amino(1–6C)alkyl, amido ($CONH_2$), amino(1–6C)alkanoyl, aminocarbonyl(1–5C)alkanoyl, hydroxy(1–6C)alkyl, carboxy, hydroxy(1–6C)alkanoyl, (1–6C)alkoxy (1–6C)alkyl, (1–6C)alkoxycarbonyl(1–5C)alkyl, (1–6C) alkoxycarbonyl, (1–6C)alkanoylamino, amino, halo, cyano, nitro, thiol, (1–6C) alkylthio, (1–6C)alkylsulfonyl, (1–6C) alkylsulphenyl and hydrazido.

Preferably the lipophilic group is a carbocyclic or heterocyclic group, or a combination of a carbocyclic or heterocyclic group with one or more alkyl, alkenyl, carbocyclic or heterocyclic groups, linked by a spiro linkage or a single or double bond or by C=O, O, OCO, COO, S, SO, $SO_2$, $CONR_{1e}$, $NR_{1e}$—CO— or $NR_{1e}$ linkage (where $R_{1e}$ is as defined for $R_{1a}$), optionally substituted by one or more oxo or $R_3$ groups.

$R_{1e}$ is preferably a hydrogen atom.

When the lipophilic group comprises an alkyl group, this may be, for example, a (1–3C) alkyl group, such as methyl, ethyl or propyl. Preferably an alkyl group is unsubstituted.

When the lipophilic group comprises a carbocyclic group, this may be, for example, a non-aromatic or aromatic, mono or polycyclic hydrocarbon group containing up to 25, more preferably up to 10 carbon atoms. The carbocyclic group may thus be, for example, a cycloalkyl, polycycloalkyl, phenyl or naphthyl group, or a cycloalkyl group fused with a phenyl group.

Examples of particular values for a cycloalkyl group are (3–6C) cycloalkyl groups, such as cyclopentyl and cyclohexyl. A cycloalkyl group is preferably unsubstituted or substituted by one group $R_3$, preferably an amino or alkyl group.

Examples of particular values for a polycycloalkyl group are (6–10C) polycycloalkyl groups, such as bicycloalkyl, for example decalinyl or norbornyl. A polycycloalkyl group is preferably unsubstituted or substituted by one, two or three $R_3$ groups, for example alkyl such as methyl. An example of a polycycloalkyl group substituted by alkyl is isopinocampheyl.

A phenyl group is preferably unsubstituted or substituted by one or two $R_3$ groups.

A naphthyl group is preferably unsubstituted or substituted by one $R_3$ group.

Examples of a cycloalkyl or cycloalkenyl group fused with a phenyl group are indanyl and tetrahydronaphthyl. This group is preferably unsubstituted or substituted by oxo or one or two $R_3$ groups. Examples of groups substituted by oxo are 1-oxoindan-5-yl, 1-oxo-1,2,3,4-tetrahydronaphth-7-yl and 1-oxo-1,2,3,4-tetrahydro-naphth-6-yl.

When the lipophilic group comprises a heterocyclic group, this may be, for example, a non-aromatic or aromatic, mono or polycyclic group containing one or two oxygen, nitrogen or sulfur atoms in the ring system, and in total up to 25, more preferably up to 10 ring system atoms.

Examples of a heterocyclic group when it is a non-aromatic monocyclic group are azacycloalkyl groups, such as pyrrolidinyl and piperidinyl; azacycloalkenyl groups, such as pyrrolinyl; diazacycloalkyl groups, such as piperazinyl; oxacycloalkyl groups, such as tetrahydropyranyl; oxaazacycloalkyl groups, such as morpholino; and thiacycloalkyl groups, such as tetrahydrothiopyranyl. A non-aromatic monocyclic group preferably contains 5, 6 or 7 ring atoms and is preferably unsubstituted or substituted by one group $R_3$.

Examples of a heterocyclic group when it is a non-aromatic polycyclic group are bicyclic groups, such as azacycloalkyl fused with phenyl, for example dihydroindolyl, dihydroisoindolyl, tetrahydroquinolinyl and tetrahydroisoquinolinyl; azacycloalkyl fused with cycloalkyl, such as decahydroisoquinolinyl; and thienyl fused with cycloalkyl, such as tetrahydrobenzo[b]thienyl or 4H-cyclopenta(b)thienyl. Examples of thienyl fused with cycloalkyl are 4H-cyclohepta(b)thienyl and tetrahydro-4,7-methanobenzo(b)thiophenyl. Further examples of bicyclic groups are thienyl fused with a heterocycloalkyl group, such as 4,5-dihydro-5H-thieno[2,3-c]pyranyl, 4,5-dihydro-5H-thieno[2,3-c]thiopyranyl and 4,5,6,7-tetrahydrothieno[2,3-b]pyridinyl.

Examples of a heterocyclic group when it is an aromatic monocyclic group are furyl, pyrrolyl, thienyl, imidazolyl, thiazolyl, pyridyl, pyridazinyl, pyrimidinyl, pyrazinyl and triazinyl, preferably unsubstituted or substituted by one or two $R_3$ groups.

Examples of a heterocyclic group when it is an aromatic polycyclic group are bicyclic groups such as benzofuryl, quinolinyl, isoquinolinyl, benzothienyl, indolyl and benzothiazolyl.

Where Lp comprises a combination of at least two groups, it preferably comprises a combination of two or three such groups. The groups are preferably linked by a single bond, C=O, OCO, COO, O or $NR_{1e}$.

Examples of particular values for $R_3$ are: for an amino acid residue: N-acetylalaninoyl, serinoyl, threoninoyl, aspartoyl or glutamoyl;

for N-(1–6C)alkylaminocarbonyl: N-(1,3-dimethyl)butylamino-carbonyl;

for N,N-di(1–6C)alkylaminocarbonyl: N-methyl-N-ethylaminocarbonyl;

for N-(1–6C)alkylamino(1–6C)alkanoyl: N-methylacetyl; for N-(1–6C)alkanoylamino(1–6C)alkanonyl: 2-N-acetylaminoacetyl, 2-N-acetylaminopropanoyl or 2-N-(2-methylpropanoyl)aminoacetyl;

for C-hydroxyamino(1–6C)alkanoyl: 2-amino-3-hydroxypropanoyl or 2-amino-3-hydroxybutanoyl;

for hydroxy(2–6C)alkanoylamino(1–6C)alkanoyl: 2-hydroxyacetylaminoacetyl;

for di(1–6C)alkylaminosulfonyl: dimethylaminosulfonyl;

hydrogen;

hydroxyl;

for (1–6C)alkoxy: methoxy;

for (1–6C)alkanoyloxy: acetoxy;

for (1–6C) alkyl: methyl, ethyl, propyl, 2-propyl or 2,2-dimethylethyl;

for (2–6C)alkenyl: allyl;

for (2–6C)alkyl: propynyl;

for (3–6C)alkenyloxycarbonyl: allyloxycarbonyl;

for (1–6C)alkanoyl: acetyl, propionyl or isobutyryl;

for amino(1–6C)alkyl: aminomethyl;

amido ($CONH_2$);

for amino(1–6C)alkanoyl: aminoacetyl ($COCH_2NH_2$), aminopropionyl ($COCH_2CH_2NH_2$) or 2-aminopropionyl ($COCH(CH_3)NH_2$);

for aminocarbonyl(1–5C)alkanoyl: aminocarbonylacetyl;

for hydroxy(1–6C)alkyl: hydroxymethyl or 1-hydroxyethyl;
carboxy;
for hydroxy(1–6C)alkanoyl: 2-hydroxyacetyl or 2-hydroxypropanoyl;
for (1–6C)alkoxy(1–6C)alkyl: methoxymethyl;
for (1–6C)alkoxycarbonyl(1–5C)alkyl: methoxycarbonylmethyl;
for (1–6C)alkoxycarbonyl: methoxycarbonyl or ethoxycarbonyl;
for (1–6C)alkanoylamino: formylamino or acetylamino;
amino;
for halo: chloro;
cyano;
nitro;
thiol;
for (1–6C)alkylthio: methylthio;
for (1–6C)alkylsulfonyl: methylsulphonyl or ethylsulfonyl;
for (1–6C)alkylsulphenyl: methylsulphenyl; and
hydrazido.

Further examples of particular values for $R_3$ are:
for N-(1–6C)alkylaminocarbonyl: N-methylaminocarbonyl or N-isobutylaminocarbonyl; and
for N,N-di(1–6C)alkylaminocarbonyl: N,N-dimethylaminocarbonyl or N,N-diethylaminocarbonyl.

Most preferably, the lipophilic group is selected from

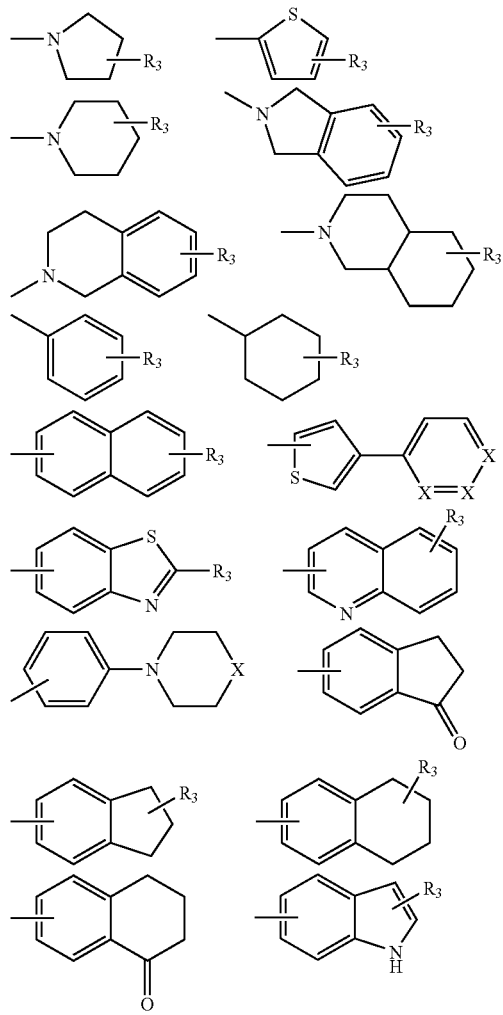

-continued

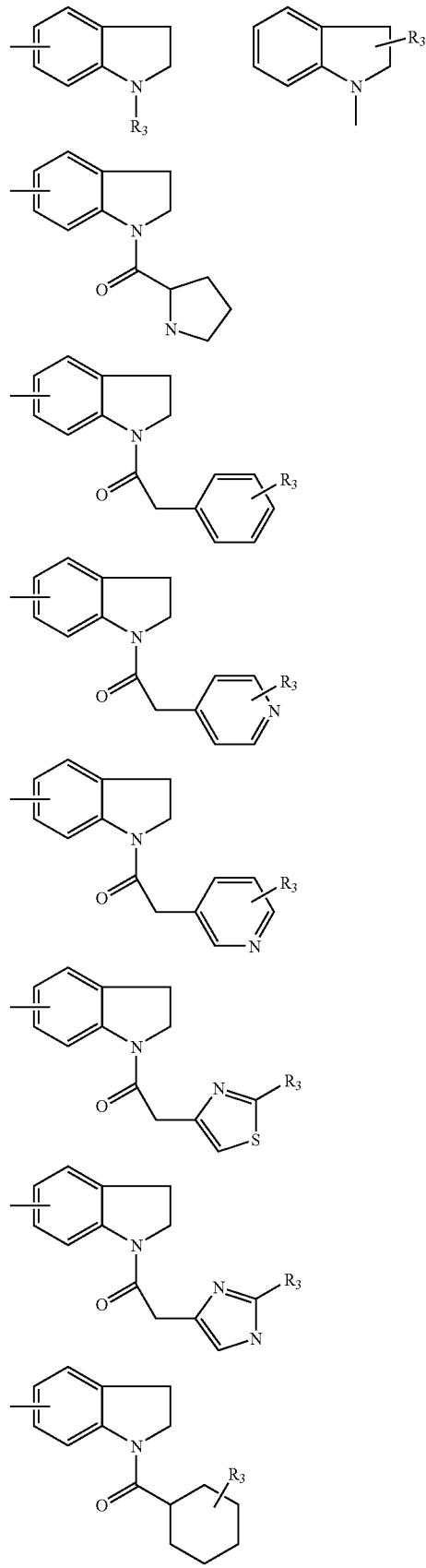

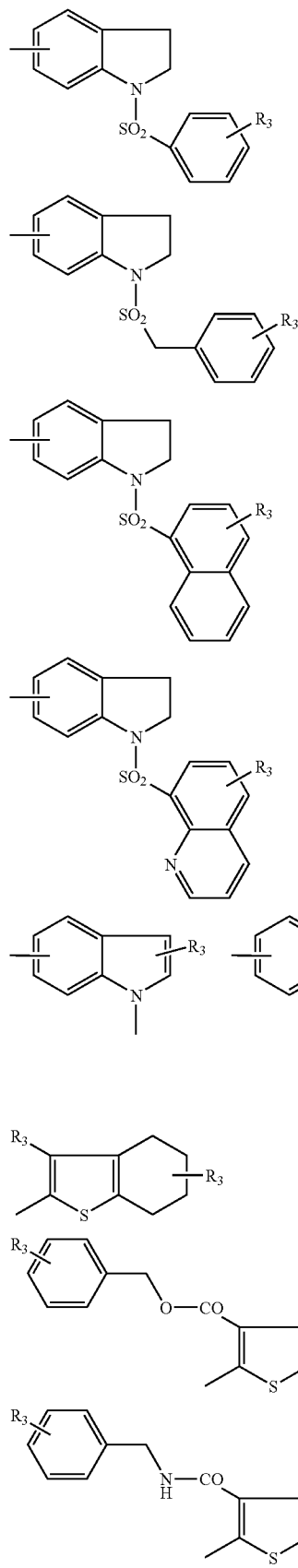
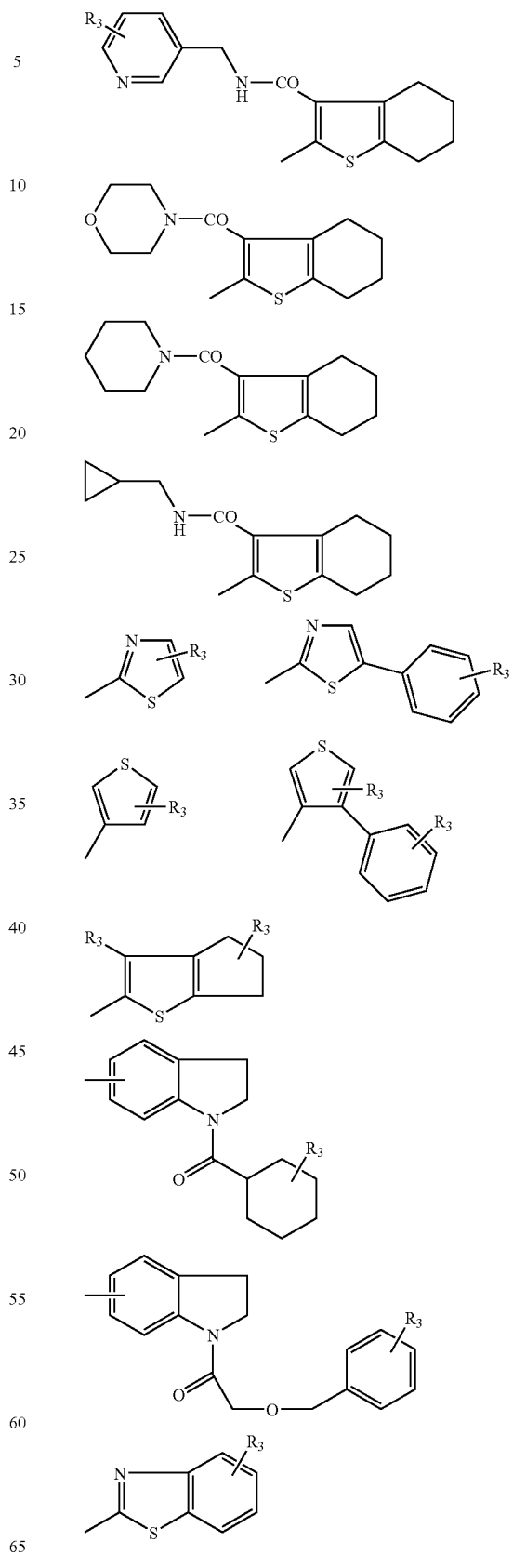

-continued

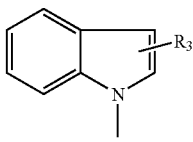

In this group of compounds, $R_3$ preferably represents hydrogen, hydroxyl or (1–6C) alkylaminocarbonyl.

Examples of particular values for Lp in this sub-group are pyrrolidin-1-yl, piperidin-1-yl, N-methyl, N-ethylaminocarbonylpiperidin-1-yl, decahydroisoquinolin-2-yl and 2,3-dihydroindol-1-yl.

Another group of compounds of particular interest is that in which L represents $CONR_{1d}$ (such as CONH or $CONCH_3$) and Lp represents

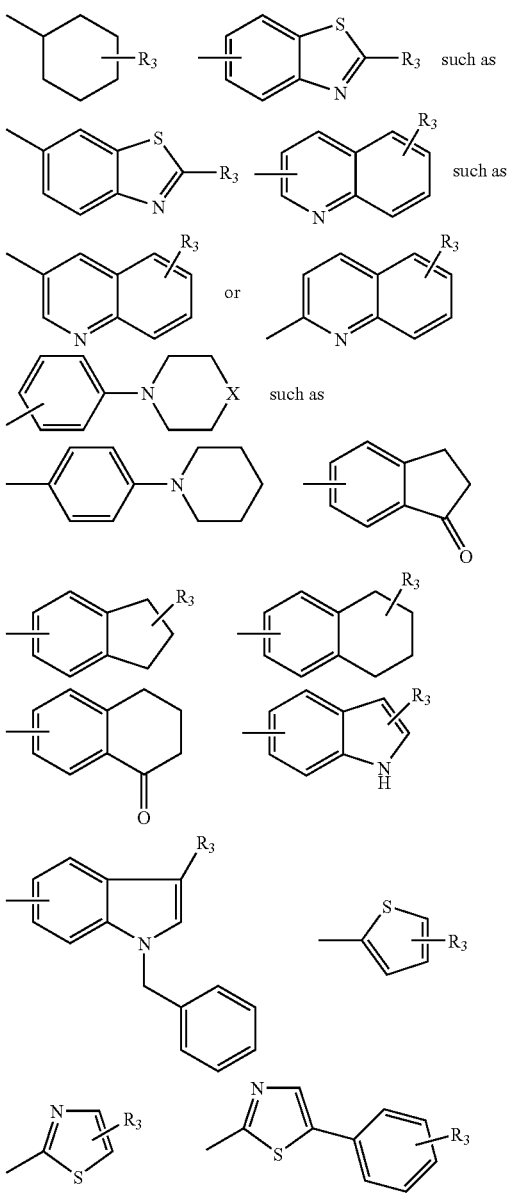

-continued

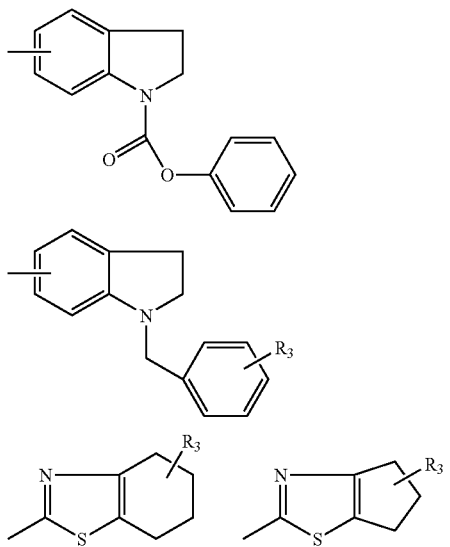

or additionally from

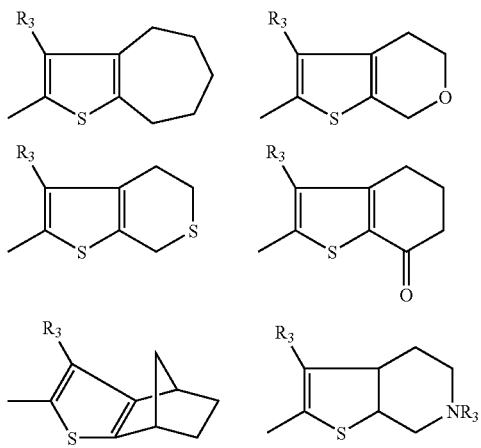

wherein $R_3$ is as hereinbefore defined; and
X represents CH or N.

In the Lp groups depicted above, preferably L represents CO when the Lp group is linked to L through N, or $CONR_{1d}$ (such as CONH or $CONCH_3$) when the Lp group is linked to L through C.

One group of compounds of particular interest is that in which L represents CO and Lp represents

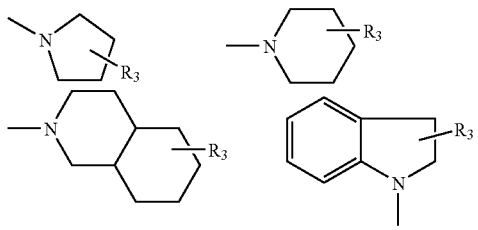

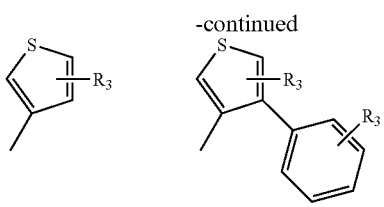

in which X is CH or N.

In this group of compounds, each $R_3$ is preferably selected independently from hydrogen, amino, hydroxy, (1–6C)alkyl, (1–6C)alkanoyl, (1–6C)alkanoyloxy, (1–5C)alkoxycarbonyl (1–6C)alkyl, amino(1–6C)alkyl or cyano.

Thus, values for $R_3$ in this group include hydrogen, amino, hydroxy, alkyl or aminoalkyl.

Examples of particular values are:
(i) 2-aminocyclohexyl;
(ii) 2-aminobenzothiazol-6-yl;
(iii) quinolin-3-yl or 8-acetoxyquinolin-2-yl;
(iv) 4-piperidin-1-ylphenyl or 4-piperazin-1-ylphenyl;
(v) 1-oxoindan-5-yl;
(vi) indan-5-yl;
(vii) tetrahydronaphth-6-yl or 1-methyltetrahydronaphth-6-yl;
(viii) 1-oxotetrahydronaphth-6-yl or 1-oxotetrahydronaphth-7-yl;
(ix) 2,3-dimethylindol-5-yl;
(x) N-benzyl-3-acetylindol-5-yl or N-benzyl-3-acetylindol-7-yl;
(xi) 3-ethoxycarbonyl-4,5-dimethylthien-2-yl;
(xii) 4-methyl-5-acetylthiazol-2-yl, 4,5-dimethylthiazol-2-yl, 4-methyl-5-ethoxycarbonylthiazol-2-yl, 3-cyano-4-methyl-5-ethoxycarbonylthiazol-2-yl or 4-methoxycarbonylmethyl-5-methylthiazol-2-yl;
(xiii) 5-phenylthiazol-2-yl;
(xiv) 2-methoxycarbonyl-5-(t-butyl)thien-3-yl;
(xv) 2-acetyl-5-phenylthien-3-yl; and
(xvi) 5,6-dihydro-3-methoxycarbonyl-4H-cyclopenta(b)thiophen-2-yl.

Another group of compounds of particular interest is that in which L represents $CONR_{1d}$ (such as CONH or $CONCH_3$) and Lp represents

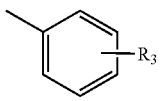

in which $R_3$ is (1–6C)alkylaminocarbonyl, N-(1–6C)alkylamino(1–6C)alkanoyl, N-(1–6C)alkanoylamino(1–6C)alkanonyl, C-hydroxyamino(1–6C)alkanoyl, hydrogen, (1–6C)alkoxy, (1–6C)alkyl, amino(1–6C)alkyl, aminocarbonyl, hydroxy(1–6C)alkyl, (1–6C)alkoxy(1–6C)alkyl, (1–6C)alkoxycarbonyl, (1–6C)acyloxymethoxycarbonyl, (1–6C)alkylamino, amino, halo, cyano, nitro, thiol, (1–6C)alkylthio, (1–6C)alkylsulphonyl, (1–6C)alkylsulphenyl, triazolyl, imidazolyl, tetrazolyl, hydrazido, (1–6C)alkylimidazolyl, thiazolyl, (1–6C)alkylthiazolyl, (1–6C)alkyloxazolyl, oxazolyl, (1–6C)alkylsulphonamido, (1–6C)alkylaminosulphonyl, aminosulphonyl, (1–6C)haloalkoxy or (1–6C)haloalkyl.

Preferably the phenyl group is unsubstituted or substituted by one or two $R_3$ groups.

Examples of particular values are phenyl, 3-cyano-4-methylphenyl, 3-aminocarbonylphenyl, 4-aminocarbonylphenyl, 4-chloro-3-aminocarbonylphenyl, 4-chlorophenyl, 3,5-dichlorophenyl, 3-aminomethylphenyl, 4-methyl-3-acetylaminophenyl, 4-(1-hydroxethyl)phenyl and 4-isopropylphenyl.

Another particular group of compounds of formula I is that in which L represents $CONR_{1d}$ (such as CONH or $CONCH_3$) and Lp represents

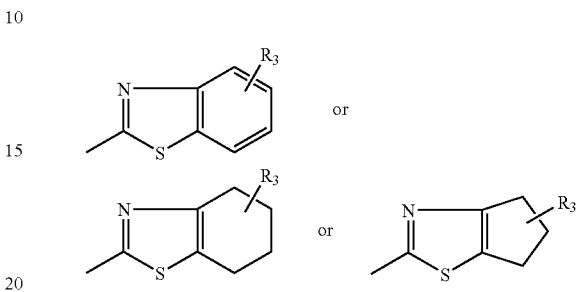

In this group of compounds, the heterocyclic group is preferably substituted by one or two $R_3$ groups. Each $R_3$ group is preferably selected from hydrogen, halogen such as chlorine, (1–6C)alkyl, such as methyl, and (1–6C)alkoxy, such as methoxy.

Accordingly, examples of particular values for Lp are: benzothiazol-2-yl, 4-chlorobenzothiazol-2-yl, 4-methyl-benzo-thiazol-2-yl, 6-methylbenzothiazol-2-yl, 4-methoxy-benzo-thiazol-2-yl and 5,6-dimethylbenzothiazol-2-yl. Further examples are 4-methoxy-7-methylbenzothiazol-2-yl, 6-nitrobenzothiazol-2-yl, 4,7-dimethoxybenzothiazol-2-yl, 4,5,6,7-tetrahydrobenzothiazol-2-yl, 5-methyl-4,5,6,7-tetrahydrobenzothiazol-2-yl, 6-methyl-4,5,6,7-tetrahydrobenzothiazol-2-yl, 5-ethyl-4,5,6,7-tetrahydrobenzothiazol-2-yl and 7-ethyl-4,5,6,7-tetrahydrobenzothiazol-2-yl.

Another particular group of compounds of formula I is that in which L represents $CONR_{1d}$ (such as CONH or $CONCH_3$) and Lp represents

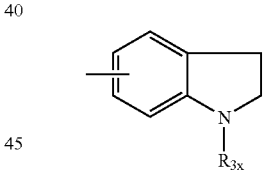

in which $R_{3x}$ represents $R_3$ or a group of formula $-(X_{1y})_p-(G_1)-R_j$ in which p is 0 or 1; $X_{1y}$ represents CO, COO, CONH or $SO_2$; $G_1$ represents (1–3C)alkanediyl, $CH_2OCH_2$ or, when p is 1, a bond; and $R_j$ represents a carbocyclic or heterocyclic group, optionally substituted by $R_3$.

Within this group of compounds, a sub-group of compounds may be identified in which $R_{3x}$ represents $R_3$ or a group of formula $-(CO)_p-(G_1)-R_j$ in which p is 0 or 1 and $G_1$ represents (1–3C)alkanediyl or, when p is 1, a bond.

It will be appreciated that when Lp represents a group as described above, it corresponds to a group in which Lp is a combination of a heterocyclic group (2,3-dihydroindolyl), a carbocyclic or heterocyclic group ($R_j$) and optionally an alkyl group ($G_1$), which groups are linked by a single bond or a carbonyl group. Accordingly, examples of particular values for $R_j$ are the examples given above for a carbocyclic or heterocyclic group forming part of Lp. Particular mention may be made of pyrrolidinyl, such as pyrrolidin-1-yl or pyrrolidin-2-yl; piperidinyl, such as piperidin-3-yl or piperidin-4-yl; aminocycloalkyl, such as 2-aminocyclohexyl or 4-aminocyclohexyl; phenyl; 2-hydroxypheny; 3-hydroxphenyl; 4-hydroxyphenyl; 4-aminomethylphenyl; 4-acetylaminomethylphenyl; 4-isopropylphenyl; 3,4-dihydroxyphenyl; naphthyl, such as 1-naphthyl; quinolinyl, such as 8-quinolinyl; aminothiazolyl, such as 2-aminothiazol-4-yl; formamidothiazolyl, such as 2-formamidothiazol-4-yl; imidazolyl, such as imidazol-4-yl; and pyridyl, such as pyrid-2-yl, pyrid-3-yl and pyrid-4-yl.

Examples of values for $G_1$ are a bond, —$CH_2$—, $CH_2CH_2$ and $CH_2OCH_2$.

The 2,3-dihydroindolyl group in the above formula is preferably a 2,3-dihydroindol-5-yl or -6-yl group, especially a 2,3-dihydroindol-6-yl group.

Examples of structures of compounds comprising a 2,3-dihydroindolyl group as described above are:

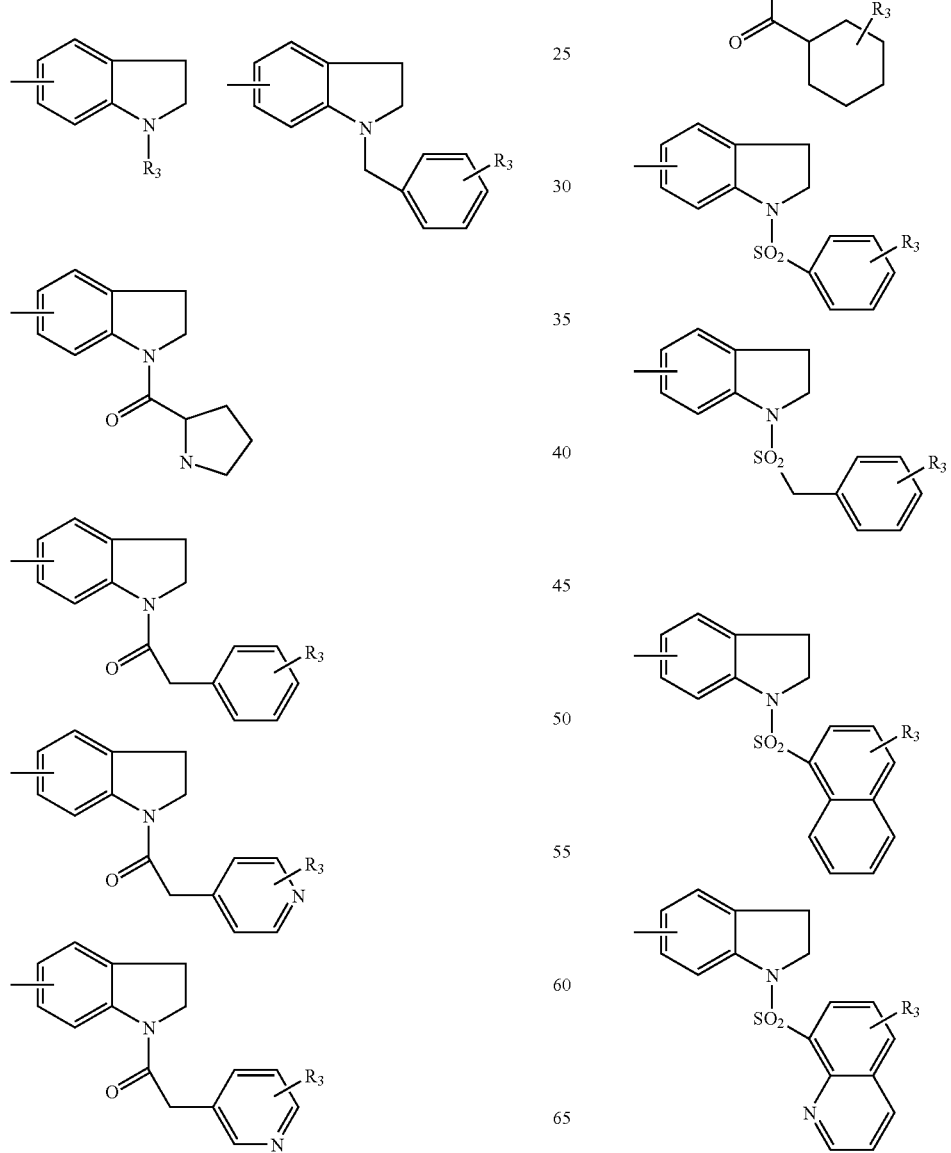

-continued

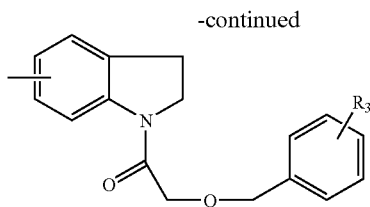

When R₃ is a substituent on the 1-position of a 2,3-dihydroindolyl group, it preferably represents an amino acid residue; (1–6C)alkylaminocarbonyl; N-(1–6C)alkylamino (1–6C)alkanoyl; N-alkanoylaminoalkanonyl; C-hydroxyamino(1–6C)alkanoyl; hydroxy(1–6C)alkanoylamino (1–6C)alkanoyl; di(1–6C)alkylaminosulfonyl; hydrogen; (1–6C)alkyl; (1–6C)alkanoyl; (1–6C)alkoxycarbonyl; (1–6C)acyloxymethoxycarbonyl; amino(1–6C) alkyl; amido (CONH₂); amino(1–6C)alkanoyl; aminocarbonyl(1–6C)alkanoyl; hydroxy(1–6C)alkyl; hydroxy(1–6C)alkanoyl; (1–6C)alkoxy(1–6C)alkyl; (1–6C)alkoxycarbonyl(1–6C) alkyl; (1–6C)alkoxycarbonyl; (1–6C)alkanoylamino; or (1–6C)alkylsulfonyl. Examples of particular values are: N-methylaminoacetyl, N-acetylaminoacetyl, N-acetylaminopropanoyl, N-(2-methylpropanoyl)aminoacetyl, N-acetylalaninoyl, serinoyl, threoninoyl, aspartoyl, glutamoyl, 2-hydroxyacetylaminoacetyl, dimethylaminosulfonyl, hydrogen, methyl, acetyl, propanoyl, 2-methylpropanoyl, 3-methylbutyryl, 2-hydroxypropanoyl, hydroxyacetyl, methoxycarbonylmethyl, methoxycarbonyl, amido, aminoacetyl, aminocarbonylacetyl, alaninoyl, methylsulfonyl or ethylsulfonyl group. Another example is ethyl.

Accordingly, examples of particular values for Lp are: 1-(N-methylaminoacetyl)-2,3-dihydroindol-6-yl; 1-(N-acetylaminoacetyl)-2,3-dihydroindol-6-yl; 1-(N-acetylaminopropanoyl)-2,3-dihydroindol-6-yl; 1-N-(2-methylpropanoyl)aminoacetyl)-2,3-dihydroindol-6-yl; 1-(N-acetylalaninoyl)-2,3-dihydroindol-6-yl; 1-(serinoyl)-2,3-dihydroindol-6-yl; 1-(threoninoyl)-2,3-dihydroindol-6-yl; 1-(aspartoyl)-2,3-dihydroindol-6-yl; 1-(glutamoyl)-2,3-dihydroindol-6-yl; 1-(2-hydroxyacetylamino)acetyl-2,3-dihydroindol-6-yl, 1-(2-hydroxyacetylamino)acetyl-2,3-dihydroindol-6-yl, 1-amido-2,3-dihydroindol-6-yl, 2,3-dihydroindol-5-yl; 1-methyl-2,3-dihydroindol-6-yl; 1-allyloxycarbonyl-2,3-dihydroindol-5-yl; 1-acetyl-2,3-dihydroindol-6-yl; 1-propanoyl-2,3-dihydroindol-6-yl; 1-(2-methylpropanoyl)-2,3-dihydroindol-6-yl; 1-(3-methylbutyryl)-2,3-dihydroindol-6-yl; 1-(2-hydroxpropanoyl)-2,3-dihydroindol-6-yl; 1-hydroxacetyl-2,3-dihydroindol-6-yl; 1-methoxycarbonylmethyl-2,3-dihydroindol-6-yl; 1-methoxycarbonyl-2,3-dihydroindol-6-yl; 1-aminoacetyl-2,3-dihydroindol-6-yl; 1-aminocarbonylacetyl-2,3-dihydroindol-6-yl; 1-alaninoyl-2,3-dihydroindol-6-yl; 1-methylsulfonyl-2,3-dihydroindol-6-yl or 1-ethylsulfonyl-2,3-dihydroindol-6-yl. Another example is 1-ethyl-2,3-dihydroindol-5-yl.

When R₃ is a substituent on a cyclohexyl, phenyl, naphthyl, thiazolyl, imidazolyl, pyridyl or quinolinyl group, it is preferably hydrogen, hydroxy, amino, alkanoylamino, alkyl, aminoalkyl or alkanoylaminoalkyl. Examples of particular values are hydrogen, hydroxy, amino, formylamino, isopropyl, aminomethyl and acetylaminomethyl.

Accordingly, further examples of particular values for Lp are: 2,3-dihydroindol-5-yl; 1-(2-aminocyclohexyl)-carbonyl-2,3-dihydroindol-6-yl, 1-(4-aminocyclohexyl)-acetyl-2,3-dihydroindol-6-yl, 1-prolinoyl-2,3-dihydroindol-6-yl, 1-pyrrolidin-2-ylacetyl-2,3-dihydroindol-6-yl, 1-piperidin-3-ylcarbonyl-2,3-dihydroindol-6-yl, 1-piperidin-3-ylacetyl-2,3-dihydroindol-6-yl, 1-phenylacetyl-2,3-dihydroindol-6-yl, 1-(2-hydroxy)phenylacetyl-2,3-dihydroindol-6-yl, 1-(3-hydroxy)phenylacetyl-2,3-dihydroindol-6-yl, 1-(4-hydroxy) phenylacetyl-2,3-dihydroindol-6-yl, 1-(3,4-dihydroxy) phenylacetyl-2,3-dihydroindol-6-yl, 1-(4-aminomethyl) phenylacetyl-2,3-dihydroindol-6-yl, 1-(4-acetylaminomethyl)phenylacetyl-2,3-dihydroindol-6-yl, 1-(4-isopropyl)phenylacetyl-2,3-dihydroindol-6-yl, 1-phenylsulfonyl-2,3-dihydroindol-6-yl, 1-benzylsulfonyl-2,3-dihydroindol-6-yl, 1-naphth-1-ylsulfonyl-2,3-dihydroindol-6-yl, 1-quinolin-8-ylsulfonyl-2,3-dihydroindol-6-yl, 1-(4-pyridyl)acetyl-2,3-dihydroindol-6-yl, 1-(3-pyridyl)acetyl-2,3-dihydroindol-6-yl, 1-imidazol-4-ylacetyl-2,3-dihydroindol-6-yl, 1-(2-aminothiazol-4-yl)acetyl-2,3-dihydroindol-6-yl, and 1-(2-formamidothiazol-4-yl)acetyl-2,3-dihydroindol-6-yl, and 1-benzyl-2,3-dihydroindol-6-yl.

Another particular group of compounds of formula I is that in which L represents CONR$_{1d}$ (such as CONH or CONCH₃) and Lp represents

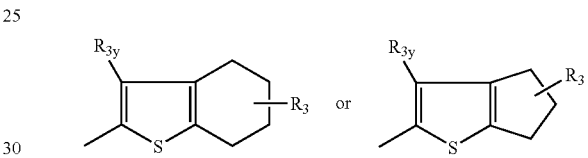

in which R$_{3y}$ represents R₃ or a group of formula

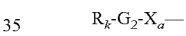

$R_k$-$G_2$-$X_a$— in which G₂ represents a bond or (1–3C)alkanediyl, X$_a$ represents a bond, CO, OCO, COO or NHCO, and R$_k$ represents a carbocyclic or heterocyclic group, optionally substituted by R₃.

It will be appreciated that when Lp represents a group as described above, it corresponds to a group in which Lp is a combination of a heterocyclic group (tetrahydrobenzothienyl), a carbocyclic or heterocyclic group (R$_k$) and optionally an alkyl group (G₂), which groups are linked by a single bond, or a CO, OCO, COO or NHCO group. Accordingly, examples of particular values for R$_k$ are the examples given above for a carbocyclic or heterocyclic group forming part of Lp. Particular mention may be made of phenyl; cycloalkyl, such as cyclopropyl; azacycloalkyl, such as piperidin-1-yl; oxazacycloalkyl, such as morpholino; and pyridyl, such as pyrid-3-yl. Further particular mention may be made of diazacycloalkyl, such as piperazin-1-yl; furyl, such as fur-2-yl; thienyl, such as thien-2-yl; pyrrolidin-1-yl and pyrid-2-yl.

Examples of values for G₂ are a bond, —CH₂—, and CH₂CH₂.

Examples of structures of groups comprising a 4,5,6,7-tetrahydrobenzothienyl group as described above are:

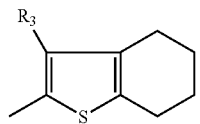

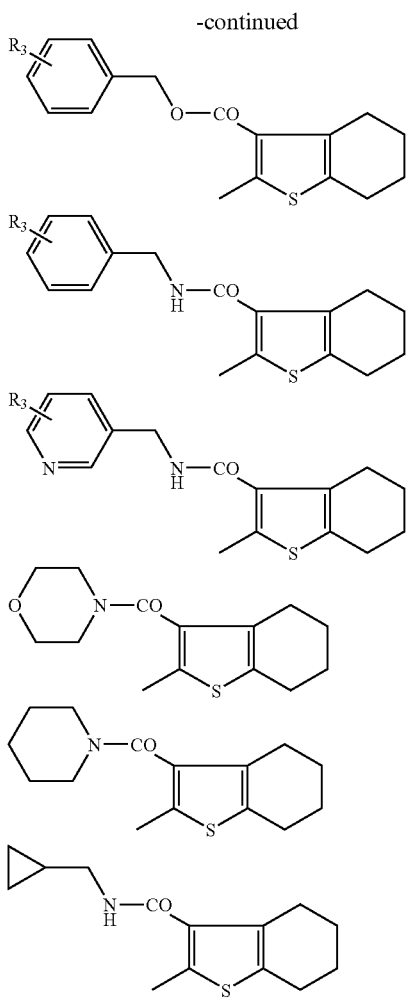

Further examples of structures of groups comprising a 4,5,6,7-tetrahydrobenzothienyl group as described above are:

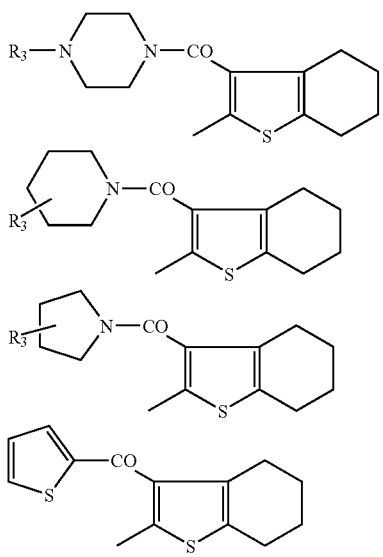

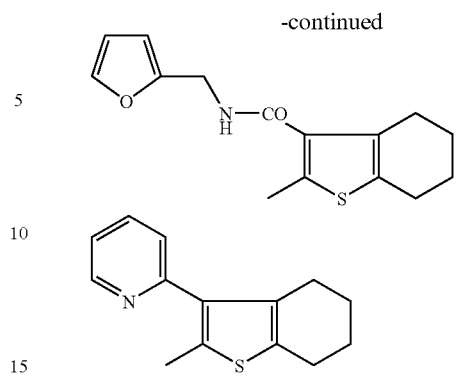

When R₃ is present as a substituent on the 1-position of a piperazinyl group, it is preferably hydrogen, (1–6C)alkanoyl, such as formyl, or (1–6C)alkoxycarbonyl, such as ethoxycarbonyl.

When R₃ is present as a substituent on a piperidin-1-yl group, it is preferably at the 3- or 4-position and is preferably hydrogen, (1–6C)alkyl, such as methyl; amido or (1–6C) alkoxycarbonyl, such as ethoxycarbonyl.

When R₃ is present as a substituent at the 3-position of a 4,5,6,7-tetrahydrobenzothiophene group, it preferably represents a carboxy group; a (1–6C)alkoxycarbonyl group, such as methoxycarbonyl or ethoxycarbonyl; or a (1–6C) alkylaminocarbonyl group, such as N-1,3-dimethylbutylaminocarbonyl. Other examples of values for a (1–6C) alkylamincarbonyl group are methylaminocarbonyl and isobutylaminocarbonyl.

Accordingly, examples of particular values for Lp are: 3-carboxy-4,5,6,7-tetrahydrobenzothien-2-yl, 3-ethoxy-carbonyl-4,5,6,7-tetrahydrobenzothien-2-yl and 3-N-(2,3-dimethylbutylaminocarbonyl-4,5,6,7-tetrahydrobenzothien-2-yl. Further examples are 3-N-methylaminocarbonyl-4,5,6,7-tetrahydrobenzothien-2-yl and 3-N-isobutylaminocarbonyl-4,5,6,7-tetrahydrobenzothien-2-yl.

Further examples of R₃ when it is present as a substituent at the 3-position of a 4,5,6,7-tetrahydrobenzothiophene group are N,N-dialkylaminocarbonyl, such as dimethylaminocarbonyl or diethylaminocarbonyl; amido; (1–6C)alkoxycarbonyl, such as methoxycarbonyl or ethoxycarbonyl; cyano and (1–6C)alkylsulfonyl, such as methylsulfonyl.

Accordingly, further examples of Lp are 3-N,N-dimethylaminocarbonyl-4,5,6,7-tetrahydrobenzothien-2-yl, 3-N,N-diethylaminocarbonyl-4,5,6,7-tetrahydrobenzothien-2-yl, 3-ethoxycarbonyl-4,5,6,7-tetrahydrobenzothien-2-yl, 3-amido-4,5,6,7-tetrahydrobenzothien-2-yl, 3-methylsulfonyl-4,5,6,7-tetrahydrobenzothien-2-yl, 3-cyano-4,5,6,7-tetrahydrobenzothien-2-yl and 3-ethoxycarbonyl-4H-cyclopenta(b)thienyl.

When R₃ is present as a substituent on a phenyl or pyridyl group, it is preferably a hydrogen atom.

Accordingly, examples of particular values for Lp are: 3-benzyloxycarbonyl-4,5,6,7-tetrahydrobenzothien-2-yl, 3-benzylaminocarbonyl-4,5,6,7-tetrahydrobenzothien-2-yl, 3-(3-pyridyl)methylaminocarbonyl-4,5,6,7-tetrahydro-benzothien-2-yl, 3-cyclopropylmethylaminocarbonyl-4,5,6,7-tetrahydrobenzothien-2-yl, 3-morpholinocarbonyl-4,5,6,7- tetrahydrobenzothien-2-yl and 3-piperidinocarbonyl-4,5,6,7-tetrahydrobenzothien-2-yl. Further examples are: 3-piperazin-1-ylcarbonyl-4,5,6,7-tetrahydrobenzothien-2-yl, 3-(4-formyl)piperazin-1-ylcarbonyl-4,5,6,7-tetrahydrobenzothien-2-yl, 3-(4-ethoxycarbonyl)piperazin-1-ylcarbonyl-4,5,6,7-tetrahydrobenzothien-2-yl, 3-(4-methoxybenzyl)aminocarbonyl-4,5,6,7-tetrahydrobenzothien-2-yl, 3-(4-ethoxycarbonyl)-piperidin-1-ylcarbonyl-4,5,6,7-tetrahydrobenzothien-2-yl, 3-(3-amido)-piperidin-1-ylcarbonyl-4,5,6,7-tetrahydrobenzothien-2-yl, 3-(4-amido)-piperidin-1-ylcarbonyl-4,5,6,7-tetrahydrobenzothien-2-yl, 3-methylpiperidin-1-ylcarbonyl-4,5,6,7-tetrahydrobenzothien-2-yl, 3-(2-thienyl)carbonyl-4,5,6,7-tetrahydrobenzothien-2-yl, 3-(2-furylmethylamino-carbonyl-4,5,6,7-tetrahydrobenzothien-2-yl, 3-(1-pyrrolidinyl)carbonyl-4,5,6,7-tetrahydrobenzothien-2-yl and 3-(2-pyridyl)-4,5,6,7-tetrahydrobenzothien-2-yl.

When $R_3$ is present as a substituent at the 4,5,6 and/or 7 position of a 4,5,6,7-tetrahydrobenzothien-2-yl group or the 4,5 and/or 6 position of a 4H-cyclopenta)b)thienyl group, it is preferably a hydrogen atom or a (1–6C)alkyl group, such as methyl.

Examples of particlar values for Lp are accordingly 3-ethoxycarbonyl-4-methyl-4,5,6,7-tetrahydrobenzothien-2-yl, 3-ethoxycarbonyl-5-methyl-4,5,6,7-tetrahydrobenzothien-2-yl and 3-ethoxycarbonyl-6-methyl-4,5,6,7-tetrahydrobenzothien-2-yl.

Another particular group of compounds of formula I is that in which L represents $CONR_{1d}$ (such as CONH or $CONCH_3$) and Lp represents

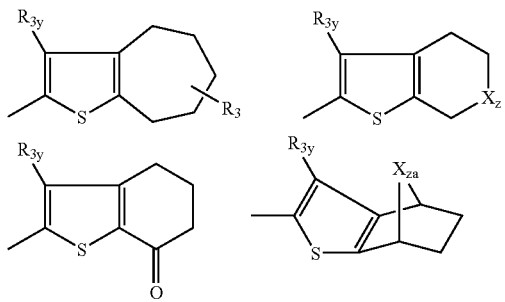

in which $R_{3y}$ is as defined hereinabove, $X_z$ is O, S or $NR_z$ in which $R_z$ is independently selected from one of the values for $R_{3y}$, and $X_{za}$ is $CH_2$ or is as defined for $X_z$.

Examples of particular values for $R_{3y}$ are (1–6C)alkoxycarbonyl, such as ethoxycarbonyl, N,N-dialkylaminocarbonyl, such as N,N-dimethylaminocarbonyl, and cyano.

$R_3$ is preferably hydrogen.

$R_z$ is preferably hydrogen, (1–6C)alkanoyl, amino(1–6C)alkanoyl or benzyloxycarbonyl. Examples of particular values for $R_z$ are hydrogen, acetyl, aminoacetyl and benzyloxycarbonyl.

Accordingly, examples of particular values for Lp are: 3-ethoxycarbonyl-tetrahydro-4H-cyclohepta(b)thien-2-yl, 3-ethoxycarbonyl-4,5-dihydro-5H-thieno[2,3-c]pyranyl, 3-ethoxycarbonyl-4,5-dihydro-5H-thieno[2,3-c]thiopyranyl, 3-dimethylamido-6-benzyloxycarbonyltetrahydrothieno[2,3-b]pyridin-2-yl, 3-dimethylamido-tetrahydrothieno[2,3-b]pyridin-2-yl, 3-dimethylamido-6-acetyltetrahydrothieno[2,3-b]pyridin-2-yl, 3-dimethylamido-6-aminoacetyltetrahydrothieno-[2,3-b]pyridin-2-yl, 3-dimethylamido-6-methoxyacetyl-tetrahydrothieno[2,3-b]pyridin-2-yl and 3-ethoxycarbonyl-tetrahydro-4,7-methanobenzo(b)thophen-2-yl.

The cyclic group attached to the alpha carbon is preferably cyclohexyl, piperidin-4-yl, 3,4-methylenedioxy-phenyl, fur-2-yl, thien-2-yl, thien-3-yl, imidazol-4-yl, oxazol-4-yl, oxazol-5-yl, thiazol-4-yl, thiazol-5-yl, pyrid-2-yl, pyrid-3-yl, pyrid-4-yl, pyrimidin-2-yl, pyrimidin-4-yl, pyrimidin-5-yl, pyrazin-2-yl, pyrazin-3-yl, naphth-1-yl, naphth-2-yl, indol-5-yl, indan-5-yl, 3,4-dihydrobenzofur-5-yl, benzofur-2-yl or benzo[b]thien-2-yl group, optionally substituted by $R_{3a}$ or $R_{3i}X_i$ in which $X_i$ is a bond, O, NH or $CH_2$ and $R_{3i}$ is phenyl optionally substituted by $R_{3a}$.

Examples of particular values for $R_{3a}$ are:
hydrogen;
hydroxyl;
for (1–6C)alkoxy: methoxy, ethoxy or isopropoxy;
for (1–6C)alkyl: methyl, ethyl or isopropyl;
for: (1–6C)alkanoyl: acetyl, propanoyl or isopropanoyl,
for (1–6C)alkylaminoalkyl: methylaminomethyl or dimethylaminomethyl;
for (1–6C)hydroxyalkyl: hydroxymethyl carboxy;
for (1–6C)alkoxyalkyl: methoxymethyl;
for (1–6C)alkoxycarbonyl: methoxycarbonyl or ethoxycarbonyl;
for (1–6C)alkylaminocarbonyl: methylaminocarbonyl or dimethylaminocarbonyl;
for (1–6C)aminoalkyl: aminomethyl;
$CONH_2$;
$CH_2CONH_2$;
aminoacetyl;
for (1–6C)alkanoylamino: formylamino or acetylamino;
for hydroxy(1–6C)alkanoylamino: hydroxyacetylamino;
for amino(1–6C)alkanoylamino: aminoacetylamino;
for (1–6C)alkylamino(1–6C)alkanoylamino: (1–6C)alkylaminoacetyl, such as methylaminoacetyl;
for di(1–6C)alkylamino(1–6C)alkanoylamino: dimethylaminoacetylamino;
for (1–6C)alkoxycarbonylamino: methoxycarbonylamino, ethoxycarbonylamino or t-butoxycarbonylamino;
amino;
for halo: fluoro or chloro;
cyano;
nitro;
thiol;
for (1–6C)alkylthio: methylthio;
for (1–6C)alkylsulphonyl: methylsulphonyl or ethylsulphonyl;
for (1–6C)alkylsulphenyl: methylsulphenyl;
for imidazolyl: imidazol-4-yl;
hydrazido;
for (1–6C)alkylimidazolyl: 2-methylimidazol-4-yl;
for (1–6C)alkylsulphonamido: methylsulphonylamido or ethylsulphonylamido;
for (1–6C)alkylaminosulphonyl: methylaminosulphonyl or ethylaminosulphonyl;
aminosulphonyl;
for (1–6C)haloalkoxy: trifluoromethoxy; and
for (1–6C)haloalkyl: trifluoromethyl.

An example of a particular value for $R_{3i}$ is phenyl.

Examples of particular values for $R_{3i}X_i$ are phenyl, phenoxy, phenylamino and benzyl.

Cy is preferably unsubstituted or substituted by one or two $R_{3a}$ groups.

Preferably $R_{3a}$ is hydrogen, hydroxyl, methyl, ethyl, isopropyl, acetyl, propanoyl, isopropanoyl, isopropoxy, amino, aminomethyl, hydroxymethyl, carboxy, amido, formylamino, acetylamino, aminoacetyl or carboxy.

Examples of particular values for Cy are cyclohexyl, piperidin-4-yl, 1-acetylpiperidin-4-yl, 1-propanoylpiperidin-4-yl, 1-isobutyrylpiperidin-4-yl, 1-aminoacetylpiperidin-4-yl, 5-methylfur-2-yl, imidazol-4-yl, 2-methylthiazol-4-yl, 2-aminothiazol-4-yl, 2-formylaminothiazol-4-yl, 2-aminothiazol-5-yl, 2-formylaminothiazol-5-yl, 2-phenylthiazol-4-yl, 4-aminopyrid-3-yl, 6-methylpyrid-2-yl, 3-amino-pyrid-4-yl, naphth-1-yl, naphth-2-yl, benzofur-2-yl or 3-methylbenzothien-2-yl. Further examples of particular values for Cy are 6-aminopyrid-3-yl, 2-ethylthiazol-4-yl, 2-benzylthiazol-4-yl, 2-methylsulfonamidothiazol-4-yl, 2-chloropyrid-3-yl, 2-hydroxyacetylaminothiazol-4-yl, 2-N,N-dimethylaminoacetyl-aminothiazol-4-yl, indol-5-yl, indan-5-yl and 3,4-dihydrobenzofur-2-yl.

In one group of compounds, the cyclic group attached to the alpha carbon is cycloalkyl (such as cyclohexyl), piperidinyl (such as piperidin-4-yl), 3,4-methylenedioxy-phenyl, furyl (such as fur-2-yl), thienyl (such as thien-2-yl or thien-3-yl), imidazolyl (such as imidazol-4-yl), thiazolyl (such as thiazol-4-yl or thiazol-5-yl), pyridyl (such as pyrid-2-yl, pyrid-3-yl or pyrid-4-yl), naphthyl (such as naphth-1-yl or naphth-2-yl), benzofuryl (such as benzofur-2-yl), benzo[b]thienyl (such as benzo[b]thien-2-yl) group, optionally substituted by $R_{3a}$ or $R_{3i}X_i$ in which $X_i$ is a bond, O, NH or $CH_2$ and $R_{3i}$ is phenyl optionally substituted by $R_{3a}$; and each $R_{3a}$ independently is hydrogen, hydroxyl, (1–6C) alkoxy, (1–6C) alkyl, (2–6C)alkenyl, (2–6C)alkynyl, (1–6C) alkanoyl, (1–6C) alkylaminoalkyl, hydroxy(1–6C)alkyl, carboxy, (1–6C) alkoxyalkyl, (1–6C) alkoxycarbonyl, (1–6C) alkylaminocarbonyl, amino(1–6C)alkyl $CONH_2$, $CH_2CONH_2$, aminoacetyl, (1–6C)alkanoylamino, (1–6C) alkoxycarbonylamino, amino, halo, cyano, nitro, thiol, (1–6C) alkylthio, (1–6C) alkylsulphonyl, (1–6C) alkylsulphenyl, imidazolyl, hydrazido, (1–6C)alkylimidazolyl, (1–6C) alkylsulphonamido, (1–6C) alkylaminosulphonyl, aminosulphonyl, (1–6C) haloalkoxy, or (1–6C) haloalkyl.

Within this group, examples of values for $R_{3a}$ are hydrogen; hydroxyl; methoxy; ethoxy; isopropoxy; methyl; ethyl; isopropyl; acetyl; propanoyl; isopropanoyl; methylaminomethyl; dimethylaminomethyl; hydroxymethyl; carboxy; methoxymethyl; methoxycarbonyl; ethoxycarbonyl; methylaminocarbonyl; dimethylaminocarbonyl; aminomethyl; $CONH_2$; $CH_2CONH_2$; aminoacetyl; formylamino; acetylamino; methoxycarbonylamino; ethoxycarbonylamino; t-butoxycarbonylamino; amino; fluoro; chloro; cyano; nitro; thiol; methylthio; methylsulphonyl; ethylsulphonyl; methylsulphenyl; imidazol-4-yl; hydrazido; 2-methylimidazol-4-yl; methylsulphonylamido; ethylsulphonylamido; methylaminosulphonyl; ethylaminosulphonyl; aminosulphonyl; trifluoromethoxy or trifluoromethyl; and $R_{3i}X_i$ is phenyl, phenoxy, phenylamino or benzyl.

Examples of values for Cy in this group are cyclohexyl, piperidin-4-yl, 1-acetylpiperidin-4-yl, 1-propanoylpiperidin-4-yl, 1-isobutyrylpiperidin-4-yl, 1-aminoacetylpiperidin-4-yl, 3,4-methylenedioxyphenyl, 5-methylfur-2-yl, imidazol-4-yl, 2-methylthiazol-4-yl, 2-aminothiazol-4-yl, 2-formylaminothiazol-4-yl, 2-aminothiazol-5-yl, 2-formylaminothiazol-5-yl, 2-phenylthiazol-4-yl, 4-aminopyrid-3-yl, 6-methylpyrid-2-yl, 3-aminopyrid-4-yl, naphth-1-yl, naphth-2-yl, benzofur-2-yl and 3-methylbenzothien-2-yl.

In another group of compounds, the cyclic group attached to the alpha carbon is an optionally $R_{3a}$ substituted cycloalkyl (such as cyclohexyl), piperidinyl (such as piperidin-4-yl), thienyl (such as thien-2-yl or thien-3-yl), thiazolyl (such as thiazol-4-yl or thiazol-5-yl), pyridyl (such as pyrid-3-yl or pyrid-4-yl) or naphthyl (such as naphth-1-yl) group and each $R_{3a}$ independently is hydrogen, hydroxyl, (1–6C) alkoxy, (1–6C) alkyl, (1–6C) alkylaminoalkyl, hydroxy (1–6C)alkyl, (1–6C) alkoxyalkyl, (1–6C) alkoxycarbonyl, (1–6C) alkylaminocarbonyl, amino(1–6C)alkyl $CONH_2$, $CH_2CONH_2$, aminoacetyl, (1–6C)alkanoylamino, (1–6C) alkoxycarbonylamino, amino, halo, cyano, nitro, thiol, (1–6C) alkylthio, (1–6C) alkylsulphonyl, (1–6C) alkylsulphenyl, imidazolyl, hydrazido, (1–6C)alkylimidazolyl, (1–6C) alkylsulphonamido, (1–6C) alkylaminosulphonyl, aminosulphonyl, (1–6C) haloalkoxy, or (1–6C) haloalkyl.

Within this group, examples of values for $R_{3a}$ are hydrogen, hydroxyl, methoxy, ethoxy, methyl, ethyl, methylaminomethyl, dimethylaminomethyl, hydroxymethyl, methoxymethyl, methylaminocarbonyl, dimethylaminocarbonyl, aminomethyl, $CONH_2$, $CH_2CONH_2$, aminoacetyl, formylamino, acetylamino, methoxycarbonylamino, ethoxycarbonylamino, t-butoxycarbonylamino, amino, fluoro, chloro, cyano, nitro, thiol, methylthio, methylsulphenyl, imidazol-4-yl, hydrazido, 2-methylimidazol-4-yl, methylsulphonylamido, ethylsulphonyl-amido, methylaminosulphonyl, ethylaminosulphonyl, amino-sulphonyl, trifluoromethoxy and trifluoromethyl.

Examples of values for Cy in this group are cyclohexyl, piperidin-4-yl, 2-aminothiazol-4-yl, 2-formylaminothiazol-4-yl, 2-aminothiazol-5-yl, 2-formylaminothiazol-5-yl, 4-aminopyrid-3-yl, 3-aminopyrid-4-yl and naphth-1-yl.

A group of compounds of particular interest is that in which Cy is a group of formula

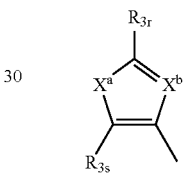

in which one of $X^a$ and $X^b$ is N and the other is NH or S, and each of $R_{3r}$ and $R_{3s}$ is as defined for $R_{3a}$.

Compounds belonging to this sub-group have been found to show good bioavailability.

Preferably $X^a$ is S or NH and $X^b$ is N. Particular mention may be made of compounds in which $X^a$ is S and $X^b$ is N.

Preferably $R_{3s}$ is hydrogen.

Preferably $R_{3r}$ is hydrogen, (1–6C)alkyl, amino, (1–6C) alkanoylamino, hydroxy(1–6C)alkanoylamino, N,N-di (1–6C)alkylaminoalkanoylamino, (1–6C)alkylsulfonylamino, phenyl or benzyl.

Another group of compounds in which good bioavailability has been found are compounds of formula I in which Cy is pyrid-2-yl, pyrimidin-2-yl, pyrimidin-4-yl, pyrazin-2-yl, pyrazin-3-yl or oxazol-4-yl, optionally substituted by $R_{3a}$ or $R_{3xi}$.

The compounds of the invention may be prepared by conventional chemical synthetic routes, e.g. by amide bond formation to couple the aromatic function to the alpha atom and to couple the lipophilic function to the alpha atom. The cyclic group-alpha atom combination may conveniently derive from an alpha amino acid (preferably of D configuration) with the aromatic deriving from for example an acid derivative of a compound based on $R_2$, e.g. an aminomethylbenzoic acid (which is readily available). Amide formation from such reagents (in which any amino or hydroxyl function (especially in an aminomethyl group) may if desired be protected during some or all of the synthesis steps) yields a compound of formula (V).

$$R_2\text{—CONH—CH(Cy)-COOH} \qquad (V)$$

(where $R_2$ represents

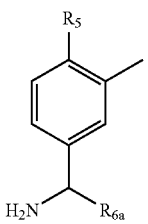

and Cy is as defined above).

Prior to reaction the amino group in an aminoalkyl group should be protected by an appropriate protecting group, PG, e.g. Boc, Z, Fmoc or Bpoc. The use of protecting groups is described in McOmie, "Protective Groups in Organic Chemistry", Plenum, 1973 and Greene, "Protective Groups in Organic Synthesis", Wiley Interscience, 1981.

Compounds of formula (V) are believed to be novel.

According to another aspect, therefore, the present invention provides a compound of formula

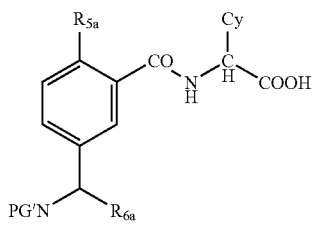

in which PG' represents hydrogen or an amino protecting group (PG) and $R_{5a}$ and $R_{6a}$ are as defined hereinabove, or a salt thereof.

The lipophilic group may then conveniently be introduced by reaction of a compound of formula (V) (or another analogous carboxylic acid) optionally after transformation into an activated form, e.g. an acid chloride or active ester, with a lipophilic group carrying or containing an amine group to produce a compound with the linkage of —CO— or —CO—NR$_{1d}$(CH$_2$)$_m$— from the alpha atom to the lipophilic group. The protecting group, PG, is then removed.

Alternatively a compound of formula V or another analogous carboxylic acid may be transformed into an alcohol by reaction with isobutylchloroformate and reduction with sodium borohydride.

Such an alcohol, e.g. of formula (VI)

$$R_2\text{—CONH—CH(Cy)CH}_2\text{OH} \quad \text{(VI)}$$

can be reacted to introduce the lipophilic group by reactions such as:

oxidation of the alcohol to form a corresponding aldehyde (e.g. by oxidation with manganese dioxide or DMSO/oxalyl chloride or DMSO/SO$_3$ or Dess-Martin reagent) which may be reacted to introduce the lipophilic group by reactions such as:

reaction with an organometallic, eg a Grignard reagent, optionally followed by oxidation of the resulting hydroxyl group (e.g. with MnO$_2$, DMSO/oxalyl chloride or Dess-Martin reagent.

In this way compounds with the linkage of —CO— between the alpha carbon and the lipophilic group may be produced.

An alternative route to these compounds is to carry out any of the above chemical reactions to incorporate the lipophilic group into a protected intermediate such as a compound of formula (VII).

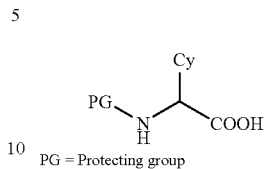

PG = Protecting group

The protecting group may then be removed before coupling of the 3-aminomethylbenzoic acid (optionally protected).

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups (PG) include acyl groups, such as groups of formula RCO in which R represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy. Preferred amino protecting groups include t-butoxycarbonyl (Boc) and benzyl.

α-Amino acids of formula (VII) which are not commercially available can be synthesized by methods known in the art, for example as described in "Synthesis of Optically Active α-Amino Acids" by Robert M. Williams (Pergamon Press, 1989) and "Asymmetric Synthesis of ArylGlycines", Chem. Rev. 1992, 889–917.

Compounds of the type (VII) made be prepared (for example) by one or more of the following methods.

(i) from aryl or heteroaryl aldehydes via the Strecker synthesis or modifications thereof, via Bucherer-Bergs hydantoin synthesis, or via the Ugi methodology (Isonitrile Chemistry, Ugi I. Ed.; Academic: New York, 1971; pp145–199) with removal and replacement of protecting groups;

(ii) from styrenes via Sharpless methodology (J. Am. Chem. Soc. 1998,120, 1207–1217)

(iii) from aryl boronic acids via Petasis methodology (Tetrahedron, 1997, 53, 16463–16470) with removal and replacement of protecting groups;

(iv) from aryl and heteroaryl acetic acids—via Evan's azidation (Synthesis, 1997, 536–540) or by oximation, followed by reduction and addition of protecting groups;

(v) from existing aryl glycines by manipulation of functional groups, for example, alkylation of hydroxy groups, palladium assisted carbonylation of triflates derived from hydroxy groups and further manipulation of the carboxylic esters to give carboxylic acids by hydrolysis, carboxamides by activation of the carboxylic acid and coupling with amines, amines via Curtius reaction on the carboxylic acid; or (vi) from aliphatic, carbocyclic and non-aromatic heterocyclic aldehydes and ketones using a Horner-Emmons reaction with N-benzyloxycarbonyl)-α-phosphonoglycine trimethyl ester (Synthesis, 1992, 487–490).

Examples of synthetic schemes are shown below:

Synthesis of Protected 4-piperidylglycine

See Example 3

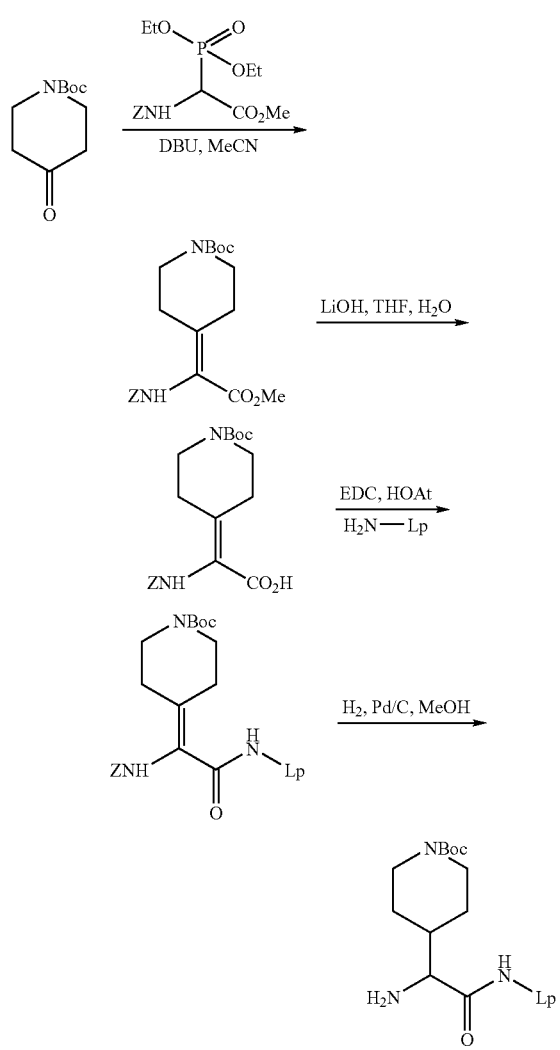

Z is benzyloxycarbonyl

Synthesis of Protected 2-aminothiazol-4-ylglycine

See Examples 4 and 5

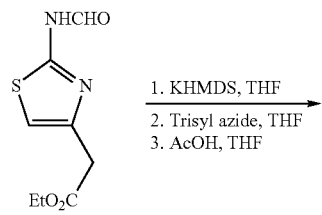

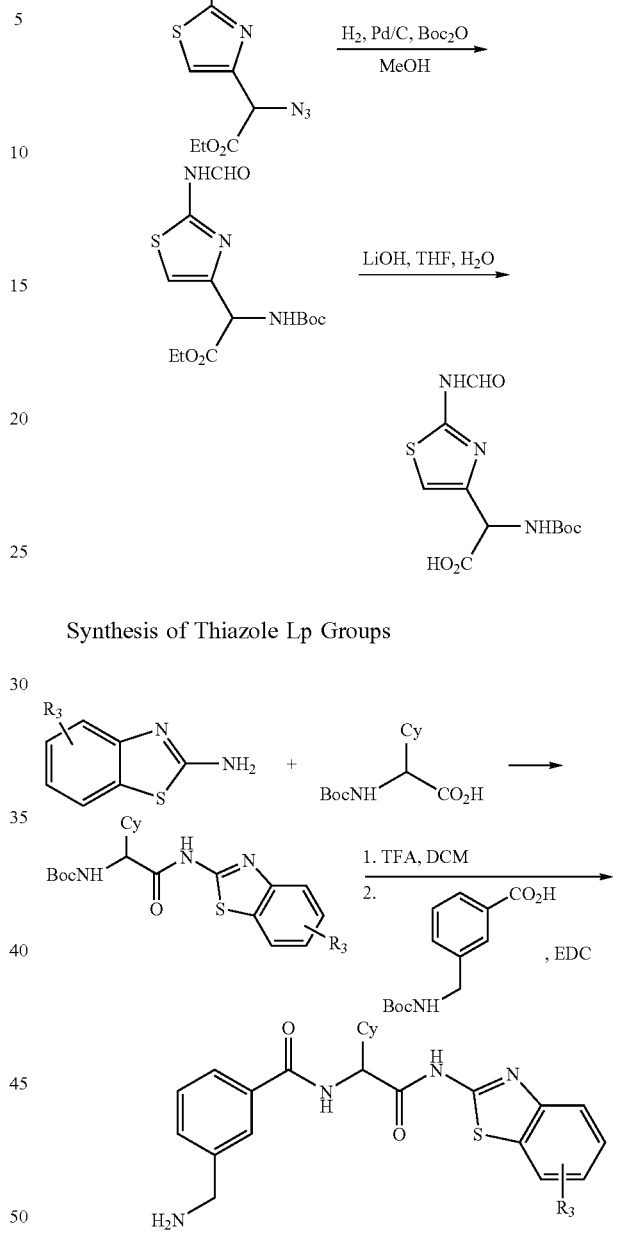

Synthesis of Thiazole Lp Groups

Synthesis of Alternative Thiazole Lp Groups

Benzthiazole Synthesis from Anilines

-continued
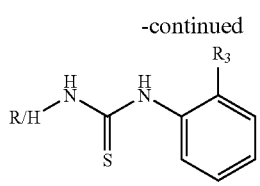
R = removable protecting group
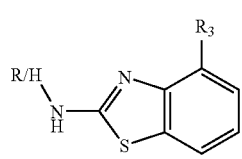
For 7-substitution
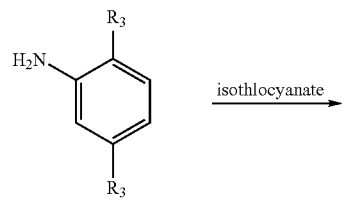 isothiocyanate →
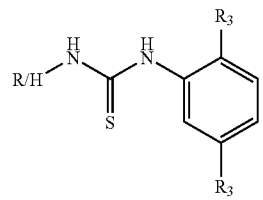
R = removable protecting group
Cyclic Aliphatic Fused Aminothiazoles
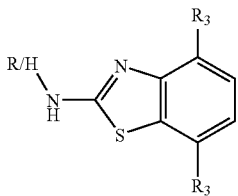
Synthesis of Thiophene Lp Groups
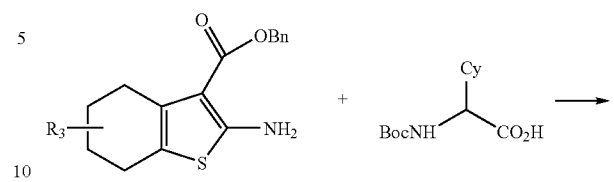
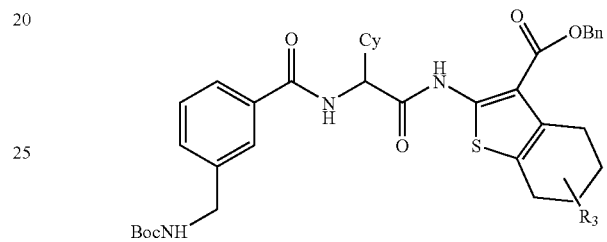
↓
Amides etc
Alkyl/Aryl Thiazolyl Glycines
See Examples 12–13 and 26–27
J. Med. Chem. 1976, 16, 978
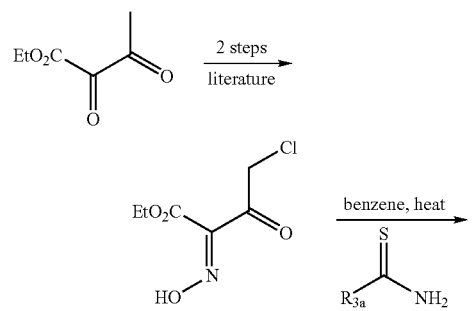
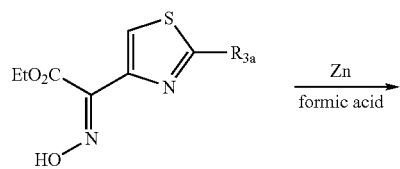
$R_{3a}$ = e.g. alkyl, phenyl, or benzyl
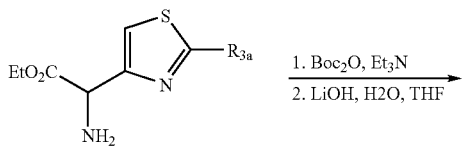

31
-continued
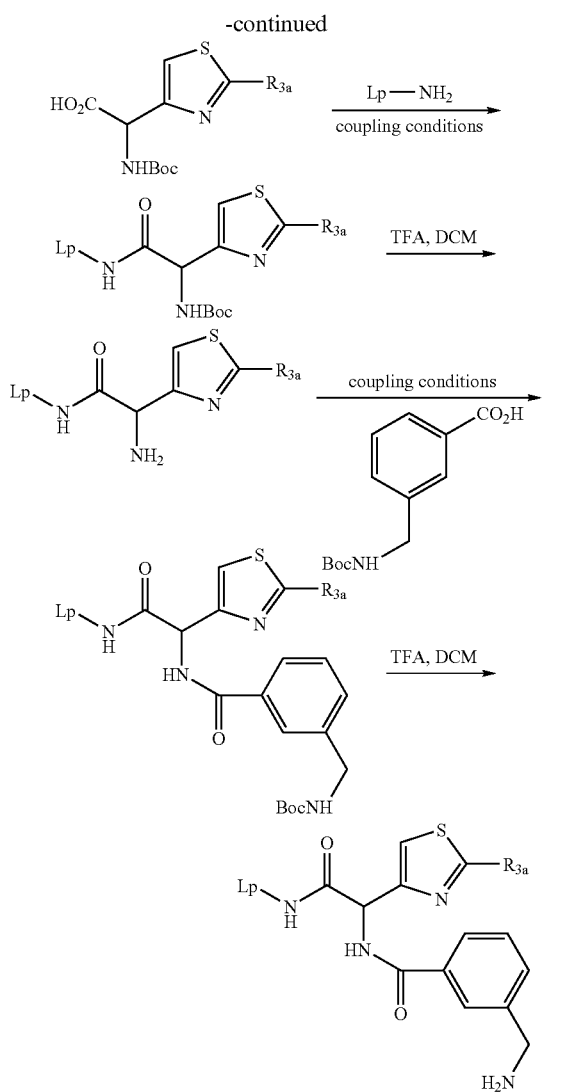
Other Heterocyclic Glycines
Using UgI Methodology
See Examples 6–11 and 21–25
32
Example Aldehyde Synthesis (See Example 23)
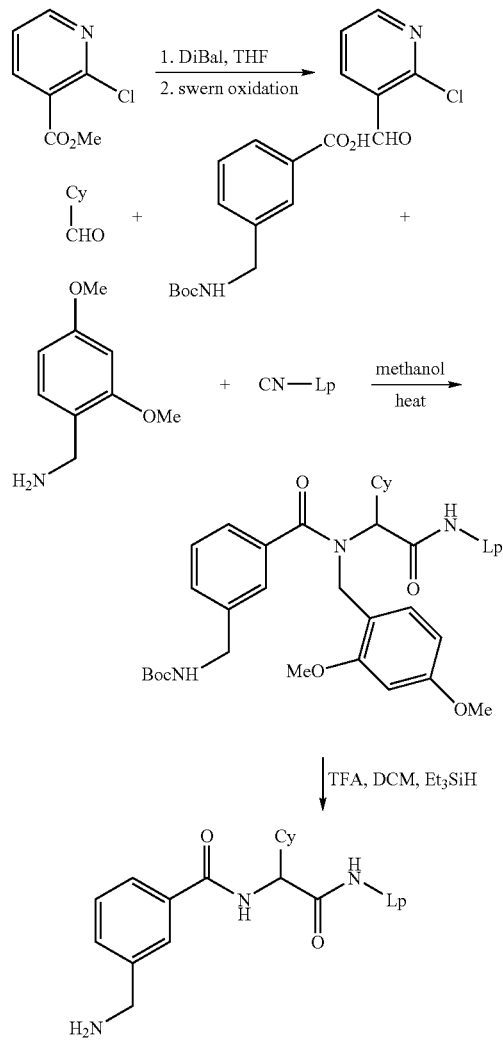
UgI Synthesis for Lp Groups with any Cy Group
Tetrahedron, 1999, 65, 7411
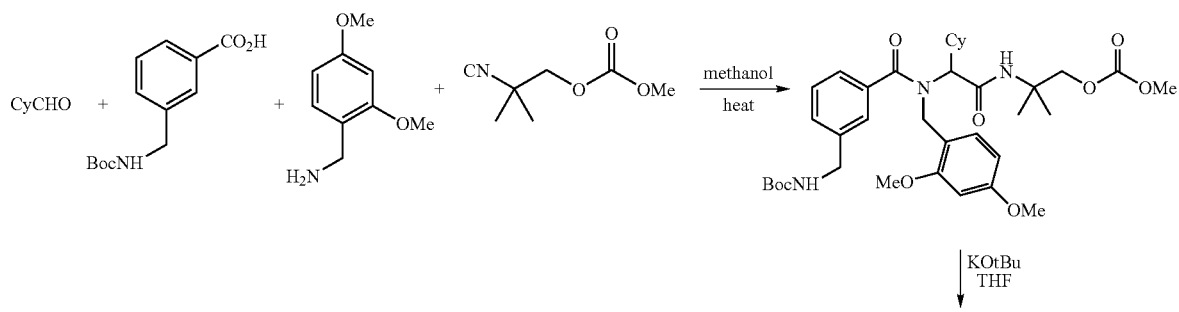

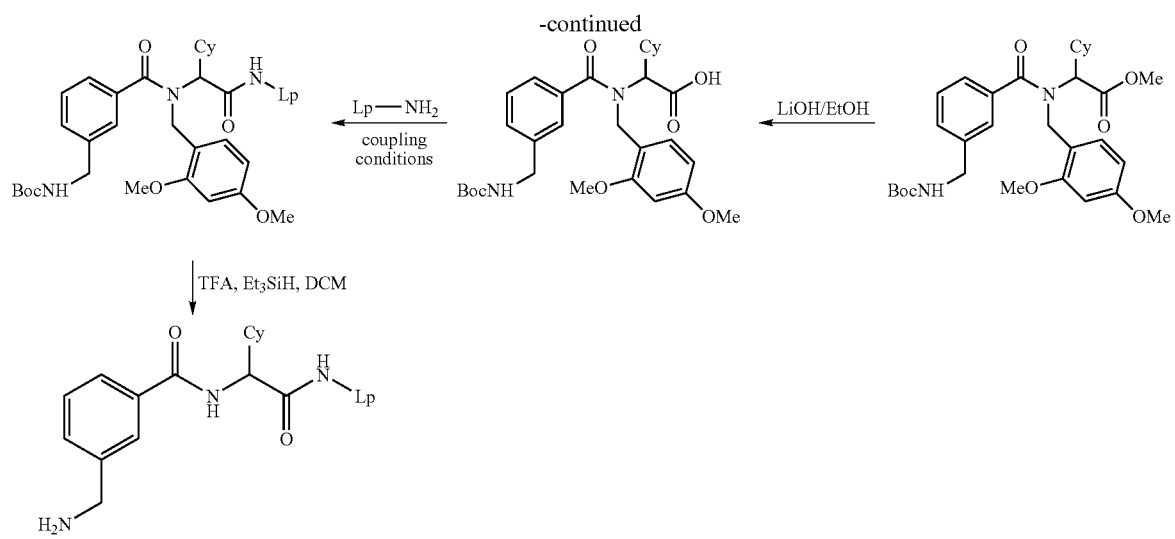
Synthesis of Aminothazolylglyine Used for Other 2-NH Linked Compounds
See Examples 30–32
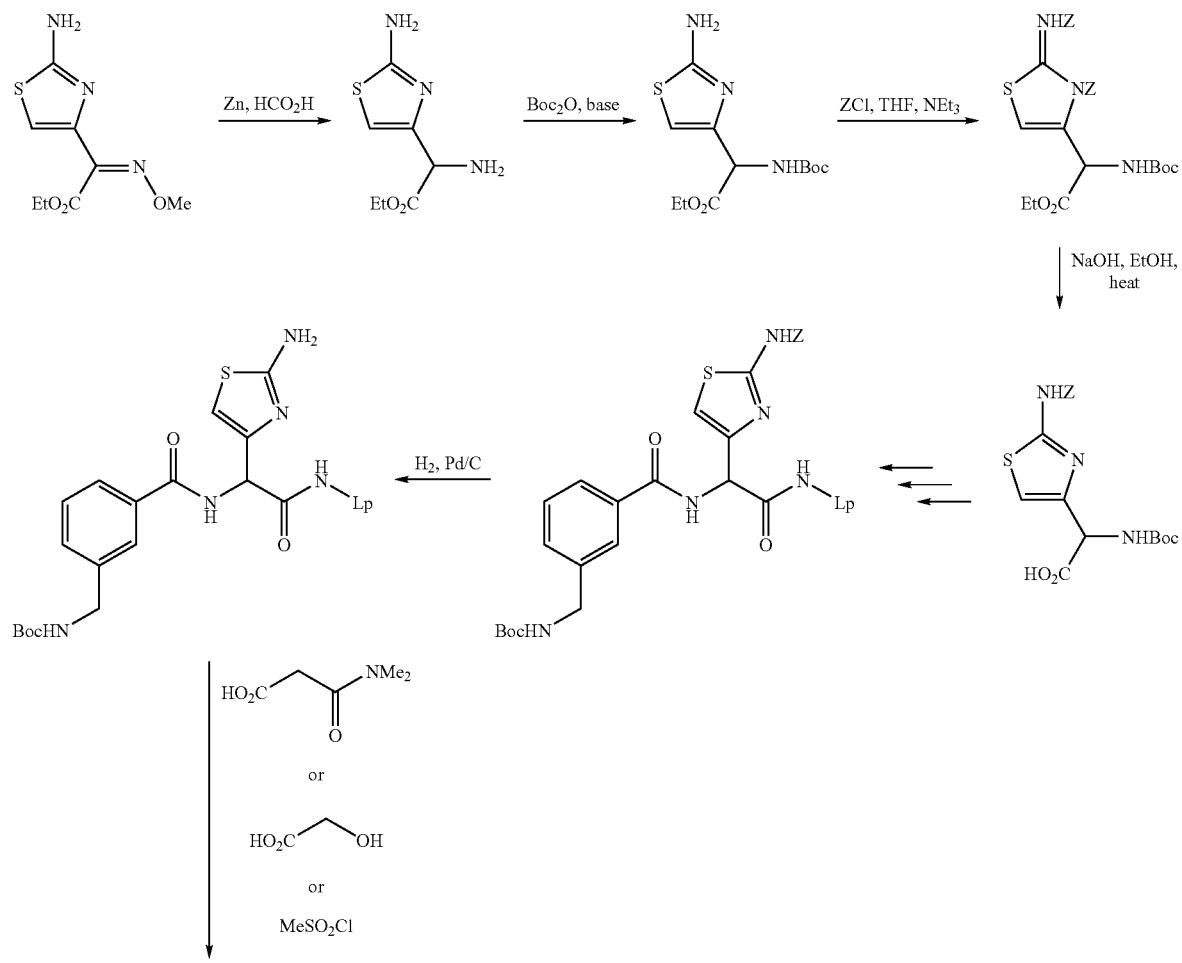

-continued

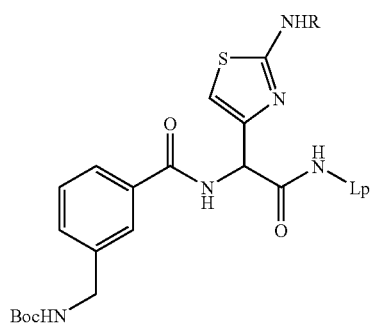

Compounds of Formula (I) Where Lp is a Tetrahydrobenzothiophene

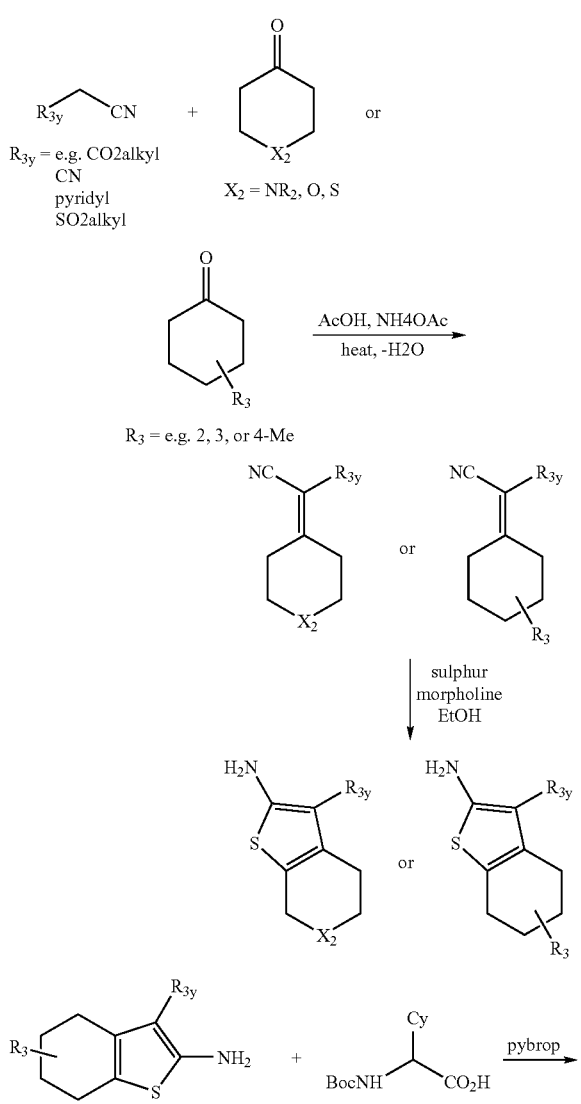

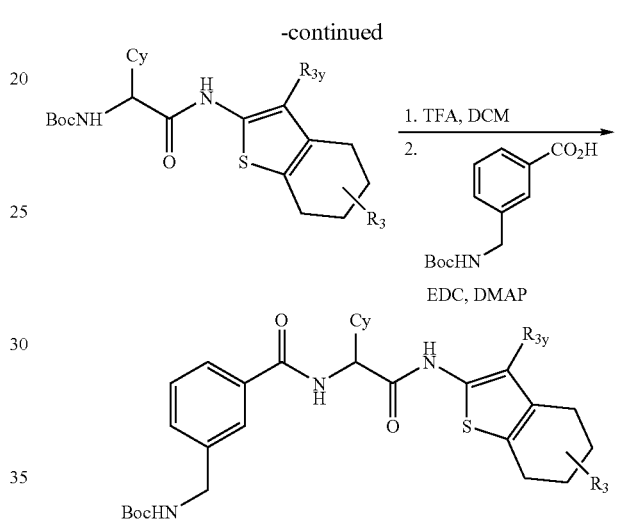

Thus viewed from a further aspect, the invention provides a process for the preparation of a compound according to the invention which process comprises coupling a lipophilic group to a compound of formula (VIII)

$R_2—(X)_2—CH(Cy)-Z_1$ (VIII)

or a protected derivative thereof (wherein $R_2$, X and Cy are as defined above and $Z_1$ is a reactive functional group).

Instead of introducing the group L-Lp as the final stage process step, the compounds of formula I may alternatively be prepared by a process in which the group $R_2$ is introduced in the final process step.

Thus viewed from another aspect the invention provides a process for the preparation of a compound according to the invention which process comprises reacting a compound of formula (IX)

$Z_2—CH(Cy)-L-Lp$ (IX)

(wherein Cy, L and Lp are as defined above and $Z_2$ is HX or a reactive functional group), or a protected derivative thereof, with a compound of formula (X)

$R_2—Z_3$ (X)

(wherein $R_2$ is as defined above and $Z_3$ is XH or an appropriate reactive group), or a protected derivative thereof, followed if necessary by the removal of any protecting groups.

Thus, for a compound of formula I in which X—X represents CONH, a compound of formula (IX) in which $Z_2$ is $H_2N$ may be reacted with a compounds of formula (X) in which $Z_3$ is COOH or a reactive derivative thereof, such as an acyl halide or an anhydride, for example as described in the Examples herein.

In another aspect the invention relates to a process for preparing a compound of formula I comprising deprotecting a compound of formula (I'):

$$R^{2'}—X—X—CH(Cy')-L-Lp \qquad (I')$$

wherein $R^{2'}$ is $R^2$ (as hereinabove defined) or protected $R^2$, Cy' is Cy (as hereinabove defined) or protected Cy and Lp' is Lp (as hereinabove defined) or protected Lp; providing at least one protecting group is present.

Compounds of formula (I') in which L represents CONH and X—X represents $CONR_{1a'}$ where $R_{1a'}$ is an optionally substituted benzyl group, such as 2,4-dimethoxybenzyl, may be prepared using Ugi methodology, starting from an aldehyde of formula CyCHO, an optionally substituted benzylamine of formula $R_{1a'}NH_2$, a nitrile of formula NC-Lp and an N-protected 3-aminomethylbenzoic acid, such as 3-BOC-aminomethylbenzoic acid. The protecting groups may be removed using trifluoroacetic acid. The procedure may be performed, for example, as described in Method 2 in the Experimental Section hereinafter.

If necessary physiologically tolerable salts can be formed using methods known in the art.

Where the lipophilic group Lp comprises more than one group, it may generally be formed by coupling these groups together at an appropriate stage in the preparation of the compound of formula I using conventional methods or as described in the Examples.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably the compositions will be sterile and in a solution or suspension form suitable for injection or infusion. Such compositions form a further aspect of the invention.

The following are examples of pharmaceutical compositions of compounds according to the invention.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets each containing 60 mg of active ingredient are made as follows:

|  |  |
| --- | --- |
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Viewed from this aspect the invention provides a pharmaceutical composition comprising a serine protease (tryptase) inhibitor according to the invention together with at least one pharmaceutically acceptable carrier or excipient. The pharmaceutical composition may also optionally comprise at least one further anti-inflammatory agent.

Viewed from a further aspect the invention provides the use of a tryptase inhibitor according to the invention for the manufacture of a medicament for use in a method of treatment of the human or non-human animal body (e.g. a mammalian, avian or reptilian body) to combat (i.e. treat or prevent) a condition responsive to said inhibitor, which comprises administering an effective amount of a compound according to the invention.

Viewed from a further aspect the invention provides a method of treatment of the human or non-human animal body (e.g. a mammalian, avian or reptilian body) to combat a condition responsive to a tryptase inhibitor.

The dosage of the inhibitor compound of the invention will depend upon the nature and severity of the condition being treated, the administration route and the size and species of the patient. However in general, quantities of from 0.01 to 100 μmol/kg bodyweight will be administered.

All publications referred to herein are hereby incorporated by reference.

The invention will now be described further with reference to the following non-limiting Examples.

Experimental:

Abbreviations used follow IUPAC-IUB nomenclature. Additional abbreviations are BOC, t-butyloxycarbonyl; HPLC, high performance liquid chromatography; LC, liquid chromatography; MS, mass spectrometry; Rt, retention time; NMR, nuclear magnetic resonance; DMF, dimethylformamide; Quant, quantitative; DMAP, dimethylaminopyridine; TFA, trifluoroacetic acid; Sat., saturated; Aq., aqueous; DCM, dichloromethane; PyBroP, bromo-tris-pyrrolidino-phosphonium hexafluorophosphate; Phg, phenylglycine; Chex, cyclohexyl; THF, tetrahydrofuran; DiBal, diisobutylaluminium hydride; KHMDS, potassium bis(trimethylsilyl)amide; Trisyl, tri-isopropylbenzene-sulphonyl; Z, benzyloxycarbonyl; and EDC, 1-(3-dimethylaminopropyl)-3-ethylcarbodiimide hydrochloride. Starting materials were purchased from Aldrich (Gillingham, UK), Lancaster (Morecambe, UK), Avocado (Heysham, UK), Maybridge (Tintagel, UK), Nova Biochem (Nottingham, UK) or Bachem.

Purification:

Flash column chromatography was carried out using Merck silica gel Si60 (40–63 μm, 230–400 mesh). Purification of final products was by crystallisation, flash column chromatography or gradient reverse phase HPLC on a Waters Deltaprep 4000 at a flow rate of 50 mL/minute using a Deltapak C18 radial compression column (40 mm×210 mm, 10–15 mm particle size). Eluant A consisted of aqueous trifluoroacetic acid (0.1%) and eluant B 90% acetonitrile in aqueous trifluoroacetic acid (0.1%) with gradient elution (Gradient, 0 minutes 5% B for 1 minutes, then 5% B to 20% B over 4 minutes, then 20% B to 60% B over 32 minutes). Fractions were analysed by analytical HPLC and LC/MS before pooling those with >95% purity for lyophilisation.

Analysis:

Proton nuclear magnetic resonance ($^1$H NMR) spectra were recorded on a Bruker DPX300 (300 MHz). Analytical HPLC's were performed on a Shimadzu LC6 gradient system equipped with an autosampler. Eluant A consisted of aqueous trifluoroacetic acid (0.1%) and eluant B consisted of 90% acetonitrile and 10% water, containing trifluoroacetic acid (0.1%). Gradient 1 elution began at 5% B and increased to 100% B over seven minutes. Gradient 2 elution began at 5% B and increased to 100% B over ten minutes. Gradient 3 elution began at 5% B for one minute, increasing to 20% B after the fourth minute, 40% B after the 14$^{th}$ minute and then 100% B after the 15$^{th}$ minute. The columns used were Luna 2 C18 (3μ, 30 mm×4.6 mm), Luna 2 C18 (5μ, 150 mm×2 mm) and a Symmetry Rp8 (3.5μ, 50×2.1 mm).

LC/MS were performed on a PESCIEX single quadrupole API-150EX instrument, equipped with a Luna 2 C18 column (3μ, 30 mm×4.6 mm) eluting with 20% to 100% acetonitrile in water over five minutes (gradient 4).

Method 1

3-(Aminomethyl)benzoyl-D-phenylglycine 2-aminobenzothiazol-6-amide bis(trifluoroacetate) salt.

2,6-Diaminobenzothiazole

2-Amino-6-nitrobenzothiazole (500 mg, 2.56 mmol) was dissolved in methanol (20 mL) and 10% palladium on carbon (50 mg) was added as a slurry in methanol (1 mL). The atmosphere was replaced with hydrogen and the suspension was stirred overnight. The catalyst was removed by suction filtration and the solvent evaporated to afford 2,6-diaminobenzothiazole (420 mg, 99%) as a pale yellow solid.

N-BOC-D-Phenylglycine 2-aminobenzothiazol-6-amid

N-BOC-D-Phenylglycine (250 mg, 1.0 mmol), 1-(3-dimethylaminopropyl)-3-ethylcarbodiimide hydrochloride (190 mg, 1.0 mmol) and 7-aza-1-hydroxybenzotriazole (140 mg, 1.0 mmol) were stirred in dimethylformamide (3 mL) for ten minutes. 2,6-Diaminobenzothiazole (160 mg, 1.0 mmol) was then added and the solution was stirred overnight at room temperature. Ethyl acetate (15 mL) was added and the solution was washed with water (5 mL), saturated citric acid solution (5 mL), saturated NaHCO$_3$ (5 mL) and water (5 mL), and dried over MgSO$_4$. The solvent was removed under reduced pressure to afford N-BOC-D-phenylglycine 2-aminobenzothiazol-6-amide.

$^1$H NMR (CDCl$_3$): 8.93 (1 H, br s, C(O)NHAr); 7.72 (1 H, s, benzothiazole C(7)H); 7.35 (2 H, br s, Ph); 7.23–7.05 (3 H, m, Ph); 6.93 (1 H, d, J=10 Hz, benzothiazole C(4)H or C(5)H); 6.72 (1 H, d, J=10 Hz, benzothiazole C(4)H or C(5)H); 6.05 (1 H, d, J=7 Hz, CHPh); 5.92 (2 H, br s, NH$_2$); 5.45 (1 H, br s, BOCNH); 1.27 (9 H, s, $^t$Bu).

D-Phenylglycine 2-aminobenzothiazol-6-amide

A solution of N-BOC-D-phenylglycine 2-aminobenzothiazol-6-amide in dichloromethane (5 mL) was treated with trifluoroacetic acid (5 mL) and stirred for 30 minutes. The dichloromethane and excess trifluoroacetic acid were removed under reduced pressure and the residue was triturated with diethyl ether to afford D-phenylglycine 2-aminobenzothiazol-6-amide as its trifluoroacetate salt (350 mg, 89%).

3-(Aminomethyl)benzoyl-D-phenylglycine 2-aminobenzothiazol-6-amide trifluoroacetate salt N-BOC-3-aminomethylbenzoic acid (250 mg, 1.0 mmol), 1-(3-dimethylaminopropyl)-3-ethylcarbodiimide hydrochloride (190 mg, 1.0 mmol) and 7-aza-1-hydroxybenzotriazole (140 mg, 1.0 mmol) were stirred in dimethylformamide (10 mL) for five minutes. D-Phenylglycine 2-aminobenzothiazol-6-amide trifluoroacetate salt (350 mg, 0.85 mmol) was then added and the mixture was stirred overnight. The solution was poured into ethyl acetate (20 mL) and washed with 5% HCl (5 mL), saturated NaHCO$_3$ (5 mL) and water (5 mL), dried over MgSO$_4$ and the solvent removed under reduced pressure. The crude product was purified by flash column chromatography on silica gel (60% ethyl acetate/40% hexane to 100% ethyl acetate) to afford 3-(N-BOC-aminomethyl)benzoyl-D-phenylglycine 2-aminobenzothiazol-6-amide. This was dissolved in dichloromethane (5 mL) and trifluoroacetic acid (5 mL) was added. The solution was stirred at room temperature for 30 minutes before the dichloromethane and excess trifluoroacetic acid were removed under reduced pressure. The residue was triturated with diethyl ether to afford 3-(aminomethyl)benzoyl-D-phenylglycine 2-aminobenzothiazol-6-amide as its trifluoroacetate salt (150 mg, 32%).

$^1$H NMR (d$_4$ MeOH): 8.21 ppm (1 H, s, benzothiazole C(7)H); 7.97 (1 H, s, aminomethylbenzoyl C(2)H); 7.94 (1 H, d, J=5 Hz, 3-(aminomethyl)benzoyl C(6)H); 7.80–7.48 (5 H, m, Ar); 7.47–7.32 (4 H, m, Ar); 5.81 (1 H, s, CHPh); 4.22 (2 H, s, CH$_2$NH$_2$). HPLC (Luna 2, Gradient 1): rt=2.80 minutes. LC/MS (Luna 2, Gradient 4): rt=1.40 minutes, 432 (MH)$^+$.

Examples 1–5 were synthesised in the same way as the compound of Method 1 using the indicated amino acid in place of phenylglycine and the indicated amine in place of 2,6-diaminobenzothiazole.

EXAMPLE 1

3-(Aminomethyl)benzoyl-D-cyclohexylglycine indan-5-amide trifluoroacetate salt

Prepared from N-BOC-D-cyclohexylglycine and 5-aminoindane.

$^1$H NMR (d$_4$ MeOH): 7.88–7.02 ppm (7 H, m, Ar); 4.43 (1 H, d, J=9 Hz, CH(cHex)); 4.04 (2 H, s, CH$_2$NH$_2$); 2.78–2.68 (4 H, m, indane C(1)H$_2$ and C(3)H$_2$); 2.04–1.82 (4 H, m, indane C(2)H$_2$ cHex CH$_2$); 1.77–1.56 (4 H, m, 2×cHex CH$_2$); 1.36–0.95 (5H, m, 2×cHex CH$_2$ and CH). HPLC (Luna 2, Gradient 1): rt=4.27 minutes. LCMS (Luna 2, Gradient 4): rt=2.21 minutes, 406 (MH)$^+$.

EXAMPLE 2

3-(Aminomethyl)benzoyl-D/L-1-naphthylglycine indan-5-amide trifluoroacetate salt Prepared from N-BOC-D/L-1-naphthylglycine and 5-aminoindan $^1$H NMR (d$_4$ MeOH): 8.25 ppm (1 H, d, J=7.2 Hz, Ar); 8.04–7.84 (4 H, m Ar); 7.75–7.44 (7 H, m, Ar); 7.33 (1 H, d, J=7.25 Hz, Ar); 7.16 (1 H, d, J=7.25 Hz, Ar); 6.72 (1 H, s, CHAr); 4.15 (2 H, s, CH$_2$NH$_2$); 2.94–2.78 (4 H, m, indane C(1)H$_2$C(3)H$_2$); 2.17–1.98 (2 H, m, indane C(2)H$_2$). HPLC (Luna 2, Gradient 1): rt=4.37 minutes. LCMS (Luna 2, Gradient 4): rt=2.37 minutes, 450 (MH)$^+$.

EXAMPLE 3

3-(Aminomethyl)benzoyl-D/L-piperidin-4-ylglycine indan-5-amide bis(trifluoroacetate) salt (N-BOC-Piperidin-4-ylidene)-(N-benzyloxycarbonyl)glycine methyl ester N-BOC-4-Piperidone (2.0 g, 10 mmol), N-(benzyloxycarbonyl)-α-phosphonoglycine trimethyl ester (3.64 g, 2.20 mmol) and 1,8-diazabicyclo[5.4.0]undec-7-ene (1.57 mL, 2.10 mmol) were stirred in acetonitrile overnight. The solvent was removed and the residue taken up in ethyl acetate (50 mL) and washed with water (2×10 mL), dried (MgSO$_4$) and evaporated under reduced pressure. The residual oil was purified by chromatography on silica gel (ethyl acetate/hexane, 40%/60%) to afford the unsaturated ester (3.63 g, 90%).

$^1$H NMR (CDCl$_3$): 7.36 ppm (5 H, br s, Ph); 6.05 (1 H, br s, NH); 5.12 (2 H, s, CH$_2$Ph); 3.73 (3 H, br s, OMe); 3.50 (4 H, br s, piperidine C(2)H$_2$ and C(6)H$_2$); 2.86 (2 H, br s, piperidine C(3) H$_2$ or C(5) H$_2$); 2.45–2.36 (2 H, m, piperidine C(3) H$_2$ or C(5) H$_2$); 1.47 (9 H, s, $^t$Bu).

(N-BOC-Piperidin-4-ylidene)-(N-benzyloxycarbonyl)glycine

A solution of the methyl ester (391 mg, 1 mmol) in tetrahydrofuran (10 mL) was treated with 1 M LiOH (2 mL, 2 mmol) and heated at reflux for 4 hours. The solvent was removed under reduced pressure and the residue diluted with water (20 mL). The aqueous solution was acidified to pH 4 with 5% aqueous HCl and extracted with ethyl acetate (3×20 mL). The combined organic extracts were dried (MgSO$_4$) and concentrated under reduced pressure to afford the acid as a brown solid (305 mg, 78%) which was carried forward without further purification.

(N-BOC-Piperidin-4-ylidene)-(N-benzyloxycarbonyl)glycine indan-5-amide

A solution of the acid (253 mg, 0.65 mmol) in dimethylformamide (20 mL) was treated with 1-(3-dimethylaminopropyl)-3-ethylcarbodiimide hydrochloride (124 mg, 0.65 mmol), 1-hydroxy-7-azabenzotriazole (88 mg, 0.65 mmol), 5-aminoindane (86 mg, 0.65 mmol) and 4-(N,N-dimethylamino)pyridine (10 mg) and stirred overnight at room temperature. The solution was partitioned between ethyl acetate (30 mL) and water (30 mL), separated, and the organic phase was washed with 5% aqueous HCl (30 mL), saturated aqueous NaHCO$_3$ (30 mL) and water (30 mL), dried (MgSO$_4$) and concentrated under reduced pressure to afford a colourless solid. The crude product was purified by flash chromatography (ethyl acetate/hexane 1:1) to afford the indanamide as a colourless solid (215 mg, 65%).

$^1$H NMR (CDCl$_3$): 8.31 (1 H, br s, NH); 7.43 (9 H, m, 8 Ar, NH); 5.01 (2 H, s, CH$_2$Ph); 3.34 (4 H, br s, piperidine C(2)H$_2$ and C(6)H$_2$); 2.83–2.71 (4 H, m, indane C(1)H$_2$ and C(3)H$_2$); 2.54 (2 H, br s, piperidine C(3)H$_2$ or C(5)H$_2$); 2.23–2.14 (2 H, m, piperidine C(3)H$_2$ or C(5)H$_2$); 2.05–1.92 (2 H, m, indane C(2)H$_2$); 1.38 (9 H, s, $^t$Bu).

D/L-(N-BOC-Piperidin-4-yl)glycine indan-5-amide

10% Palladium on carbon (50 mg) was added to a solution of the alkene (215 mg, 0.43 mmol) in ethanol (20 mL) and the suspension was stirred under a hydrogen atmosphere overnight. The mixture was filtered and the filtrand was washed with ethanol (20 ml) before the combined solvents were concentrated under reduced pressure to afford the deprotected saturated amine as a colourless oil (97 mg, 60%). The crude amine was carried forward without further purification.

The remaining steps of the synthesis are identical to those of the compound in method 1.

3-(Aminomethyl)benzoyl-D/L-piperidin-4-ylglycine indan-5-amide bis(trifluoroacetate) salt.

$^1$H NMR (d$_4$ MeOH): 8.04–7.92 ppm (2 H, m, Ar); 7.73–7.55 (2H, m, Ar); 7.49 (1 H, s, Ar); 7.32 (1 H, d, J=7.2 Hz, Ar); 7.18 (1 H, d, J=7.2 Hz, Ar); 4.68 (1 H, d, J=9 Hz, CH(Pip)); 4.21 (2 H, s, CH$_2$NH$_2$); 3.54–3.40 (2 H, m, piperidine C(2)H and C(6)H); 3.13–2.96 (2 H, m, piperidine C(2)H and C(6)H); 2.94–2.81 (4 H, m, indane C(1)H$_2$ and C(3)H$_2$); 2.41–2.23 (1 H, m, piperidine C(4)H); 2.20–1.95 (4H, m, indane C(2)H$_2$, piperidine C(3)H and C(4)H); 1.84–1.60 (2 H, m, piperidine C(3)H and C(4)H). HPLC (Luna 2, Gradient 1): rt=3.08 minutes. LCMS (Luna 2, Gradient 4): rt=1.27 minutes, 407 (MH)$^+$.

EXAMPLE 4

3-(Aminomethyl)benzoyl-D/L-2-(N-formylamino) thiazol-4-yl]glycine 5-indanamide trifluoroacetate salt Prepared from D/L-α-(N-$^t$butyloxycarbonyl)-[2-(N-formylamino)thiaz-4-yl]glycine (synthesised as described below) and 5-aminoindane.

Ethyl α-azido-[2-(N-formylamino)thiaz-4-yl]acetate

A solution of ethyl [2-(N-formylamino)thiaz-4-yl]acetate (1 g, 0.0047 mol) in THF (10 mL) was stirred under argon at −78° C. and potassium bis(trimethylsilyl)amide (2.8 g, 0.014 mol) in THF (10 mL) was added. After stirring for 30 minutes, 2,4,6-triisopropylbenzenesulfonyl azide (3.6 g, 0.012 mol) was added as a solid in one portion. After 5 minutes, acetic acid (1.4 mL, 0.018 mol) was added and the mixture warmed to room temperature. The reaction mixture was then partitioned between ethyl acetate (100 mL) and water (100 mL), separated and the organic layer dried (MgSO$_4$). Evaporation of the solvent and purification of the residue by silica gel chromatography afforded the azide (0.95 g, 80%).

$^1$H NMR (CDCl$_3$): 8.78 ppm (1 H, s, NHCHO); 6.98 (1 H, s, C(5)H); 5.95 (1 H, s, CHN$_3$); 4.18 (2 H, m, CH$_2$CH$_3$); 1.20 (3 H, m, CH$_2$CH$_3$).

Ethyl α-(N-$^t$butyloxycarbonylamino)-[2-(N-formylamino) thiaz-4-yl]acetate

Di-$^t$butyl dicarbonate (0.9 g, 0.004 mol) and 5% palladium on carbon (catalytic amount) were added to a solution of the azide (0.95 g, 0.0037 mol) in methanol (25 mL). The mixture was stirred at room temperature under an atmosphere of hydrogen for 8 hours. After this time the mixture was filtered through celite, washing through with methanol (25 mL). Evaporation of the solvent and purification of the residue by silica gel chromatography afforded the $^t$butyloxycarbonyl amine as a pale oily solid (1.1 g, 90%).

$^1$H NMR (CDCl$_3$): 8.53 ppm (1 H, s, NHC$\underline{H}$O); 6.89 (1 H, s, C(5)H); 6.18 (1 H, d, J=8 Hz, N$\underline{H}$Boc); 5.38 (1 H, d, J=8 Hz, C$\underline{H}$N); 4.06 (2 H, m, C$\underline{H}_2$CH$_3$); 1.28 (9 H, s, tBu); 1.12 (3 H, m, CH$_2$C$\underline{H}_3$).

D/L-α-N-$^t$butyloxycarbonyl-[2-(N-formylamino) thiaz-4-yl]glycine

A solution of the ester (1.1 g, 0.0031 g) in THF (25 mL) was treated with 1 M aqueous LiOH (5 ml, 0.005 mol) and heated at reflux for 1 hour. The solvent was removed under reduced pressure and the residue diluted with water (100 mL). The pH was reduced to 2 using 5% aqueous HCl and the aqueous phase was extracted with ethyl acetate (3×50 mL). The combined organic extracts were dried (MgSO$_4$) and concentrated under reduced pressure to afford the acid as a white solid (0.8 g, 84%).

$^1$H NMR (d$_4$ MeOH): 8.38 ppm (1 H, s, NHC$\underline{H}$O); 7.01(1 H, s, C(5)H); 5.21 (1 H, s, C$\underline{H}$N); 1.39 (9 H, s, $^t$Bu).

3-(Aminomethyl)benzoyl-D/L-[2-(formylamino)thiazol-4-yl]glycine 5-indanamide trifluoroacetate salt $^1$H NMR (d$_4$ MeOH): 10.10 ppm (1 H, s, N$\underline{H}$CHO); 8.80 (1 H, d, J=8 Hz, NH); 8.48 (1 H, s, NHC$\underline{H}$O); 7.97 (2 H, br s, Ar); 7.58 (2H, m, Ar); 7.42 (1 H, s, aminothiazole C(5)H); 7.37 (1 H, d, J=7 Hz, indane C(6)H); 7.18 (1 H, s, indane C(4)H); 7.10 (1 H, d, J=7 Hz, indane C(7)H); 5.92 (1 H, m, C$\underline{H}$Ar); 4.18 (2 H,s, C$\underline{H}_2$NH$_2$); 2.83 (4 H, m, indane C(1)H$_2$ and C(3)H$_2$); 2.02 (2 H, m, indane C(2)H$_2$) HPLC (Luna 2, gradient 1): rt=3.71 minutes. LC/MS (Luna 2, gradient 4): rt=2.05 minutes; 450 (MH)$^+$.

EXAMPLE 5

3-(Aminomethyl)benzoyl-D/L-2-aminothiazol-4-ylglycine-5-indanamide bis(hydrochloride) salt.

Prepared from D/L-α-N-$^t$butyloxycarbonyl-[2-(N-formylamino)thiaz-4-yl]glycine and synthesised using the method of Example 4 except that the final deprotection was effected using 3 M aqueous HCl in THF, in order to remove both the $^t$butyloxycarbonyl and formyl protecting groups.

$^1$H NMR (d$_4$ MeOH): 7.87 ppm (2 H, m, Ar); 7.51 (1 H, m, Ar); 7.48 (1 H, t, J=7 Hz, (aminomethyl)benzoyl C(3)H); 7.40 (1H, s, aminothiazole C(5)H); 7.20 (1 H, d, J=8 Hz, indane C(6)H); 7.05 (1 H, d, J=8 Hz, indane C(7)H); 6.73 (1 H, s, indane C(4)H); 5.78 (1 H, s, C$\underline{H}$Ar); 4.12 (2 H, s, C$\underline{H}_2$NH$_2$); 2.79 (4 H, m, indane C(1)H$_2$ and C(3)H$_2$); 2.00 (2 H, m, indane C(2)H$_2$). HPLC (Luna 2, gradient 1): rt=3.21 minutes. LC/MS (Luna 2, gradient 4): rt=1.78 minutes; 422 (MH)$^+$.

Method 2

3-(Aminomethyl)benzoyl-D/L-4-methylphenylglycine indan-5-amide hydrochloride salt.

N-Formyl-5-aminoindane.

To a solution of 5-aminoindane (7.53 g, 56.5 mmol) in DMF (100 mL) was added formic acid (2.2 mL, 58.3 mmol), 1-(3-dimethylaminopropyl)-3-ethylcarbodiimide hydrochloride (10.94 g, 57 mmol) and diisopropylethylamine (19.7 mL, 0.11 mol). The resulting solution was stirred overnight and then partitioned between saturated aqueous citric acid (100 mL) and ethyl acetate (200 mL). The organic layer was separated and washed with aqueous sodium bicarbonate solution (100 mL) and water (3×100 mL), then concentrated under reduced pressure to give the formamide as a thick oily solid (8.5 g, 93%)

Indan-5-isonitrile

To a solution of N-formyl-5-aminoindane (12 g, 74.5 mmol) in dichloromethane (100 mL) was added triethylamine (23 mL, 0.17 mol) and the solution was cooled to 0° C. under nitrogen. Phosphorous oxychloride (7 mL, 75 mmol) was added dropwise over 10 minutes, keeping the temperature at 0° C. The mixture was stirred at this temperature for 1 hour. A solution of sodium carbonate (15.6 g, 0.18 mol) in water (50 mL) was then added dropwise, keeping the temperature below 30° C. The mixture was diluted with water (100 mL) and then separated. The aqueous layer was extracted with dichloromethane (2×50 mL) and the combined organic extracts then washed with brine (200 mL), dried over magnesium sulphate and concentrated under reduced pressure. The crude oil was purified by vacuum distillation to give the product as a clear oil which solidified at low temperature (7.8 g, 72%); bp. 100–105° C. (0.05 mBar).

$^1$H NMR (CDCl$_3$): 7.10 (4 H, m, Ar); 2.82 (4 H, t, J=8 Hz, C(1)H$_2$, C(3)H$_2$); 2.03 (2 H, quintet, J=8 Hz, C(2)H$_2$).

3-(BOC-aminomethyl)benzoyl-D/L-N-(2,4-dimethoxybenzyl)-4-methylphenylglycine indan-5-amide.

A solution of p-tolualdehyde (168 mg, 1.4 mmol) and 2,4-dimethoxybenzylamine (207 μL, 230 mg, 1.4 mmol) in dichloromethane (1 mL) was allowed to stand overnight. The solution was diluted to 5 mL with dichloromethane and dried over magnesium sulfate. The solvent was decanted off, the solids rinsed with dichloromethane (2×1 mL) and the solution diluted further to 10 mL. 3-(N-BOC-aminomethyl) benzoic acid (350 mg, 1.4 mmol) and indane-5-isonitrile (4 mL of a 5 g/100 mL solution in dichloromethane, 200 mg, 1.4 mmol) were added. The solution was stirred under argon for 14 days before being evaporated under reduced pressure onto silica gel (5 g). Purification by Biotage Flash 40 chromatography, eluting with 2:1 to 1:1 hexane:ethyl acetate afforded 3-(BOC-aminomethyl)benzoyl-D/L-N-(2,4-dimethoxybenzyl)-4-methylphenylglycine indan-5-amide as a white foamy solid (297 mg, 32%)

3-(Aminomethyl)benzoyl-D/L-4-methylphenylglycine indan-5-amide hydrochloride salt.

A solution of 3-(BOC-aminomethyl)benzoyl-D/L-N-(2,4-dimethoxybenzyl)-4-methylphenylglycine indan-5-amide (290 mg, 0.43 mmol) in dichloromethane (3 mL) was stirred at room temperature and trifluoroacetic acid (3 mL) was added. After 90 minutes the excess trifluoroacetic acid and dichloromethane were removed under reduced pressure. The purple oily residue was taken up in methanol (2 mL) and purified by SCX acid ion-exchange chromatography, eluting with methanol and then 5%–10% 2 N NH$_3$/methanol in dichloromethane, to afford 3-(aminomethyl)benzoyl-D/L-4-methylphenylglycine indan-5-amide as its free base. This was taken up in acetonitrile (5 mL) and water (10 mL) was added, followed by 5% HCl (aq.) to afford a pale yellow solution. The acetonitrile was removed under reduced pressure and the aqueous solution was lyophilised to afford 3-(aminomethyl)benzoyl-D/L-4-methylphenylglycine indan-5-amide as its hydrochloride salt (92 mg, 0.20 mmol, 48%).

$^1$H NMR (CD$_3$CN): 8.47 ppm (1H, br s, Ar); 7.72 (1H, s, Ar); 7.67–7.53 (2 H, m, Ar); 7.46–7.28 (4 H, m, Ar); 7.13 (2 H, 35 d, J=10 Hz, tolyl C(2)H's or C(3)H's); 7.07 (1 H, d, J=10 Hz, indane C(6)H or C(7)H); 5.55 (1 H, s, C$\underline{H}$Tol);

3.74 (2 H, s, CH₂NH₂); 2.81 (2 H, t, J=6 Hz, indane C(1)H₂ or C(3)H₂); 2.77 (2 H, t, J=6 Hz, indane C(1)H₂ or C(3)H₂); 2.27 (3 H, s, CH₃Ar); 2.10–1.95 (2 H, m, indane C(2)H₂). HPLC (Luna 2, Gradient 1): rt=4.53 min. LC/MS (Luna 2, Gradient 4): rt=2.13 min, 414 (MH)⁺.

Examples 6–11 were synthesised in the same way as the compound of method 2 using the indicated aldehyde.

EXAMPLE 6

3-(Aminomethyl)benzoyl-D/L-6-methylpyridin-2-ylglycine indan-5-amide bis(hydrochloride) salt From 6-methylpyridine-2-carboxaldehyde.

¹H NMR (Free base, CDCl₃): 9.70 ppm (1 H, br s, NH-Indane); 8.27 (1 H, d, J=7 Hz, NHCHAr); 7.97 (1 H, s, Ar); 7.89 (1 H, d, J=9 Hz, Ar); 7.67–7.48 (4 H, m, Ar); 7.27–7.10 (4 H, m, Ar); 5.85 (1 H, d, J=7 Hz, CHPy); 4.00 (2 H, s, CH₂NH₂); 2.90 (2 H, t, J=7 Hz, indane C(1)H₂ or C(3)H₂); 2.88 (2 H, t, J=7 Hz, indane C(1)H₂ or C(3)H₂); 2.66 (3 H, s, CH₃Py); 2.09 (2 H, quintet, J=7 Hz, indane C(2)H₂); 1.64 (2 H, br s, NH₂). HPLC (Luna 2, Gradient 1): rt=3.28 min. LC/MS (Luna 2, Gradient 4): rt=2.05 min, 415 (MH)⁺.

EXAMPLE 7

3-(Aminomethyl)benzoyl-D/L-imidazol-4-ylglycine indan-5-amide bis(hydrochloride) salt From imidazole-4-carboxaldehyde.

¹H NMR (Free base, CDCl₃): 9.90 ppm (1 H, br s, NH-Indane); 8.39 (1 H, br s, NH); 7.83 (1 H, s, Ar); 7.72 (1 H, d, J=9 Hz, Ar); 7.40 (2 H, d, J=10 Hz, Ar); 7.36–7.25 (2 H, m, Ar); 7.24 (1 H, d, J=8 Hz, indane C(6)H or C(7)H); 7.04 (1H, d, J=8 Hz, indane C(6)H or C(7)H); 6.93 (1 H, s, Ar); 6.02 (1 H, br d, J=5 Hz, CH-Im); 3.78 (2 H, s, CH₂NH₂); 2.80 (2 H, t, J=7 Hz, indane C(1)H₂ or C(3)H₂); 2.78 (2 H, t, J=7 Hz, indane C(1)H₂ or C(3)H₂); 2.00 (2 H, quintet, J=7 Hz, indane C(2)H₂). HPLC (Luna 2, Gradient 1): rt=3.65 min. LC/MS (Luna 2, Gradient 4): rt=1.45 min, 390 (MH)⁺.

EXAMPLE 8

3-(Aminomethyl)benzoyl-D/L-1,3-benzodioxazol-5-ylglycine indan-5-amide hydrochloride salt From piperonal.

¹H NMR (Free base, CDCl₃): 9.32 ppm (1 H, br s, NH); 7.97 (1 H, d, J=9 Hz, Ar); 7.79 (1 H, s, Ar); 7.75 (1 H, d, J=10 Hz, Ar); 7.47 (1 H, d, J=8 Hz, Ar); 7.41–7.30 (2 H, m, Ar); 7.08–6.98 (2 H, m, Ar); 6.68 (1 H, d, J=10 Hz, Ar); 6.16 (1 H, d, J=8 Hz, CH–Np); 5.85 (2 H, d, J=11 Hz, OCH₂O); 3.84 (2 H, s, CH₂NH₂); 2.80 (2 H, t, J=7 Hz, indane C(1)H₂ or C(3)H₂); 2.76 (2 H, t, J=7 Hz, indane C(1)H₂ or C(3)H₂); 2.00 (2 H, quintet, J=7 Hz, indane C(2)H₂); 1.85 (2 H, br s, NH₂). HPLC (Luna 2, Gradient 4): rt=2.59 min. LC/MS (Luna 2, Gradient 4): rt=2.13 min, 444 (MH)⁺.

EXAMPLE 9

3-(Aminomethyl)benzoyl-D/L-5-methylfuran-2-ylglycine indan-5-amide hydrochloride salt From 5-methylfuran-2-carboxaldehyde.

¹H NMR (Free base, CDCl₃): 9.02 ppm (1 H, br s, NH); 7.78 (2 H, br s, NH and Ar); 7.65 (1 H, d, J=9 Hz, Ar); 7.39 (1 H, s, Ar); 7.37 (1 H, d, J=8 Hz, Ar); 7.28 (1 H, t, J=7 Hz, 3-aminomethylphenyl C(5)H); 7.19 (1 H, d, J=10 Hz, Ar); 7.00 (1 H, d, J=9 Hz, indane C(6)H or C(7)H); 6.29 (1 H, d, J=3 Hz, furyl C(3)H or C(4)H); 6.15 (1 H, d, J=8 Hz, CH-Fur); 5.79 (1 H, d, J=3 Hz, furyl C(3)H or C(4)H); 3.82 (2 H, s, CH₂NH₂); 2.75 (2 H, t, J=7 Hz, indane C(1)H₂ or C(3)H₂); 2.72 (2 H, t, J=7 Hz, indane C(1)H₂ or C(3)H₂); 2.40 (2 H, br s, NH₂); 2.10 (3 H, s, CH₃-Fur); 1.93 (2 H, quintet, J=7 Hz, indane C(2)H₂). HPLC (Luna 2, Gradient 1): rt=4.09 min. LC/MS (Luna 2, Gradient 4): rt=2.05 min, 404 (MH)⁺.

EXAMPLE 10

3-(Aminomethyl)benzoyl-D/L-benzofuran-2-ylglycine indan-5-amide hydrochloride salt From benzofuran-2-carboxaldehyde.

¹H NMR (Free base, CDCl₃): 9.27 ppm (1 H, br s, NH); 7.96 (1 H, d, J=8 Hz, NHCHAr); 7.72 (1 H, s, Ar); 7.66 (1 H, d, J=9 Hz, Ar); 7.40–7.23 (5 H, m, Ar); 7.18–7.04 (2 H, m, Ar); 6.97 (1 H, d, J=8 Hz, Ar); 6.92 (1 H, d, J=9 Hz, indane C(6)H or C(7)H); 6.76 (1 H, s, benzofuran C(3)H); 6.45 (1 H, d, J=8 Hz, CHAr); 3.76 (2 H, s, CH₂NH₂); 2.77–2.60 (4 H, m, indane C(1)H₂ and C(3)H₂); 2.10 (3 H, s, CH₃-Fur); 2.01–1.89 (2 H, m, indane C(2)H₂); 1.64 (2 H, br s, NH₂). HPLC (Luna 2, Gradient 1): rt=4.13 min. LC/MS (Luna 2, Gradient 4): rt=2.15 min, 440 (MH)⁺.

EXAMPLE 11

3-(Aminomethyl)benzoyl-D/L-3-methylbenzothiophen-2-ylglycine indan-5-amide hydrochloride salt From 3-methylbenzothiophene-2-carboxaldehyde.

¹H NMR (Free base, CDCl₃): 8.39 ppm (1 H, br s, NH); 7.74–7.62 (4 H, m, NH and Ar); 7.58 (1 H, d, J=8 Hz, Ar); 7.38 (1H, d, J=9 Hz, Ar); 7.35–7.23 (4 H, m, Ar); 7.09 (1 H, d, J=10 Hz, indane C(6)H or C(7)H); 6.99 (1 H, d, J=10 Hz, indane C(6)H or C(7)H); 6.40 (1 H, d, J=8 Hz, CHAr); 3.79 (2H, s, CH₂NH₂); 2.75 (2 H, t, J=6 Hz, indane C(1)H₂ or C(3)H₂); 2.73 (2 H, t, J=6 Hz, indane C(1)H₂ or C(3)H₂); 2.50 (3H, s, CH₃Ar); 2.00–1.88 (2 H, m, indane C(2)H₂); 1.55 (2H, br s, NH₂). HPLC (Luna 2, Gradient 1): rt=4.33 min. LC/MS (Luna 2, Gradient 4): rt=2.34 min, 470 (MH)⁺.

EXAMPLE 12

3-(Aminomethyl)benzoyl-D/L-2-phenylthiazol-4-ylglycine indan-5-amide trifluoroacetate salt Prepared in a similar manner to Example 1 using α-N-BOC-D/L-2-phenylthiazol-4-ylglycine (synthesised as described below) and 5-aminoindan.

Ethyl Oximinoacetoacetate.

This was prepared from ethyl acetoacetate (10.00 g) using the method of Fischer (*Organic Synthesis Coll. Vol. 3*, 513–516) to yield the titled compound (12.45 g).

¹H NMR (CDCl₃) 1.25 (3 H, t), 2.35 (3 H, s), 4.3 (2 H, q), 8.8 (1 H, br.).

Ethyl-γ-chloro-α-oximinoacetoacetate.

This was prepared from ethyl oximinoacetoacetate (1.73 g) using the method of Hatanaka et al. (*Journal of Medicinal Chemistry,* 1973, 16(9), 978–984) to yield the titled compound (1.44 g).

¹H NMR (CDCl₃) 1.25 (3 H, t), 4.3 (2 H, q), 4.55 (2 H, s), 9.45 (1 H, s), contains 20% starting material by NMR.

N-BOC-D/L-2-phenylthiazol-4-ylglycine.

A solution of ethyl γ-chloro-α-oximinoacetoacetate (2.10 g, 10.8 mmol) and thiobenzamide (1.49 g, 10.8 mmol) in dry benzene (15 mL) was heated to reflux. After 4 hours, the reaction mixture was poured onto NaHCO₃ (sat., aq., 50 mL); The resulting mixture was extracted with ethyl acetate (2×50 mL); and the combined extracts dried over MgSO₄ and evaporated under reduced pressure. Flash chromatography (ethyl acetate:hexane 1:4, $R_f$ 0.30) then afforded impure ethyl α-oximino-2-phenylthiazole-4-acetate (3.22 g). The crude oxime was then dissolved in methanol (15 mL) and formic acid (50% aq., 15 mL) was added. The mixture was cooled to 0° C. and zinc dust (2.00 g, 30.6 mmol) was added portionwise over 30 minutes. The reaction mixture was allowed to warm to room temperature, and stirred for 6 hours. The solution was then filtered, basified to pH 9 with solid NaHCO₃, and extracted with ethyl acetate (3×80 mL). The combined extracts were then dried and evaporated to afford D/L-2-phenylthiazol-4-ylglycine ethyl ester (1.43 g, 5.45 mmol, 50% from the chloro-oxime). The ester (194 mg, 0.74 mmol) was then dissolved in tetrahydrofuran (5 mL). Triethylamine (120 μL, 87 mg, 0.86 mmol) was added, followed by di-t-butyl dicarbonate (180 mg, 0.82 mmol). After stirring at room temperature for 4 days, water (20 mL) was added and the solution extracted with dichloromethane (2×20 mL). The combined extracts were evaporated and purified by flash column chromatography (ethyl acetate: hexane 1:4, $R_f$ 0.45) to afford N-t-butyloxycarbonyl-D/L-2-phenylthiazol-4-ylglycine ethyl ester (158 mg, 0.44 mmol, 59%) as a clear oil. The oil was dissolved in tetrahydrofuran (2 mL) and LiOH.H₂O (80 mg as a solution in 2 mL water) was added. After stirring at room temperature for 2 hours, water (10 mL) was added, and the solution extracted with ethyl acetate (5 mL). The aqueous layer was then acidified to pH 4 with 2N HCl, and extracted with ethyl acetate (2×20 mL); The latter extracts were combined and evaporated to afford N-BOC-D/L-2-phenylthiazol-4-ylglycine (116 mg, 0.35 mmol, 75%) as a white powder.

¹H NMR (CDCl₃): 10.81 (1 H, br s, CO₂H); 7.80–7.71 & 7.30–7.22 (2 H & 3 H, m, Ph); 7.21 (1 H, s, thiazole CH); 5.99 (1H, br d, J=6 Hz, NHBoc); 5.39 (1 H, br d, J=6 Hz, α-CH); 1.31 (9 H, s, C(CH₃)₃).

3-(Aminomethyl)benzoyl-D/L-2-phenylthiazol-4-ylglycine indan-5-amide trifluoroacetate salt.

¹H NMR (d₃ acetonitrile): 9.00 (1 H, s, NHAr); 8.15 (1 H, d, J=6 Hz, NHCH); 8.02 (1 H, s, Ar); 7.99–7.88 (2 H, m, Ar); 7.59–7.40 (7 H, m, Ar); 7.25 & 7.11 (2×1 H, 2×d, 2×J=7 Hz, indanyl CHCH); 6.01 (1 H, d, J=6 Hz); 4.15 (2 H, br s, CH₂NH₂); 2.90–2.79 (4 H, m, CH₂CH₂CH₂); 2.00 (2H, pentet, J=6 Hz, CH₂CH₂CH₂). HPLC (Luna 2, Gradient 1): rt=4.22 minutes. LC/MS (Luna 2, Gradient 4): rt=2.29 minutes, 483 (MH)⁺.

EXAMPLE 13

3-(Aminomethyl)benzoyl-D/L-(2-methylthiazol-4-yl)glycine indan-5-amide trifluoroacetate salt Synthesised as described for example 12 using N-BOC-D/L-2-methylthiazol-4-ylglycine, which was prepared in an analogous manner to N-BOC-D/L-2-phenylthiazol-4-ylglycine, except that thioacetamide was used in place of thiobenzamide, and 5-aminoindan.

¹H NMR (d₄ MeOH): 8.00 ppm (2 H, m, Ar); 7.8–7.57 (2 H, m, Ar); 7.48 (2 H, d, J=8 Hz, Ar); 7.30 (1 H, d, J=9 Hz, Ar); 7.16 (1 H, d, J=8 Hz, Ar); 6.01 (1 H, s, CHPh); 4.21 (2 H, s, CH₂NH₂); 2.90 (2 H, t, J=8 Hz, indane C(1)H₂ or C(3)H₂); 2.88 (2H, t, J=8 Hz, indane C(1)H₂ or C(3)H₂); 2.74 (3 H, s, Me); 2.10 (2 H, quintet, J=8 Hz, indane C(2)H₂). HPLC (Luna, Gradient 3): rt=5.92 (92%) LC/MS (Luna 2, Gradient 4): rt=1.88 minutes, 421 (MH)⁺.

EXAMPLE 14

3-(Aminomethyl)benzoyl-D/L-piperidin-4-ylglycine 4-isopropylanilide.

Prepared in a manner analogous to Example 3, except that 4-isopropylaniline was used in place of 5-aminoindane.

¹H NMR (d₄ methanol): 8.04–7.93 ppm (2 H, m, Ar); 7.73–7.50 (4 H, m, Ar); 7.20 (2 H, d, J=7.5 Hz, Ar); 4.67 (1 H, d, J=7.5 Hz, CH); 4.19 (2 H, s, CH₂NH₂); 3.56–3.41 (2 H, m, CH₂ pip); 3.12–2.97 (2 H, m, CH₂ pip); 2.87 (1 H, quintet, CH ipr); 2.44–2.26 (1 H, m, Ar); 2.22–1.98 (2 H, m, CH₂ pip); 1.87–1.58 (2 H, m, CH₂ pip); 1.28–1.21 (6 H, app. d, 2×CH₃). HPLC (Luna 2, Gradient 1): rt=2.18 minutes. LC/MS (Luna 2, Gradient 4): rt=1.37 minutes, 409 (MH)⁺.

EXAMPLE 15

3-(Aminomethyl)benzoyl-D/L-piperidin-4-ylglycine 1-acetyl-2,3-dihydroindol-6-amide bis(trifluoroacetate) salt Prepared in a manner analogous to Example 3 except that 1-acetyl-2,3-dihydroindol-6-amine was used in place of 5-aminoindane.

¹H NMR (d₆ DMSO): 8.65 ppm (1 H, br s, NH); 8.34–8.17 (3 H, m, NH); 8.00 (1 H, s, Ar); 7.93 (1 H, d, J=7.5 Hz, Ar); 7.63 (1 H, d, J=7.2 Hz, Ar); 7.55–7.46 (3 H, m, Ar); 7.15 (1 H, d, J=7.5 Hz, Ar); 4.58 (1 H, d, J=7.5 Hz, CH); 4.14–4.01 (4 H, m, CH₂NH₂, CH₂ indoline); 3.40–3.27 (2 H, m, CH₂ pip); 3.15–3.02 (2 H, m, CH₂ indoline); 2.96–2.73 (2 H, m, CH₂ pip); 2.16 (3 H, s, COCH₃); 2.02–1.89 (1 H, m, CH pip); 1.80–1.68 (1 H, m, CH pip); 1.64–1.33 (3 H, m, CH, CH₂ pip). HPLC (Luna 2, Gradient 1): rt=2.65 minutes. LC/MS (Luna 2, Gradient 4): rt=0.54 minutes, 450 (MH)⁺.

EXAMPLE 16

3-(Aminomethyl)benzoyl-D/L-piperidin-4-glycine 1-(aminoacetyl)-2,3-dihydroindol-6-amide tris(trifluoroacetate) salt Prepared in a manner analogous to Example 3 except that 1-(N-BOC-aminoacetyl)-2,3-dihydroindol-6-amine was used in place of 5-aminoindane.

¹H NMR (d₄ methanol): 8.46 ppm (1 H, s, Ar); 8.03–7.91 (2 H, m, Ar); 7.70 (1 H, d, J=7.2 Hz, Ar); 7.65–7.54 (1 H, m, Ar); 7.40 (1 H, d, J=7.5 Hz, Ar); 7.21 (1 H, d, J=7.5 Hz, Ar); 4.65 (1 H, d, J=7.5 Hz, CH); 4.21 (2H, s, C$\underline{H}_2$NH$_2$); 4.16–4.07 (2 H, m, CH$_2$ indoline); 4.02 (2 H, s, C$\underline{H}_2$NH$_2$); 3.55–3.40 (2 H, m, CH$_2$ pip); 3.28–3.17 (2 H, m, CH$_2$ indoline); 3.10–2.92 (2 H, m, CH$_2$ pip); 2.40–2.25 (1 H, m, CH pip); 2.23–1.93 (2 H, m, CH$_2$ pip); 1.86–1.60 (2 H, m, CH$_2$ pip). HPLC (Luna 2, Gradient 1): rt=2.03 minutes. LC/MS (Luna 2, Gradient 4): rt=0.64 minutes, 465 (MH)$^+$.

EXAMPLE 17

3-(Aminomethyl)benzoyl-D/L-1-acetylpiperidin-4-ylglycine indan-5-amide trifluoroacetate salt 3-(N-Z-Aminomethyl)benzoyl-D/L-1-BOC-piperidin-4-ylglycine indan-5-amide.

This compound was prepared in an analogous fashion to 3-(N-BOC-aminomethyl)benzoyl-D/L-(N-BOC-piperidin-4-yl)glycine indan-5-amide, an intermediate in the synthesis of Example 3, except that 3-(N-Z-aminomethyl)benzoic acid was used in the final coupling reaction.

3-(N-Z-Aminomethyl)benzoyl-D/L-1-acetylpiperidin-4-ylglycine indan-5-amide.

A solution of 3-(N-Z-aminomethyl)benzoyl-D/L-1-BOC-piperidin-4-ylglycine indan-5-amide(65 mg, 0.1 mmol) in dichloromethane (3 mL) was stirred at room temperature and trifluoroacetic acid (2 mL) was added. Stirring was continued for an hour and the solvents were removed under reduced pressure. The residue was taken up in dichloromethane (5 mL) and treated with triethylamine (0.055 mL, 0.4 mmol) and acetyl chloride (0.014 mL, 0.2 mmol) and allowed to stir for 1 hour. The solution was washed with water (3×5 mL), dried (MgSO$_4$) and concentrated under reduced pressure. The residue was purified by flash chromatography using methanol/dichloromethane (1:9) as eluent to afford a colourless solid (45 mg, 78%).

$^1$H NMR (d$_4$ methanol): 7.82–7.68 ppm (2 H, m, Ar); 7.51–7.20 (9 H, m, Ar); 7.16 (1 H, d, J=7.2 Hz, Ar); 5.09 (2 H, s, OCH$_2$Ph); 4.65–4.47 (2 H, m, CH and NH); 4.31 (2 H, s, C$\underline{H}_2$NH$_2$); 4.00–3.85 (1 H, m, CH pip); 3.14–2.97 (1 H, m, CH pip); 2.92–2.77 (4 H, m, 2×CH$_2$ indane); 2.66–2.48 (1 H, m, CH pip); 2.32–2.17 (1 H, m, CH pip); 2.15–1.90 (6 H, m, COCH$_3$, CH$_2$ ind, CH pip); 1.85–1.67 (1 H, m, CH pip); 1.53–1.20 (2 H, m, CH$_2$ pip).

3-(Aminomethyl)benzoyl-D/L-1-acetylpiperidin-4-ylglycine indan-5-amide trifluoroacetate salt.

10% Palladium on carbon (20 mg) was added to a solution of 3-(N-Carbobenzyloxy-aminomethyl)benzoyl-D/L-1-acetylpiperidin-4-ylglycine indan-5-amide (45 mg, 0.08 mmol) in methanol (20 mL) and the suspension was stirred under a hydrogen atmosphere overnight. The mixture was filtered and the filter was washed with methanol (20 mL). The combined filtrates were concentrated under reduced pressure and the amine was purified by flash chromatography using methanol/dichloromethane (1:9) as eluent to afford a colourless solid. Trifluoroacetic acid (1 mL) was added and the solution was concentrated under reduced pressure to give the TFA salt (16 mg, 36%).

$^1$H NMR (d$_4$ methanol): 7.98–7.87 ppm (2 H, m, Ar); 7.73–7.20 (4 H, m, Ar); 7.10 (1 H, d, J=7.2 Hz, Ar); 4.55 (1 H, s, CH); 4.15 (2 H, s, C$\underline{H}_2$NH$_2$); 4.00–3.82 (2 H, m, CH$_2$ pip); 3.15–2.95 (1 H, m, CH pip); 2.89–2.71 (4 H, m, 2×CH$_2$ indane); 2.66–2.48 (1H, m, CH pip); 2.29–2.11 (1H, m, CH pip); 2.10–1.85 (6H, m, COCH$_3$, CH$_2$ ind, CH pip); 1.81–1.62 (1H, m, CH pip); 1.50–1.19 (2H, m, CH$_2$pip). HPLC (Luna 2, Gradient 1): rt=3.64 minutes. LC/MS (Luna2, Gradient 4): rt=1.75 minutes, 449 (MH)$^+$.

Examples 18–20 were prepared in a manner analogous to Example 17, except that the indicated carboxylic acid derivative was used to form the amide of the piperidine nitrogen, under appropriate conditions.

EXAMPLE 18

3-(Aminomethyl)benzoyl-D/L-(1-propanoyl)piperidin-4-ylglycine indan-5-amide trifluoroacetate salt From propanoyl chloride.

$^1$H NMR (d$_4$ methanol): 7.80 ppm (2H, s, Ar); 7.59–7.41 (2H, m, Ar); 7.36 (1H, s, Ar); 7.16 (1H, d, J=7.2 Hz, Ar); 7.03 (1 H, d, J=7.2 Hz, Ar); 4.53–4.39 (2 H, m, CH, CH pip); 4.04 (2 H, s, C$\underline{H}_2$NH$_2$); 3.07–2.90 (1 H, m, CH pip); 2.86–2.70 (4 H, m, 2×CH$_2$ ind); 2.61–2.43 (1 H, m, CH pip); 2.36–2.22 (2 H, m, COC$\underline{H}_2$CH$_3$); 2.19–2.04 (1 H, m, CH pip); 2.01–1.79 (3 H, m, CH$_2$ ind, CH pip); 1.76–1.60 (1 H, m, CH pip); 1.41–1.10 (2 H, m, CH$_2$ pip); 0.93 (3 H, t, J=7.5 Hz, COCH$_2$C$\underline{H}_3$). HPLC (Luna 2, Gradient 1): rt=3.54 minutes. LC/MS (Luna 2, Gradient 4): rt=1.96 minutes, 463 (MH)$^+$.

EXAMPLE 19

3-(Aminomethyl)benzoyl-D/L-(1-isobutyryl)piperidin-4-ylglycine indan-5-amide

From isobutyryl chloride.

$^1$H NMR (d$_4$ methanol): 7.75 ppm (1 H, s, Ar); 7.67 (1 H, d, J=7.2 Hz, Ar); 7.42 (1 H, d, J=7.2 Hz, Ar); 7.38–7.29 (2 H, m, Ar); 7.18 (1 H, d, J=7.5 Hz, Ar); 7.03 (1 H, d, J=7.5 Hz, Ar); 4.57–4.41 (1 H, m, CH); 4.09–3.95 (1 H, m, CH pip); 3.81 (2 H, s, C$\underline{H}_2$NH$_2$); 3.10–2.94 (1 H, m, CH pip); 2.91–2.67 (5 H, m, CH ipr, 2×CH$_2$ ind); 2.62–2.43 (1 H, m, CH pip); 2.25–2.07 (1 H, m, CH pip); 2.04–1.59 (4 H, m, CH$_2$ ind, 2×CH pip); 1.43–1.12 (2 H, m, CH$_2$ pip); 0.98 (6 H, m, 2×CH$_3$). HPLC (Luna 2, Gradient 1): rt=3.39 minutes. LC/MS (Luna 2, Gradient 4): rt=1.88 minutes, 477 (MH)$^+$.

EXAMPLE 20

3-(Aminomethyl)benzoyl-D/L-(1-aminoacetyl)piperidin-4-ylglycine indan-5-amide bis(trifluoroacetate) salt From N-BOC-glycine.

$^1$H NMR (d$_4$ methanol): 7.94–7.81 ppm (2 H, m, Ar); 7.58 (1 H, d, J=7.2 Hz, Ar); 7.54–7.44 (1 H, m, Ar); 7.38 (1 H, s, Ar); 7.20 (1 H, d, J=7.5 Hz, Ar); 7.08 (1 H, d, J=7.2 Hz, Ar); 4.54–4.40 (1 H, m, CH); 4.10 (2 H, s, C$\underline{H}_2$NH$_2$); 3.95–3.76 (2 H, m, COC$\underline{H}_2$NH$_2$); 3.74–3.65 (1 H, m, CH pip); 3.12–2.96 (1 H, m, CH pip); 2.84–2.58 (5 H, m, 2×CH$_2$ ind, CH pip); 2.26–2.07 (1 H, m, CH pip); 2.04–1.84 (3 H, m, CH$_2$ ind, CH pip); 1.79–1.69 (1 H, m, CH pip); 1.53–1.04 (2 H, m, CH$_2$ pip). HPLC (Luna 2, Gradient 1): rt=2.65 minutes. LC/MS (Luna 2, Gradient 4): rt=1.35 minutes, 464 (MH)$^+$.

EXAMPLE 21

3-(Aminomethyl)benzoyl-D/L-indan-5-ylglycine indan-5-amide trifluoroacetate salt Indan-5-carboxylic acid A solution of 5-acetylindane (2.0 g, 12.5 mmol) in 1,4-dioxane (20 mL) was stirred at room temperature. Sodium hydroxide (5.0 g, 125 mmol) in water (20 mL) was then added, followed by enough of a solution of potassium hydroxide and iodine in water (20 g KOH, 10 g $I_2$, 50 mL $H_2O$) to give a permanent iodine colour (~10 mL). The mixture was heated at 60° C. for 1.5 hours when further $I_2$ and KOH solution (5 mL) was added and heating was continued for a further 16 hours. The solution was cooled, poured into water (150 mL) and extracted with diethyl ether (3×25 mL). The aqueous solution was then made acidic with 6 N HCl, causing a brown oil to separate. This was extracted into ethyl acetate (3×50 mL), which was dried ($MgSO_4$) and evaporated to afford the crude acid as a brown solid (1.41 g, 70%).

Methyl indan-5-carboxylate

A solution of the crude acid (1.41 g, 8.7 mmol) in methanol (25 mL) was cooled under Ar to 0° C. Thionyl chloride (0.76 mL, 1.24 g, 10.4 mmol) was added by syringe and the solution was stirred for 48 hours, warming slowly to room temperature. The methanol was evaporated, the residue was partitioned between ethyl acetate (100 mL) and water (50 mL) and $NaHCO_3$ (s) was added until gas evolution ceased. The layers were separated, the aqueous phase was extracted with ethyl acetate (2×30 mL) and the combined organics were washed with water (30 mL), saturated $NH_4Cl$ (aq., 30 mL), water (30 mL) and brine (30 mL) and dried over $MgSO_4$. Evaporation of the solvent afforded a dark brown oil, which was purified by flash column chromatography (silica gel, 10% EtOAc/Hexane eluent) to afford the ester as a pale yellow low-melting solid (490 mg, 32%).

5-(Hydroxymethyl)indane

A solution of the ester (480 mg, 2.7 mmol) in THF (30 mL) was cooled under Ar to 0° C. and DIBAL-H (1M in toluene, 6.8 mL, 6.8 mmol) was added by syringe. The solution was stirred overnight, warming to room temperature. No starting material was indicated by tlc, so the solution was cooled back to 0° C. and quenched by adding $Na_2SO_4.10H_2O$ (s, ~2 g) and stirring vigorously for two hours. The mixture was diluted with ethyl acetate (25 mL) and filtered, rinsing the solid well with ethyl acetate. Evaporation of the solvent afforded the alcohol as a pale yellow solid (375 mg, 93%).

Indan-5-carboxaldehyde

A solution of the alcohol (370 mg, 2.5 mmol) in dichloromethane (10 mL) was stirred at room temperature. N-Methylmorpholine-N-oxide (307 mg, 2.62 mmol) and powdered 4 Å molecular sieves (~1 g) were added and the mixture was stirred under Ar for 30 minutes. Tetrapropylammonium perruthenate (44 mg, 0.12 mmol) was added in one portion and stirring was continued for 30 minutes. Tlc indicated some starting material remaining, so further N-methylmorpholine-N-oxide (100 mg, 0.85 mmol) was added and stirring continued for an additional 30 minutes. The mixture was evaporated onto $SiO_2$ (~2 g) and purified by flash column chromatography ($SiO_2$, 10% EtOH/Hexane eluent) to afford the aldehyde as a pale yellow oil (299 mg, 82%).

3-(BOC-Aminomethyl)benzoyl-D/L-N-(2,4-dimethoxybenzyl)indan-5-ylglycine indan-5-amide.

The aldehyde (208 mg, 1.4 mmol) and 2,4-dimethoxybenzylamine (215 □L, 238 mg, 1.4 mmol) were mixed in dichloromethane (2 mL) and allowed to stand for an hour. The solution was diluted up to 5 mL, dried over $Na_2SO_4$ and added to 3-(BOC-aminomethyl)benzoic acid (360 mg, 1.4 mmol). A solution of indan-5-isonitrile (0.29 M in $CH_2Cl_2$, 5 mL, 1.4 mmol) was then added and the mixture allowed to stir for 26 days at room temperature. The solvent was evaporated onto $SiO_2$ (~5 g) and purified by Biotage Flash 40 chromatography, eluting with hexane/ethyl acetate (2:1 to 1:1) to afford the protected amide as a pale yellow foamy solid (385 mg, 40%).

3-(BOC-Aminomethyl)benzoyl-D/L-indan-5-ylglycine indan-5-amide trifluoroacetate salt.

A solution of the protected amide (385 mg, 0.55 mmol) and triethylsilane (180 μL, 130 mg, 1.1 mmol) in dichloromethane (5 mL) was stirred at room temperature and trifluoroacetic acid (5 mL) was added. After 1.5 hours the dichloromethane and excess trifluoroacetic acid were evaporated and the residue was purified by SCX ion exchange chromatography, eluting with 5% 2 N $NH_3$/MeOH in DCM, to afford the free amine as a pale yellow glassy solid. This was taken up in methanol (30 mL) and trifluoroacetic acid (5 drops) was added. The methanol and excess trifluoroacetic acid were evaporated and the residue taken up in water and lyophyllised to afford the amine trifluoroacetate salt as an off-white powder (178 mg, 58%).

$^1$H NMR ($d_6$ DMSO): 10.15 ppm (1 H, s, NH); 8.70 (1 H, d, J=9 Hz, NH); 8.09 (3 H, br s, $NH_3^+$); 7.95 (1 H, s, Ar); 7.88 (1 H, d, J=10 Hz, Ar); 7.53 (1 H, d, J=9 Hz, Ar); 7.50–7.38 (2H, m, Ar); 7.31 (1 H, s, Ar); 7.24–7.17 (2 H, m, Ar); 7.11 (1 H, d, J=9 Hz); 7.03 (1 H, d, J=9 Hz, Ar); 5.68 (1 H, d, J=8 Hz, CHPh); 4.00 (2 H, br s, $CH_2NH_3^+$); 2.82–2.58 (8 H, m, 2×indane $C(1)H_2$ and $C(3)H_2$); 1.98–1.80 (4 H, m, 2×indane $C(2)H_2$). HPLC (Luna 2, Gradient 2): rt=2.83 min. LCMS (Luna 2, Gradient 4): rt=2.37 min, 440 $(MH)^+$.

EXAMPLE 22

3-(Aminomethyl)benzoyl-D/L-6-amino-3-pyridylglycine indan-5-amide bis(hydrochloride) salt Prepared in a similar manner to Example 21, using 6-(N-BOC-amino)pyridine-3-carboxaldehyde, synthesised as described below.

Methyl 6-aminonicotinate

A suspension of 6-aminonicotinic acid (2.0 g, 14.5 mmol) and sulfuric acid (2 mL) in methanol (125 mL) was heated at reflux overnight. The solution was cooled, the methanol evaporated and the residue was taken up in water (100 mL) and made basic with $NaHCO_3$ (s), causing a white solid to precipitate. The mixture was extracted with chloroform (3×40 mL) and the combined extracts were dried ($MgSO_4$) and evaporated to afford the ester as an off-white solid (1.04 g, 30%).

Methyl 6-(N-BOC-amino)nicotinate

A solution of the amine (1.0 g, 6.6 mmol) in dichloromethane (50 mL) was stirred at room temperature and 4-N,N-dimethylaminopyridine (40 mg, 0.33 mmol), di-t-butyl-dicarbonate (1.51 g, 6.9 mmol) and triethylamine (970 □L, 700 mg, 6.9 mmol) were added. The solution was stirred for two hours before the dichlormethane was evaporated and the oily residue was purified by flash column chromatography ($SiO_2$, 20% ethyl acetate/hexane eluent) to afford the protected amine as a white crystalline solid (1.6 g, quantitative).

6-(N-BOC-Amino)-3-(hydroxymethyl)pyridine

A solution of the ester (1.36 g, 5.4 mmol) in dry THF (90 mL) was cooled to 0° C. under Ar. DIBAL-H (1 M in toluene, 11.3 mL, 11.3 mmol) was added by syringe and the solution was stirred for 1.5 hours. Tlc indicated that starting material was still present, so further DIBAL-H solution (6 mL) was added, and again after an additional two hours. After a further hour the reaction was quenched by the addition of $Na_2SO_4.10H_2O$ (s, ~3 g) at 0° C., and stirred vigorously. The mixture was diluted with diethyl ether (80 mL) and filtered, rinsing well with diethyl ether. Evaporation of the solvents afforded the alcohol as a white solid (1.20 g, 98%).

6-(N-BOC-Amino)pyridine-3-carboxaldehyde

A solution of the alcohol (780 mg, 3.5 mmol) in dichloromethane (40 mL) was stirred at room temperature and powdered 4 Å molecular sieves (~1 g) and N-methylmorpholine-N-oxide (510 mg, 4.35 mmol) were added. After thirty minutes tetrapropylammonium perruthenate (61 mg, 0.17 mmol) was added and stirring continued at room temperature. Further N-methylmorpholine-N-oxide (500 mg) and tetrapropylammonium perruthenate (50 mg) had to be added before the reaction went to completion, after stirring overnight. The mixture was filtered through a short silica pad, eluting with 2:1 hexane/ethyl acetate. Evaporation of the solvents afforded the aldehyde as an off-white solid (524 mg, 68%).

3-(Aminomethyl)benzoyl-D/L-6-amino-3-pyridylglycine indan-5-amide bis(hydrochloride) salt $^1$H NMR ($D_2O$): 7.97–7.84 ppm (2 H, m, Ar); 7.75 (2 H, s, Ar); 7.57 (1 H, d, J=8 Hz, Ar); 7.53–7.42 (1 H, m, Ar); 7.28–7.12 (2 H, m, Ar); 7.06 (1 H, d, J=10 Hz, Ar); 6.95 (1 H, d, J=11 Hz, Ar); 5.56 (1 H, s, C$\underline{H}$Py); 4.09 (2 H, C$\underline{H}_2$NH$_2$); 2.80–2.68 (4 H, m, indane C(1)H$_2$ and C(3)H$_2$); 1.90 (2 H, pentet, J=8 Hz, indane C(2)H$_2$). HPLC (Luna 2, Gradient 2): rt=3.27 min. LCMS (Luna 2, Gradient 4): rt=1.63 min, 416 (MH)$^+$.

EXAMPLE 23

3-(Aminomethyl)benzoyl-D/L-2-chloro-3-pyridylglycine indan-5-amide bis(hydrochloride) salt Prepared in a similar manner to Example 21, using 2-chloropyridine-3-carboxaldehyde, synthesised as described below.

Methyl 2-chloronicotinate

A solution of 2-chloronicotinic acid (1.61 g, 10.2 mmol) and sulfuric acid (0.5 mL) in methanol (30 mL) was stirred at reflux overnight. The solution was poured into water (100 mL) and neutralised with NaHCO$_3$ (s) before being extracted with 1:1 hexane/ethyl acetate (3×40 mL). The solvents were dried (MgSO$_4$) and evaporated and the residue was purified by flash column chromatography (SiO$_2$, 25% ethyl acetate/hexane eluent) to afford the ester as a colourless oil (700 mg, 40%).

2-Chloro-3-(hydroxymethyl)pyridine

A solution of the ester (460 mg, 2.45 mmol) in dry THF (25 mL) was stirred at 0° C. under Ar. A solution of DIBAL-H in toluene (1M, 5.2 mL, 5.2 mmol) was added by syringe, the solution was stirred for 1.5 hours and then further DIBAL-H (1.2 mL) was added and stirring continued overnight allowing the temperature to rise to ambient. The solution was then cooled back to 0° C. and quenched by adding Na2SO4.10 H$_2$O (s, ~2 g) and stirring vigorously for 30 minutes. The mixture was diluted with ethyl acetate (20 mL) and filtered, rinsing the solid well with further ethyl acetate. Evaporation of the solvents afforded the alcohol as a viscous pale yellow oil (360 mg, quant.) which was used without further purification.

2-Chloropyridine-3-carboxaldehyde

A solution of the alcohol (350 mg, 2.45 mmol) in dichloromethane (20 mL) was stirred at room temperature and and powdered 4 Å molecular sieves (~1 g) and N-methylmorpholine-N-oxide (500 mg, 3.68 mmol) were added. After thirty minutes tetrapropylammonium perruthenate (43 mg, 0.12 mmol) was added and stirring continued at room temperature for one hour. The mixture was filtered through a short silica pad, eluting with 1:1 hexane/ethyl acetate. Evaporation of the solvents afforded the aldehyde as a pale yellow solid (236 mg, 68%).

3-(Aminomethyl)benzoyl-D/L-2-chloro-3-pyridylglycine indan-5-amide bis(hydrochloride) salt $^1$H NMR ($D_2O$): 8.18 ppm (1H, d, J=3 Hz, Pyridine C(6)H); 7.82 (1H, d, J=10 Hz, Ar); 7.66 (2H, s, Ar); 7.49 (1H, d, J=10 Hz, Ar); 7.45–7.36 (1H, m, Ar); 7.35–7.28 (1H, m, Pyridine C(5)H); 7.18–7.05 (2H, m, Ar); 6.96 (1H, d, J=9 Hz, Ar); 5.95 (1H, s, C$\underline{H}$Ph); 4.06 (2H, s, C$\underline{H}_2$NH$_2$); 2.65 (4H, br s, indane C(1)H$_2$ and C(3)H$_2$); 1.78 (2H, pentet, J=8 Hz, indane C(2)H$_2$). HPLC (Luna 2, Gradient 2): rt=3.84 min. LCMS (Luna 2, Gradient 4): rt=1.97 min, 435 (MH)$^+$.

EXAMPLE 24

3-(Aminomethyl)benzoyl-D/L-indol-5-ylglycine indan-5-amide trifluoroacetate salt Prepared from N-BOC-indole-5-carboxaldehyde in a similar manner to example 21. The aldehyde was synthesised from methyl indole-5-carboxylate by appropriate protection and functional group manipulation as described for example 22.

$^1$H NMR (CDCl$_3$—free base): 8.32 ppm (1H, d, J=8 Hz, NH); 7.88–7.62 (4H, m, Ar and NH); 7.47–7.26 (5H, m, Ar and NH); 7.15 (1H, s, Ar); 7.13–6.99 (2H, m, Ar); 6.44 (1H, s, Ar); 5.91 (1H, t, J=6 Hz, indole C(2)H); 4.38 (1H, s, C$\underline{H}$Ar); 3.80 (2H, s, C$\underline{H}_2$NH$_2$); 2.76 (4H, t, J=7 Hz, indane C(1)H$_2$ and C(3)H$_2$); 2.00–1.88 (2H, m, indane C(2)H$_2$); 1.65 (2H, br s, NH$_2$). HPLC (Luna 2, Gradient 2): rt=4.09 min. LCMS (Luna 2, Gradient 4): rt=2.12 min, 439 (MH)$^+$.

EXAMPLE 25

3-(Aminomethyl)benzoyl-D/L-2,3-dihydrobenzofuran-5-ylglycine indan-5-amide Hydrochloride salt Prepared using method 2 from commercially available 2,3-dihydrobenzofuran-5-carboxaldehyde.

$^1$H NMR (CDCl$_3$—free base): 9.14 ppm (1H, s, NH); 7.91 (1H, d, J=8 Hz, NH); 7.84 (1H, s, Ar); 7.80 (1H, d, J=8 Hz, Ar); 7.52 (1H, d, J=7 Hz, Ar); 7.48–7.31 (3H, m, Ar); 7.23 (1H, d, J=9 Hz, Ar); 7.08 (1H, d, J=9 Hz, Ar); 6.72 (1H, d, J=9 Hz, Ar); 6.20 (1H, d, J=8 Hz, C$\underline{H}$Ar); 4.54 (2H, t, J=11 Hz, dihydrobenzofuran C(2)H$_2$); 3.92 (2H, s, C$\underline{H}_2$NH$_2$); 3.16–2.98 (2H, m, dihydrobenzofuran C(3)H$_2$); 2.92–2.80 (4H, m, indane C(1)H$_2$ and C(3)H$_2$); 2.07 (2H, pentet, J=8 Hz, indane C(2)H$_2$); 1.66 (2H, br s, NH$_2$). HPLC (Luna 2, Gradient 2): rt=4.13 min. LCMS (Luna 2, Gradient 4): rt=2.00 min, 442 (MH)$^+$.

EXAMPLE 26

3-(Aminomethyl)benzoyl-D/L-2-benzylthiazol-4-ylglycine indan-5-amide trifluoroacetate salt Synthesised as described for example 12 using N-BOC-D/L-2-benzylthiazol-4-ylglycine (which was prepared in an analogous manner to N-BOC-D/L-2-phenylthiazol-4-ylglycine, except that thiobenzylamide was used in place of thiobenzamide) and 5-aminoindane.

$^1$H NMR ($d_3$ acetonitrile): 9.17 (1H, br s, NH); 8.26 (1H, d, J=8 Hz, Ar); 8.08 (1H, s, Ar); 7.91 (1H, d, J=8 Hz, Ar); 7.62 (1H, d, J=8 Hz, Ar); 7.52 (1H, t, J=8 Hz, Ar); 7.43 (1H, s, Ar); 7.4–7.26 (5H, m, Ar); 7.23 (1H, d, J=8 Hz, Ar); 7.15 (1H, d, J=8 Hz, Ar); 5.94 (1H, d, J=7 Hz, CH-thiazole), 4.32 (2H, s, CH$_2$Ph); 4.19 (2H, s, CH$_2$NH$_2$); 2.87 (4H, m, CH$_2$CH$_2$CH$_2$); 2.07 (2H, pentet, J=5 Hz, CH$_2$CH$_2$CH$_2$)—Hplc (Luna 2, Gradient 1): rt=4.67 minutes. LC/MS (Luna 2, Gradient 4): rt=2.40 minutes, 497 (MH)$^+$.

EXAMPLE 27

3-(Aminomethyl)benzoyl-D/L-2-ethylthiazol-4-ylglycine indan-5-amide trifluoroacetate salt Synthesised as described for example 12 using N-BOC-D/L-2-ethylthiazol-4-ylglycine (which was prepared as described below) and 5-aminoindane.

N-t-butyloxycarbonyl-DL-2-ethylthiazol-4-ylglycine

A solution of ethyl γ-chloro-α-oximinoacetoacetate (2.00 g, 10.3 mmol) and thiopropionamide (0.92 g, 10.3 mmol) in dry benzene (15 mL) was heated to reflux. After 4 hours, the reaction mixture was poured onto NaHCO$_3$ (sat. aq., 50 mL), The resulting mixture was extracted with ethyl acetate (2×50 mL), and the combined extracts dried over MgSO$_4$ and evaporated under reduced pressure. Flash chromatography (ethyl acetate:hexane 1:4) then afforded impure ethyl α-oximino-2-ethylthiazole-4-acetate (0.83 g). The crude oxime was then dissolved in methanol (25 mL) and formic acid (50% aq., 10 mL) was added. The mixture was cooled to 0° C. and zinc dust (1.00 g, 15.3 mmol) was added portionwise over 30 mins. The reaction mixture was allowed to warm to room temperature, and stirred for 6 hours. The solution was then filtered, basified to pH 9 with solid NaHCO$_3$, and extracted with ethyl acetate (3×80 mL). The combined extracts were then dried and evaporated to afford DL-2-ethylthiazol-4-ylglycine ethyl ester (0.56 g, 2.6 mmol). The ester (560 mg, 2.6 mmol) was then dissolved in tetrahydrofuran (50 mL). Triethylamine (0.4 mL, 3.9 mmol) was added, followed by di-t-butyl dicarbonate (0.57 g, 2.6 mmol). After stirring at room temperature overnight the mixture was concentrated, water (20 mL) was added and the solution extracted with ethyl acetate (2×20 mL). The combined extracts were evaporated to afford N-t-butyloxycarbonyl-D/L-2-ethylthiazol-4-ylglycine ethyl ester (824 mg,) as a golden oil. The oil was dissolved in methanol (25 mL) and aqueous sodium hydroxide (2 M, 5 mL) was added. After stirring at room temperature for 2 hours, the solution was concentrated, water (30 mL) was added, and the solution extracted with ethyl acetate (30 mL). The aqueous layer was then acidified to pH 4 with 2 N HCl, and extracted with ethyl acetate (2×20 mL), The latter extracts were combined and evaporated to afford N-t-butyloxycarbonyl-D/L-2-ethylthiazol-4-ylglycine (450 mg) as a white solid.

$^1$H NMR (CDCl$_3$): 10.1 (1H, br s, CO$_2$H), 7.20 (1H, s, thiazole CH), 5.85 (1H, br d, J=6 Hz, NHBoc), 5.52 (1H, br d, J=6 Hz, α-CH), 3.05 (2H, q, J=5 Hz, CH$_2$CH$_3$), 1.49 (9H, s, C(CH$_3$)$_3$), 1.42 (3H, t, J=5 Hz, CH$_2$CH$_3$).

3-(Aminomethyl)benzoyl-D/L-2-ethylthiazol-4-ylglycine indan-5-amide trifluoroacetate salt $^1$H NMR (d$_4$ MeOH): 8.0 (2H, d, Ar); 7.68 (1H, d, J=8 Hz, Ar); 7.60 (1H, t, J=8 Hz, Ar); 7.50 (2H, s, Ar); 7.30 (1H, d, J=8 Hz, Ar); 7.15 (1H, d, J=8 Hz, Ar); 6.00 (1H, s, CH-thiazole); 4.2 (2H, s, CH$_2$NH$_2$); 3.07 (2H, q, J=6 Hz, CH$_2$CH$_3$); 2.88 (4H, m, CH$_2$CH$_2$CH$_2$); 2.09 (2H, pentet, J=6 Hz, CH$_2$CH$_2$CH$_2$); 1.40 (3H, t, J=6 Hz, CH$_2$CH$_3$). Hplc (Luna 2, Gradient 1): rt=4.15 minutes. LC/MS (Luna 2, Gradient 4): rt=2.07 minutes, 435 (MH)$^+$.

EXAMPLE 28

3-(Aminomethyl)benzoyl-D/L-2-methylthiazol-4-ylglycine 1-acetyl-2,3-dihydroindol-6-amide trifluoroacetate salt Synthesised as described for example 12 using N-BOC-D/L-2-methylthiazol-4-ylglycine (which was prepared in an analogous manner to N-BOC-D/L-2-phenylthiazol-4-ylglycine, except that thioacetamide was used in place of thiobenzamide) and N-acetyl-6-aminoindoline.

$^1$H NMR (d$_4$ MeOH): 8.3 (1H, m. Ar); 8.01 (2H, m, Ar); 7.68 (1H, d, J=9 Hz, Ar); 7.62 (1H, t, J=9 Hz, Ar); 7.51 (1H, s, Ar); 7.45 (1H, d, J=9 Hz, Ar); 7.19 (1H, d, J=9 Hz, Ar); 6.00 (1H, s, CH-thiazole); 4.21 (2H, s, CH$_2$NH$_2$); 4.17 (2H, t, J=6 Hz, CH$_2$indoline); 3.18 (2H, t, J=6 Hz, CH$_2$indoline); 2.73 (3H, s, thiazole-CH$_3$); 2.25 (3H, s, COCH$_3$). Hplc (Luna 2, Gradient 1): rt=3.14 minutes. LC/MS (Luna 2, Gradient 4): rt=1.67 minutes, 464 (MH)$^+$.

EXAMPLE 29

3-(Aminomethyl)benzoyl-D/L-2-methylthiazol-4-ylglycine 2,3-dihydroindol-6-amide bis(trifluoroacetate) salt Synthesised as described for example 12 using N-BOC-D/L-2-methylthiazol-4-ylglycine (which was prepared in an analogous manner to N-BOC-D/L-2-phenylthiazol-4-ylglycine, except that thioacetamide was used in place of thiobenzamide) and 6-aminoindoline using suitable protecting group strategy.

$^1$H NMR (d$_4$ MeOH): 7.9 (2H, br s, Ar); 7.78 (1H, s, Ar); 7.58 (1H, d, J=8 Hz, Ar); 7.52 (1H, t, J=8 Hz, Ar); 7.38 (1H, s, Ar); 7.26 (2H, 5, Ar); 5.88 (1H, s, CH-thiazole); 4.11 (2H, s, CH$_2$NH$_2$); 3.69 (2H, t, J=7 Hz, CH$_2$indoline); 3.15 (2H, t, J=7 Hz, CH$_2$indoline); 2.62 (3H, s, thiazole-CH$_3$). Hplc (Luna 2, Gradient 1): rt=2.358 minutes. LC/MS (Luna 2, Gradient 4): rt=1.19 minutes, 422 (MH)$^+$.

EXAMPLE 30

3-(Aminomethyl)benzoyl-D/L-2-(dimethylaminoacetylamino)thiazol-4-ylglycine indan-5-amide bis (trifluoroacetate) salt 3-(N-BOC-aminomethyl)benzoyl-D/L-2-aminothiazol-4-ylglycine 5-indanamide To a stirred solution of N-Boc-D/L-(2-Z-amino-4-thiazoyl)glycine (the amine was prepared by the method of Hardy, K.; Harrington, F. and Stachulski, A., *J. Chem. Soc. Perkin Trans I* (1984) 1227–1235 and then protected using standard conditions) (1.0 g, 2.45 mmol), 1-[3-(dimethylamino)propyl]-3-ethylcarbodiimide hydrochloride (565 mg, 2.95 mmol), 1-hydroxy-7-azabenzotriazole (401 mg, 2.95 mmol) and DMAP (cat) in dimethylformamide (10 mL) was added a solution of 5-aminoindane (393 mg, 2.65 mmol) in dimethylformamide (10 mL) and the mixture was stirred overnight. The dimethylformamide was evaporated under reduced pressure, and the resulting oil partitioned between water (50 mL) and ethyl acetate (50 mL). The ethyl acetate layer was washed with 5% hydrochloric acid (10 mL), saturated sodium bicarbonate solution (10 mL), dried ($MgSO_4$) and evaporated under reduced pressure to give a brown foam (1.0 g). The foam was dissolved up in acetic acid (27 mL), and to this stirred solution was added 30% HBr/acetic acid(13.5 mL), then heated at 60° C. for 4 hours. The solvent was then evaporated and the residue partitioned between ethyl acetate (30 mL) and $NaHCO_3$ (sat. aq., 20 mL). The ethyl acetate layer was then washed with water (20 mL) and brine (20 mL). The dried ($MgSO_4$) ethyl acetate layer was evaporated in vacuo to give a brown gum (490 mg).

The brown gum was dissolved in dichloromethane (20 mL) and treated with trifluoroacetic acid (5 mL) for 2 hours. The mixture was then evaporated in vacuo to give an oil. The oil, dissolved in dimethylformamide (10 mL), was then added to a stirred solution of 3-(N-BOC-aminomethyl)benzoic acid (480 mg, 1.91 mmol), 1-[3-(dimethylamino)propyl]-3-ethylcarbodiimide hydrochloride (441 mg, 2.3 mmol), 1-hydroxy-7-azabenzotriazole (313 mg, 2.3 mmol) and triethylamine (0.70 mL, 5 mmol) in dimethylformamide (15 mL) and the solution allowed to stir for 2.5 hours. The dimethylformamide was evaporated under reduced pressure, and the resulting oil partitioned between water (50 mL) and ethyl acetate (50 mL). The ethyl acetate layer was washed with 5% hydrochloric acid (10 mL), and $NaHCO_3$ (sat. aq., 10 mL), dried ($MgSO_4$) and evaporated under reduced pressure. The residue was absorbed onto silica and purified by column chromatography, eluting with 30–50% ethyl acetate/hexane. The desired fractions were combined and evaporated to give the amine as a light brown foam (270 mg).

$^1$H NMR ($d_6$ DMSO): 10.2 (1H, s, NH-indane); 8.62 (1H, d, J=8 Hz, NHCH-thiazole); 7.77 (2H, m, Ar); 7.55 (1H, s, Ar); 7.43 (2H, t, J=6 Hz, NHBoc); 7.40 (1H, d, J=9 Hz, Ar); 7.30 (1H, d, J=9 Hz, Ar); 7.13 (1H, d, J=9 Hz, Ar); 7.03 (2H, s, $NH_2$); 6.48 (1H, s, Ar); 5.67 (1H, s, CH-thiazole); 4.18 (2H, d, J=6 Hz, $CH_2NH_2$); 2.80 (4H, m, J=7 Hz, $CH_2CH_2CH_2$); 2.00 (2H, pentet, J=7 Hz, $CH_2CH_2CH_2$); 1.38 (9H, s, $C(CH_3)_3$).

3-(Aminomethyl)benzoyl-D/L-2-(dimethylamino-acetylamino)thiazol-4-ylglycine indan-5-amide A solution of the amine (154 mg, 0.30 mmol) in dimethylformamide (10 mL) was added to a stirred solution of N,N-dimethylglycine (56 mg, 0.54 mmol), 1-[3-(dimethylamino)propyl]-3-ethylcarbodiimide hydrochloride (86 mg, 0.45 mmol), 1-hydroxy-7-azabenzotriazole (80 mg, 0.59 mmol) and DMAP (cat) in dimethylformamide (15 mL) and allowed to stir for 24 hours. Further 1-[3-(dimethylamino)propyl]-3-ethylcarbodiimide hydrochloride (29 mg, 0.15 mmol) and 1-hydroxy-7-azabenzotriazole (20 mg, 0.15 mmol) were added and the solution was heated at 50° C. for 6 days. The mixture was cooled, the solvent evaporated under reduced pressure, and the residue dissolved in dichloromethane (10 ml). The stirred solution was then treated with trifluoroacetic acid (1 mL). After 2 hours the dichloromethane and excess trifluoroacetic acid were evaporated under reduced pressure and the residue purified by preparative hplc to afford the title compound as a white solid.

$^1$H NMR ($d_4$ MeOH): 8.02 (2H, d, J=8 Hz, Ar); 7.72–7.58 (2H, m, Ar); 7.50 (1H, s, Ar); 7.32 (2H, m, Ar); 7.17 (1H, d, J=8 Hz, Ar); 6.01 (1H, s, CH-thiazole); 4.28 (2H, s, $CH_2NMe_2$); 4.21 (2H, s, $CH_2NH_2$); 3.04 (6H, s, $CH_2NMe_2$); 2.90 (4H, m, $CH_2CH_2CH_2$); 2.10 (2H, pentet, J=6 Hz, $CH_2CH_2CH_2$). Hplc (Luna 2, Gradient 1): rt=3.40 minutes. LC/MS (Luna 2, Gradient 4): rt=1.47 minutes, 507 (MH)$^+$.

Examples 31 and 32 were synthesised in the same way as example 30 but using the indicated reagent in place of N,N-dimethylglycine.

EXAMPLE 31

3-(Aminomethyl)benzoyl-D/L-2-(hydroxyacetylamino)thiazol-4-ylglycine indan-5-amide Prepared using acetoxyacetic acid and appropriate deprotection conditions.

$^1$H NMR ($d_4$ MeOH): 8.37 (1H, s, Ar); 8.13 (1H, d, J=8 Hz, Ar); 8.02 (1H, d, J=8 Hz, Ar); 7.60 (1H, m, Ar); 7.38 (2H, s, Ar); 7.18 (1H, d, J=8 Hz, Ar); 7.07 (1H, m, Ar); 5.85 (1H, s, CH-thiazole); 4.15 (2H, s, $CH_2NH_2$); 2.78 (4H, m, $CH_2CH_2CH_2$); 1.95 (2H, pentet, J=7 Hz, $CH_2CH_2CH_2$). Hplc (Luna 2, Gradient 1): rt=4.55 minutes. LC/MS (Luna 2, Gradient 4): rt=3.04 minutes, 479 (M$^+$).

EXAMPLE 32

3-(Aminomethyl)benzoyl-D/L-2-(methanesulfonylamino)thiazol-4-ylglycine indan-5-amide Prepared using methanesulphonyl chloride $^1$H NMR ($d_4$ MeOH): 7.77 (2H, m. Ar); 7.48–7.32 (2H, m, Ar); 7.26 (1H, s, Ar); 7.08 (2H, d, J=8 Hz, Ar); 6.95 (1H, d, J=8 Hz, Ar); 6.58 (1H, s, Ar); 5.61 (1H, s, CH-thiazole); 3.98 (2H, s, $CH_2NH_2$); 2.78 (3H, s, $SO_2Me$); 2.65 (4H, m, $CH_2CH_2CH_2$); 1.85 (2H, pentet, J=5 Hz, $CH_2CH_2CH_2$). Hplc (Luna 2, Gradient 1): rt=3.76 minutes. LC/MS (Luna 2, Gradient 4): rt=1.89 minutes, 500 (MH)$^+$.

EXAMPLE 33

3-(Aminomethyl)benzoyl-D/L-2-ethylthiazol-4-ylglycine 3-ethoxycarbonyl-4,5,6,7-tetrahydrobenzo[b]thiophene-2-amide trifluoroacetate salt Synthesised as described for example 12 using N-BOC-D/L-2-ethylthiazol-4-ylglycine (which was prepared as described below) and 2-amino-3-ethoxycarbonyl-4,5,6,7-tetrahydro[b]thiophene.

N-t-butyloxycarbonyl-D/L-2-ethylthiazol-4-ylglycine

A solution of ethyl γ-chloro-α-oximinoacetoacetate (2.00 g, 10.3 mmol) and thiopropionamide (0.92 g, 10.3 mmol) in dry benzene (15 mL) was heated at reflux. After 4 hours the reaction mixture was poured onto $NaHCO_3$ (sat. aq., 50 mL), The resulting mixture was extracted with ethyl acetate (2×50 mL), and the combined extracts dried over $MgSO_4$ and evaporated under reduced pressure. Flash chromatography (ethyl acetate:hexane 1:4) then afforded impure ethyl α-oximino-2-ethylthiazole-4-acetate (0.83 g). The crude oxime was dissolved in methanol (25 mL) and formic acid (50% aq., 10 mL) was added. The mixture was cooled to 0° C. and zinc dust (1.00 g, 15.3 mmol) was added in portions over 30 mins. The reaction mixture was allowed to warm to room temperature and stirred for 6 hours. The solution was then filtered, basified to pH 9 with solid $NaHCO_3$, and extracted with ethyl acetate (3×80 mL). The combined extracts were dried ($MgSO_4$) and evaporated to afford D/L-2-ethylthiazol-4-ylglycine ethyl ester (0.56 g, 2.6 mmol). The ester (560 mg, 2.6 mmol) was dissolved in tetrahydrofuran (50 mL).

Triethylamine (0.4 mL, 3.9 mmol) was added, followed by di-t-butyl dicarbonate (0.57 g, 2.6 mmol). After stirring at room temperature overnight the mixture was concentrated, water (20 mL) was added and the solution extracted with ethyl acetate (2×20 mL). The combined extracts were evaporated to afford N-t-butyloxycarbonyl-D/L-2-ethylthiazol-4-ylglycine ethyl ester (824 mg,) as a golden oil. The oil was dissolved in methanol (25 mL) and sodium hydroxide (2 M aq., 5 mL) was added. After stirring at room temperature for 2 hours, the solution was concentrated, water (30 mL) was added, and the solution extracted with ethyl acetate (30 mL). The aqueous layer was then acidified to pH 4 with 2 N HCl, and extracted with ethyl acetate (2×20 mL), The latter extracts were combined and evaporated to afford N-t-butyloxycarbonyl-D/L-2-ethylthiazol-4-ylglycine (450 mg) as a white solid.

$^1$H NMR (CDCl$_3$): 10.1 (1H, br s, CO$_2$H), 7.20 (1H, s, thiazole CH), 5.85 (1H, br d, J=6 Hz, NHBoc), 5.52 (1H, br d, J=6 Hz, α-CH), 3.05 (2H, q, J=5 Hz, CH$_2$CH$_3$), 1.49 (9H, s, C(CH$_3$)$_3$), 1.42 (3H, t, J=5 Hz, CH$_2$CH$_3$).

3-(Aminomethyl)benzoyl-D/L-2-ethylthiazol-4-ylglycine 3-ethoxycarbonyl-4,5,6,7-tetrahydrobenzo[b]thiophene-2-amide trifluoroacetate salt $^1$H NMR (d$_3$ acetonitrile): 8.05 (1H, s, Ar), 7.90 (1H, d, J=15 Hz, Ar), 7.60 (1H, d, J=15 Hz, Ar), 7.45 (1H, m, Ar), 7.35 (1H, s, Ar), 6.00 (1H, m, CHNH), 4.20 (2H, q, J=8 Hz, CH$_2$CH$_3$), 4.10 (2H, s, CH$_2$NH$_2$), 2.95 (2H, q, J=8 Hz, CH$_2$CH$_3$), 2.70 (2H, s, benzo[b]thiophenyl CH$_2$), 2.50 (2H, s, benzo[b]thiophenyl CH$_2$), 1.80 (4H, s, benzo[b]thiophenyl, 2×CH$_2$), 1.30 (3H, t, J=8 Hz, CH$_3$), 1.15 (3H, t, J=8 Hz, CH$_3$) Hplc (LUNA 2, Gradient 1): rt=5.17 minutes LC/MS (LUNA 2 Gradient 4): rt=2.69 minutes, 527 (MH)$^+$

EXAMPLE 34

3-(Aminomethyl)benzoyl-D/L-2-ethylthiazol-4-ylglycine 3-cyano-4,5,6,7-tetrahydrobenzo[b]thiophene-2-amide trifluoroacetate salt Synthesised as described for example 12 using N-BOC-D/L-2-ethylthiazol-4-ylglycine (which was prepared as described in example 33) and 2-amino-3-cyano-4,5,6,7-tetrahydro[b]thiophene (which was prepared using the general procedure below).

Cyclohexanone (10 mmol), malononitrile (10 mmol), acetic acid (8 mmol) and ammonium acetate (2 mmol) were dissolved in benzene (25 mL). The reaction vessel was equipped with a Dean-Stark collector and heated to reflux until water evolution ceased (approx. 6 hours). The mixture was cooled to room temperature, diluted to 100 mL with ethyl acetate, and washed twice with sodium bicarbonate solution (sat. aq., 50 mL) and dried over MgSO$_4$. Volatile components of the reaction mixture were removed under reduced pressure and the crude product was dissolved in ethanol (20 mL). Sulfur (10 mmol) and morpholine (10 mmol) were added and the mixture was heated at reflux for one hour, when TLC indicated complete consumption of starting material. After cooling, the reaction mixture was diluted to 100 mL with ethyl acetate and extracted with hydrochloric acid (1 N, 2×30 mL). The organic portion was then concentrated under reduced pressure to afford crude product which was sufficiently pure to be used without further purification.

3-(Aminomethyl)benzoyl-D/L-2-ethylthiazol-4-ylglycine 3-cyano-4,5,6,7-tetrahydrobenzo[b]thiophene-2-amide trifluoroacetate salt $^1$H NMR (CDCl$_3$): 8.30 (3H, m, Ar), 7.85 (1H, s, Ar) 7.65 (1H, d, J=7 Hz, Ar), 6.15 (1H, d, J=8 Hz, NHCH), 3.90 (2H, s, NH$_2$CH$_2$), 2.95 (2H, q, J=7 Hz, CH$_2$CH$_3$), 2.35 (4H, br s, benzo[b]thiophenyl, 2×CH$_2$), 1.65 (4H, br s, benzo[b]thiophenyl, 2×CH$_2$), 1.25 (3H, t, J=7 Hz, CH$_3$CH$_2$) Hplc (LUNA 2, Gradient 1): rt=4.46 minutes LC/MS (LUNA 2, Gradient 4): rt=2.28 minutes, 480 (MH$^+$)

EXAMPLE 35

3-(Aminomethyl)benzoyl-D/L-2-methylthiazol-4-ylglycine benzothiazol-2-amide

Prepared as described for example 16 but using the protected amino acid N-$^t$butyloxycarbonyl-D/L-2-methylthiazol-4-ylglycine (which was prepared in the same way as that described for N-$^t$butyloxycarbonyl-D/L-2-ethylthiazol-4-ylglycine in example 27 but using thioacetamide instead of thiopropionamide) instead of the protected phenylglycine.

$^1$H NMR (d$_4$ MeOH): 7.84 (2H, m, Ar); 7.7 (1H, d, J=9 Hz, Ar); 7.58 (1H, d, J=9 Hz, Ar); 7.52–7.38 (2H, m, Ar); 7.35 (1H, s, Ar); 7.26 (1H, t, J=6 Hz, Ar); 7.14 (1H, t, J=6 Hz, Ar); 5.95 (1H, s, CH-thiazole); 4.03 (2H, s, CH$_2$NH$_2$); 2.57 (3H, s, CH$_3$). Hplc (Luna 2, Gradient 1): rt=3.56 minutes. LC/MS (Luna 2, Gradient 4): rt=1.68 minutes, 438 (MH)$^+$.

The compounds exemplified hereinabove have been found to be inhibitors of tryptase by the method of Tapparelli et al., (1993) J. Biol. Chem., 268, 4734 to 4741.

The invention claimed is:
1. A tryptase inhibitor compound of formula (I)

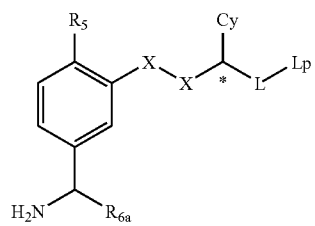

(I)

where:
R$_5$ represents amino, hydroxy, aminomethyl, hydroxymethyl or hydrogen;
R$_{6a}$ represents hydrogen or methyl;
X—X is selected from the group consisting of —CH=CH—, —CONR$_{1a}$—, —NH—CO—, —NR$_{1a}$—CH$_2$—, —CH$_2$—NR$_{1a}$—, —CH$_2$O—, —OCH$_2$—, —COO—, —OC=O— and —CH$_2$CH$_2$—;
R$_{1a}$ represents hydrogen, (1–6C)alkyl or phenyl(1–6C)alkyl;
L is CONR$_{1d}$(CH$_2$)$_m$ in which m is 0 or 1 and R$_{1d}$ is hydrogen, (1–6C)alkyl or phenyl(1–6C)alkyl;
Cy is a saturated or unsaturated, mono or poly cyclic, homo or heterocyclic group optionally substituted by one or more groups R$_{3a}$ — or R$_{3i}$X$_i$—;
each R$_{3a}$ independently is hydrogen, hydroxyl, (1–6C)alkoxy, (1–6C)alkyl, (2–6C)alkenyl, (2–6C)alkynyl, (1–6C)alkanoyl, (1–6C)alkylaminoalkyl, hydroxy (1–6C)alkyl, carboxy, (1–6C)alkoxyalkyl, (1–6C)alkoxycarbonyl, (1–6C) alkylaminocarbonyl, amino (1–6C)alkyl, CONH$_2$, CH$_2$CONH$_2$, aminoacetyl, (1–6C)alkanoylamino, hydroxy(1–6C) alkanoylamino, amino(1–6C)alkanoylamino, (1–6C)alkylamino(1–6C) alkanoylamino, di(1–6C)alkylamino(1–6C)alkanoylamino, (1–6C) alkoxycarbonylamino, amino, halo, cyano, nitro, thiol, (1–6C) alkylthio, (1–6C) alkylsulphonyl, (1–6C) alkylsulphenyl, imidazolyl, hydrazido, (16C)alkylimidazolyl, (1–6C) alkylsulphonamido, (1–6C) alkylaminosulphonyl, aminosulphonyl, (1–6C) haloalkoxy, or (1–6C)haloalkyl;

$X_i$ is a bond, O, $NR_{1p}$, $CH_2$, CO, $CONR_{1p}$, $R_{1p}CO$, $SO_2$, $NR_{1p}SO_2$ or $SO_2NR_{1p}$;

$R_{3i}$ is phenyl or pyridyl;

$R_{1i}$ is as defined for $R_{1a}$

Lp is selected from the group consisting of

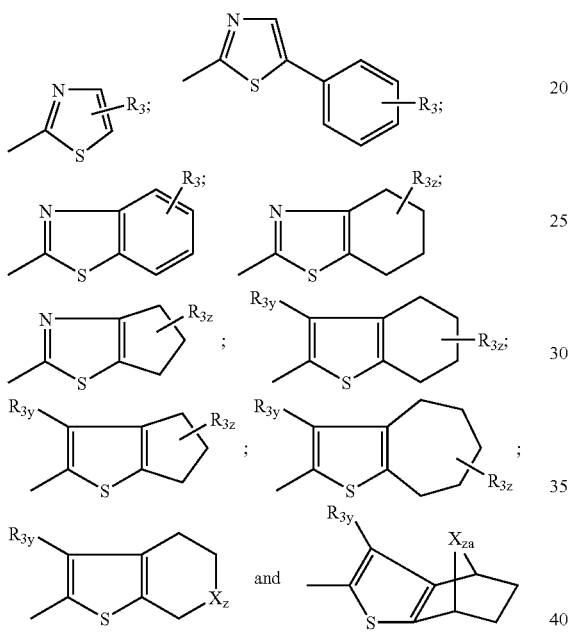

in which $R_3$ is an amino acid residue, N-(1–6C)alkylaminocarbonyl, N,N-di (1–6C)alkylaminocarbonyl, N-(1–6C)alkylaminoalkanoyl, N-(1–6C) alkanoylamino(1–6C)alkanonyl, C-hydroxyamino(1–6C)alkanoyl, hydroxy(2–6C)alkanoylamino(1–6C)alkanoyl, di(1–6C)alkylaminosulfonyl, hydrogen, hydroxyl, (1–6C)alkoxy, (1–6C)alkanoyloxy, (1–6C) alkyl, (2–6C)alkenyl (2–6C)alkynyl, (3–6C)alkenyloxycarbonyl, (1–6C)alkanoyl, amino(1–6C)alkyl, amido ($CONH_2$), amino(1–6C)alkanoyl, aminocarbonyl (1–50) alkanoyl, hydroxy(1–6C) alkyl, carboxy, hydroxy(1–6C)alkanoyl, (1–6C)alkoxy(1–6C)alkanoyl, (1–6C)alkoxy(1–6C)alkyl, (1–6C)alkoxycarbonyl(1–5C)alkyl, (1–6C)alkoxycarbonyl, (1–6C)alkanoylamino, amino, halo, cyano, nitro, thiol, (1–6C) alkylthio, (1–6C)alkylsulfonyl, (1–6C)alkylsulphenyl or hydrazido;

$R_{3y}$ represents $R_3$ or a group of formula $R_k$-G2-$X_a$— in which $G_2$ is absent or represents (1–3C)alkanediyl, $X_a$ is absent or represents O, S, SO, $SO_2$ $NR_L$, CO, OCO, COO, $CONR_L$, $NR_LCO$, $SO_2NR_L$ or $NR_LSO_2$; $R_k$ represents a carbocyclic or heterocyclic group, optionally substituted by $R_3$; and $R_L$ represents hydrogen or (1–6C)alkyl;

$R_{3z}$ is oxo or is as defined for $R_{3y}$, $X_{za}$ is $CR_2$ and $X_z$ is O, S or $NR_z$ in which $R_z$ has a value independently selected from a value for $R_{3y}$;

or a physiologically tolerable salt thereof.

2. A compound as claimed in claim 1, in which:

each $R_{3a}$ independently is hydrogen, hydroxyl, (1–6C) alkoxy, (1–6C) alkyl, (2–6C)alkenyl, (2–6C)alkynyl, (1–6C)alkanoyl, (1–6C) alkylaminoalkyl, hydroxy (1–6C)alkyl, carboxy, (1–6C) alkoxyalkyl, (1–6C) alkoxycarbonyl, (1–6C) alkylaminocarbonyl, amino (1–6C)alkyl, $CONH_2$, $CH_2CONH_2$, aminoacetyl, (1–6C)alkanoylamino, (1–6C) alkoxycarbonylamino, amino, halo, cyano, nitro, thiol, 1–6C) alkylthio, (1–6C) alkylsulphonyl, (1–6C) alkylsulphenyl, imidazolyl, hydrazido, (1–6C)alkylimidazolyl, (1–6C) alkylsulphonamido, (1–6C) alkylaminosulphonyl, aminosulphonyl, (1 . 6C) haloalkoxy, or (1–6C) haloalkyl;

$X_i$ is a bond, O, NH or $CR_2$; and $R_{3i}$ is phenyl optionally substituted by $R_{3a}$; and Lp is selected from the group consisting of $R_3$ is an amino acid residue, N-(1–6C)alkylaminocarbonyl, N,N-di(1–6C)alkylaminocarbonyl, N-(1–6C) alkylaminoalkanoyl, N-(1–6C)alkanoylamino(1–6C) alkanonyl, C-hydroxyamino(1–6C)alkanoyl, hydroxy (2–6C)alkanoylamino(1–6C)alkanoyl, di(1–6C) alkylaminosulfonyl, hydrogen, hydroxyl, (1–6C) alkoxy, (1–6C)alkanoyloxy, (1–6C) alkyl, (2–6C)alkenyl (2–6C)alkynyl, (3–6C)alkenyloxycarbonyl, (1–6C)alkanoyl, amino(1–6C)alkyl, amido ($CONH_2$), amino(1–6C)alkanoyl, aminocarbonyl (1–5C)alkanoyl, hydroxy(1–6C)alkyl, carboxy, hydroxy(1–6C)alkanoyl, (1–6C)alkoxy(1–6C)alkyl, (1–6C)alkoxycarbonyl (1–5C)alkyl, (1–6C)alkoxycarbonyl, (1–6C)alkanoylamino, amino, halo, cyano, nitro, thiol, (1–6C) alkylthio, (1–6C)alkylsulfonyl, (1–6C)alkylsulphenyl or hydrazido; and $R_{3y}$ represents $R_3$ or a group of formula $R_k$-G2-$X_a$— in which $G_2$ represents a bond or (1–3C)alkanediyl, $X_a$ represents a bond, CO, OCO, COO or NHCO, and $R_k$ represents a carbocyclic or heterocyclic group, optionally substituted by $R_3$.

3. A compound as claimed in claim 1, in which $R_5$ is amino or hydrogen.

4. A compound as claimed in claim 3, in which $R_5$ is hydrogen.

5. A compound as claimed in claim 4, in which $R_6a$ is hydrogen.

6. A compound as claimed in claim 1, in which X—X is CONH.

7. A compound as claimed in claim 1, in which the alpha carbon atom (*) has the conformation that would result from construction from a D-α-aminoacid $NH_2$—CH(Cy)-COOH where the $NH_2$ represents part of X—X.

8. A compound as claimed in claim 1, in which Cy represents cycloalkyl, piperidinyl, phenyl, 3,4-methylenedioxyphenyl, furyl, thienyl, imidazolyl, oxazolyl, thiazolyl, pyridyl, pyrimidinyl, pyrazinyl, naphthyl, indolyl, indanyl, 3,4-dihydrobenzofuryl, benzofuryl or benzo[b]thienyl group, optionally substituted by $R_{3a}$ or $R_{3i}X_i$.

9. A compound as claimed in claim 8, in which Cy represents cyclohexyl, piperidin-4-yl, phenyl, 3,4-methylenedioxy-phenyl, fur-2-yl, thien-2yl, thien-3-yl, imidazol-4yl, oxazol-4yl, oxazol-5yl, thiazol-4yl, thiazol-5-yl, pyrid-2-yl, pyrid-3-yl, pyrid-4-yl, pyrimidin-2-yl, pyrimidin-4yl, pyrimidin-5-yl, pyrazin-2-yl, pyrazin-3-yl, naphth-1-yl, naphth-2-yl, indol-5-yl, indan-5-yl, 3,4-dihydrobenzofur-5-yl, benzofur-2-yl or benzo[b]thien-2-yl, optionally substituted by $R_{3a}$ or $R_{3i}X_i$.

10. A compound as claimed in claim 8, in which $R_{3a}$ is hydrogen; hydroxyl; methoxy; ethoxy; isopropoxy; methyl; ethyl; isopropyl; acetyl; propanoyl; isopropanoyl; methylaminomethyl; dimethylaminomethyl; hydroxymethyl; carboxy; methoxymethyl; methoxycarbonyl; ethoxycarbonyl; methylaminocarbonyl; dimethylaminocarbonyl; aminomethyl; $CONH_2$; $CH_2CONH_2$; aminoacetyl; formylamino; acetylamino; hydroxyacetylamino, dimethylaminoacetylamino, methoxycarbonylamino; ethoxycarbonylamino; t-butoxycarbonylamino; amino; fluoro; chloro; bromo; cyano; nitro; thiol; methylthio; methylsulphonyl; ethylsulphonyl; methylsulphenyl; imidazol-4yl; hydrazido; 2-methylimidazol-4-yl; methylsulphonylamido; ethylsulphonylamido; methylaminosulphonyl; ethylaminosulphonyl; aminosulphonyl; trifluoromethoxy or trifluoromethyl; and $R_{3i}X_i$ is phenyl, phenoxy, phenylamino or benzyl.

11. A compound as claimed in claim 10, in which Cy is selected from cyclohexyl, piperidin-4-yl, 1-acetylpiperidin-4-yl, 1-propanoylpiperidin-4yl, 1-isobutyrylpiperidin-4-yl, l-aminoacetylpiperidin-4-yl, phenyl, 2-aminophenyl, 4-aminophenyl, 3-hydroxyphenyl, 4-methylphenyl, 2,4-dimethylphenyl, 3,6-dimethylphenyl, 4-ethylphenyl, 4-isopropylphenyl, 4-hydroxphenyl, 3-aminomethylphenyl, 4-aminomethylphenyl, 4-($H_2NCO$) phenyl, 4-hydroxymethylphenyl, 3-hydroxymethylphenyl, 2-hydroxymethylphenyl, 4-carboxyphenyl, 4-isopropoxyphenyl, 2-chlorophenyl, 3,4-methylenedioxyphenyl, 4-phenylphenyl, 4-phenoxyphenyl, 5-methylfur-2-yl, imidazol-4yl, 2-methylthiazol-4-yl, 2-aminothiazol-4-yl, 2-formylaminothiazol-4yl, 2aminothiazol-5yl, 2-formylaminothiazol-5-yl, 2-phenylthiazol-4-yl, 4-aminopyrid-3-yl, 6-methylpyrid-2-yl, 3-amino-pyrid-4-yl, naphth-1-yl, naphth-2-yl, benzofur-2-yl, 2-methoxyphenyl, 3-methoxyphenyl, 4-methoxyphenyl, indan-5-yl, 2-methylthioethyl, 3-methylthioethyl, 3-methylsulfinylphenyl, 2-methylsulphonylphenyl, 3-methylsulphonylphenyl, 3-N,N-dimethylaminophenyl, 2,3-dihydrobenzofuran-5-yl, 3-bromophenyl, 3-cyanophenyl, 2-methoxycarbonylphenyl, 2-ethoxycarbonylphenyl, 2-methylphenyl, 2-fluorophenyl, 6-aminopyrid-3-yl, 2-ethylthiazol-4-yl, 2-benzylthiazol-4-yl, 2-methylsulfonamidothiazol-4-yl, 2-chloropyrid-3-yl, 2-hydroxyacetylaminothiazol-4-yl, 2-N,N-dimethylaminoacetyl-aminothiazol-4-yl, 2-trifluoromethoxyphenyl, 2-trifluoromethylphenyl, 3-chloropyrid-2-yl, 3-methylpyrid-2-yl, pyrazin-2-yl, pyrazin-3-yl, pyrimidin-2-yl and pyrimidin-3-yl.

12. A compound as claimed in claim 1, in which Cy is a group of formula

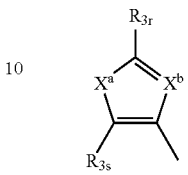

in which one of $X^a$ and $X^b$ is N and the other is NH or S, and each of $R_{3r}$ and $R_{3s}$ is as defined for $R_{3a}$.

13. A compound as claimed in claim 12, in which $X^a$ is S and $X^b$ is N.

14. A compound as claimed in claim 12, in which $R_{3s}$ is hydrogen and $R_{3r}$ is hydrogen, (1–6C)alkyl, amino, (1–6C) alkanoylamino, hydroxy(1–6C)alkanoylamino, N,N-di(1–6C)alkylaminoalkanoylamino, (1–6C)alkylsulfonylamino, phenyl or benzyl.

15. A compound as claimed in claim 1, in which Cy is pyrid-2-yl, pyrimidin-2-yl, pyrimidin-4-yl, pyrazin-2-yl, pyrazin-3-yl or oxazol-4-yl optionally substituted by $R_{3a}$ or $R_{3i}X_i$.

16. A compound as claimed in claim 2, in which Cy is cycloalkyl, piperidinyl, phenyl, 3,4-methylenedioxyphenyl, furyl, thienyl, imidazolyl, thiazolyl, pyridyl, naphthyl, benzofuryl, or benzo[b]thienyl group, optionally substituted by $R_{3a}$ or $R_{3i}X_i$ in which $X_i$ is a bond, O, NH or $CH_2$ and $R_{3i}$ is phenyl optionally substituted by $R_{3a}$ and each $R_{3a}$ independently is hydrogen, hydroxyl, (1–6C) alkoxy, (1–6C) alkyl, (1–6C)alkanoyl, (1–6C) alkylaminoalkyl, hydroxy (1≠6C)alkyl, (1–6C) alkoxyalkyl, (1–6C) alkoxycarbonyl, (1–6C) alkylaminocarbonyl, amino(1–6C)alkyl $CONH_2$, $CH_2CONH_2$, aminoacetyl, (1–6C)alkanoylamino, (1–6C) alkoxycarbonylamino, amino, halo, cyano, nitro, thiol, (1–6C) alkylthio, (1–6C) alkylsulphonyl, (1–6C) alkylsulphenyl, imidazolyl, hydrazido, (1–6C)alkylimidazolyl, (1–6C) alkylsulphonamido, (1–6C) alkylaminosulphonyl, aminosulphonyl, (1–6C) haloalkoxy, or (1–6C) haloalkyl.

17. A compound as claimed in claim 16, in which Cy is cyclohexyl, piperidin-4yl, phenyl, 3,4-methylenedioxyphenyl, fur-2-yl, thien-2-yl, thien-3-yl, imidazol-4-yl, thiazol-4-yl, thiazol-5-yl, pyrid-2-yl, pyrid-3-yl, pyrid-4-yl, naphth-1-yl, naphth-2-yl, benzofur-2-yl, or benzo[b]thien-2-yl group, optionally substituted by $R_{3a}$ or $R_{3i}X_i$.

18. A compound as claimed in claim 16, in which $R_{3a}$ is hydrogen; hydroxyl; methoxy; ethoxy; isopropoxy; methyl; ethyl; isopropyl; acetyl; propanoyl; isopropanoy; methylaminomethyl; dimethylaminomethyl; hydroxymethyl; carboxy; methoxymethyl; methoxycarbonyl; ethoxycarbonyl; methylaminocarbonyl; dimethylaminocarbonyl; aminomethyl; $CONH_2$; $CH_2CONH_2$; aminoacetyl; formylamino; acetylamino; methoxycarbonylamino; ethoxycarbonylamino; t-butoxycarbonylamino; amino; fluoro; chloro; cyano; nitro; thiol; methylthio; methylsulphonyl; ethylsulphonyl; methylsulphenyl; imidazol-4yl; hydrazido; 2-methylimidazol-4-yl; methylsulphonylamido; ethylsulphonylamido; methylaminosulphonyl; ethylaminosulphonyl; aminosulphonyl; trifluoromethoxy or trifluoromethyl; and for $R_{3i}X_i$ are phenyl, phenoxy, phenylamino or benzyl.

19. A compound as claimed in claim 18, in which Cy is cyclohexyl, piperidin-4-yl, 1-acetylpiperidin-4-yl, 1-propanoylpiperidin-4-yl, 1-isobutyrylpiperidin-4-yl, 1-aminoacetylpiperidin-4-yl, phenyl, 4-aminophenyl, 3-hydroxyphenyl, 4-methylphenyl, 2,4-dimethylphenyl, 3,6-dimethylphenyl, 4-ethylphenyl, 4-isopropylphenyl, 4-hydroxphenyl, 3-aminomethylphenyl, 4-aminomethylphenyl, 4-($H_2NCO$) phenyl, 4-hydroxymethylphenyl, 3-hydroxymethylphenyl, 2-hydroxymethylphenyl, 4-carboxyphenyl, 4-isopropoxyphenyl, 2-chlorophenyl, 3,4-methylenedioxyphenyl, 4-phenylphenyl, 4-phenoxyphenyl, 5-methylfur-2-yl, imidazol-4-yl, 2-methylthiazol-4-yl, 2-aminothiazol-4-yl, 2-formylaminothiazol-4-yl, 2-aminothiazol-5-yl, 2-formylaminothiazol-5-yl, 2-phenylthiazol-4-yl, 4-aminopyrid-3-yl, 6-methylpyrid-2-yl, 3-amino-pyrid-4-yl, naphth-1-yl, naphth-2-yl, benzofur-2-yl or 3-methylbenzothien-2-yl.

20. A compound as claimed in claim 1, in which L represents CO, CONH, $CONCH_3$ or $CONHCH_2$.

21. A compound as claimed in claim 20, in which L is CONH or $CONCH_3$.

22. A compound as claimed in claim 1, in which $R_3$ is selected from N-acetylalaninoyl; serinoyl; threoninoyl; aspartoyl; glutamoyl; N,N-dimethylaminocarbonyl; N,N-diethylaminocarbonyl; N-(1,3-dimethyl)butylaminocarbonyl; N-methyl-N-ethylaminocarbonyl; N-methylacetyl; 2-N-acetylaminoacetyl; 2-N-acetylaminopropanoyl; 2-N-(2-methylpropanoyl)aminoacetyl; 2-amino-3-hydroxypropanoyl; 2-amino-3-hydroxybutanoyl; 2-hydroxyacetylaminoacetyl; dimethylaminosulfonyl; hydrogen; hydroxyl; methoxy; acetoxy; methyl; ethyl; propyl; 2propyl; 2,2-dimethylethyl; allyl; propynyl; allyloxycarbonyl; acetyl; propionyl; isobutyryl; aminomethyl; $CONH_2$; aminoacetyl; aminopropionyl; 2-aminopropionyl; aminocarbonylacetyl; hydroxymethyl; 1-hydroxyethyl; carboxy; 2-hydroxyacetyl; 2-hydroxypropanoyl; methoxyacetyl; methoxymethyl; methoxycarbonylmethyl; methoxycarbonyl; ethoxycarbonyl; formylamino; acetylamino; amino; chloro; cyano; nitro; thiol; methylthio; methylsulphonyl; ethylsulfonyl; methylsulphenyl; and hydrazido.

23. A compound as claimed in claim 2, in which $R_3$ is selected from N-acetylalaninoyl; serinoyl; threoninoyl; aspartoyl; glutamoyl; N-(1,3-dimethyl)butylamino-carbonyl; N-methyl-N-ethylaminocarbonyl; N-methylacetyl; 2-N-acetylaminoacetyl; 2-N-acetylaminopropanoyl; 2-N-(2-methylpropanoyl)aminoacetyl; 2-amino-3-hydroxypropanoyl; 2-amino-3-hydroxybutanoyl; 2-hydroxyacetylaminoacetyl; dimethylaminosulfonyl; hydrogen; hydroxyl; methoxy; acetoxy; methyl; ethyl; propyl; 2-propyl; 2,2-dimethylethyl; allyl; propynyl; allyloxycarbonyl; acetyl; propionyl; isobutyryl; aminomethyl; $CONH_2$; aminoacetyl; aminopropionyl; 2-aminopropionyl; aminocarbonylacetyl; hydroxymethyl; 1-hydroxyethyl; carboxy; 2-hydroxyacetyl; 2-hydroxypropanoyl; methoxymethyl; methoxycarbonylmethyl; methoxycarbonyl; ethoxycarbonyl; formylamino; acetylamino; amino; chloro; cyano; nitro; thiol; methylthio; methylsulphonyl; ethylsulfonyl; methylsulphenyl; and hydrazido.

24. A compound as claimed in claim 1, in which L represents $CONR_{1d}$ and Lp represents

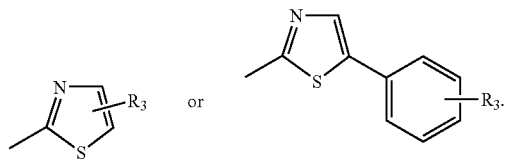

25. A compound as claimed in claim 24, in which each $R_3$ is selected independently from hydrogen, amino, hydroxy, (1–6C)alkyl, (1–6C)alkanoyl, (1–6C)alkanoyloxy, (1–5C)alkoxycarbonyl(1–6C)alkyl, amino(1–6C)alkyl and cyano.

26. A compound as claimed in claim 1, in which L represents $CONR_{1d}$ and Lp represents

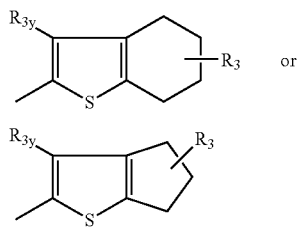

in which $R_{3y}$ represents $R_3$ or a group of formula

in which $G_2$ represents a bond or (1–3C)alkanediyl, $X_a$ represents a bond, CO, OCO, COO or NHCO, and $R_k$ represents a carbocyclic or heterocyclic group, optionally substituted by $R_3$.

27. A compound as claimed in claim 26, in which Lp is selected from the group consisting of

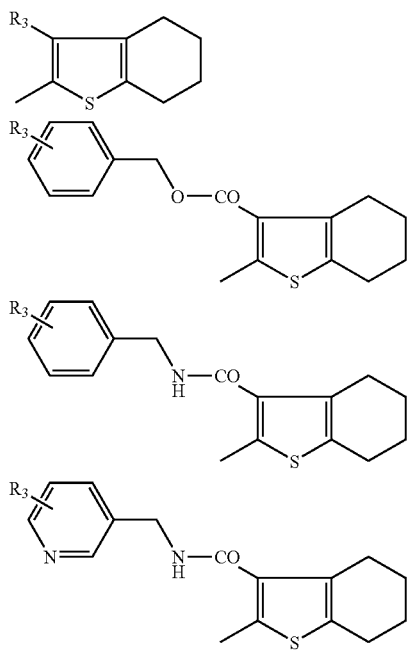

-continued

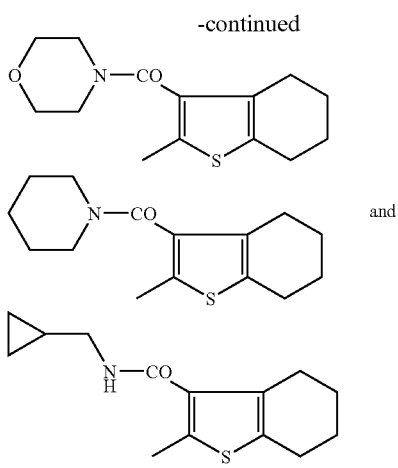

in which (i) when $R_3$ is present as a substituent at the 3-position of a 4,5,6,7tetrahydrobenzothiophene group, it represents a carboxy group; a (1–6C)alkoxycarbonyl group; or a (1–6C)alkylaminocarbonyl group; and (ii) when $R_3$ is present as a substituent on a phenyl or pyridyl group, it is a hydrogen atom.

28. A compound as claimed in claim 1, in which L represents $CONR_{1d}$ and Lp represents

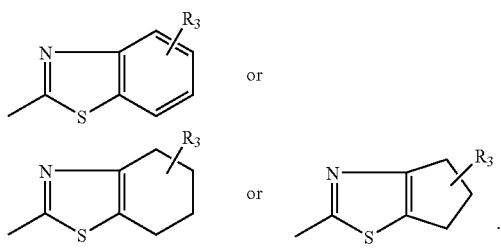

29. A compound as claimed in claim 28, in which the heterocyclic group is substituted by one or two $R_3$ groups.

30. A compound as claimed in claim 29, in which each $R_3$ group is selected from the group consisting of hydrogen, halogen, (1–6C)alkyl and (1–6C)alkoxy.

31. A compound as claimed in claim 1, in which L represents $CONR_{1d}$ and Lp represents

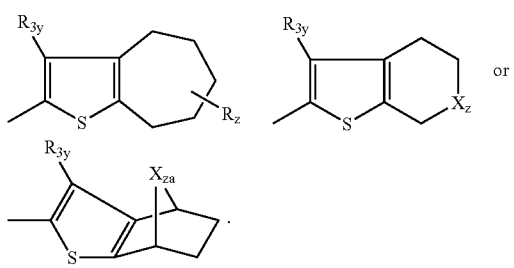

32. A compound as claimed in claim 31, in $R_{3y}$ is (1–6C)alkoxycarbonyl, N,N-dialkylaminocarbonyl or cyano; $R_{3z}$ is hydrogen; $X_z$ is O, S or $NR_z$, $R_z$ is hydrogen, (1–6C) alkanoyl, amino(1–6C)alkanoyl, (1–6C)alkoxy (1–6C)alkanoyl or benzyloxycarbonyl; and $X_{za}$ is $CR_2$.

33. A compound as claimed in claim 32, in which Lp is 3-ethoxycarbonyltetrahydro-4H-cyclohepta(b)thien-2-yl, 3-ethoxycarbonyl-4,5-dihydro-5H-thieno[2,3-c]pyranyl, 3-ethoxycarbonyl-4,5-dihydro-5H-thieno[2,3-c]thiopyranyl, 3-dimethylaminocarbonyl-6benzyloxycarbonyltetrahydrothieno[2,3-b]pyridin-2-yl, 3-dimethylaminocarbonyl-tetrahydrothieno[2,3-b]pyridin-2-yl, 3-dimethylaminocarbonyl-6acetyltetrahydro-thieno[2,3-b]pyridin-2-yl, 3-dimethylaminocarbonyl-6-aminoacetyltetrahydrothieno-[2,3-b]pyridin-2-yl, 3-dimethylaminocarbonyl-6methoxyacetyltetrahydrothieno[2,3-b]pyridin-2-yl or 3-ethoxycarbonyl-tetrahydro-4,7-methanobenzo(b)thophen-2-yl.

34. A compound as claimed in claim 1, in which L is CONH and Lp is

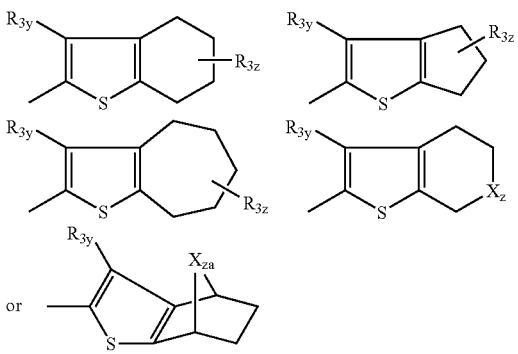

in which $R_{3y}$ is selected from N,N-di-(1–6C)alkylaminocarbonyl, di(1–6C)alkylaminosulfonyl, (3–6C)alkenyloxycarbonyl, (1–6C)alkanoyl, hydroxy(1–6C)alkanoyl, (1–6C) alkoxy(1–6C)alkanoyl, (1–6C)alkoxycarbonyl, (1–6C) alkylsulfonyl, (1–6C)alkylsulphenyl, and $R_k$-$G_2$-$X_a$ in which either $X_a$ is CO, OCO $NR_LCO$, where $R_L$ is (1–6C) alkyl, $SO_2$ or $NR_LSO_2$ and $R_K$ and $G_2$ are as defined previously, or $X_a$ and $G_2$ are both absent and $R_k$ is pyrid-2-yl, thiazol-2-yl, thiazol-4-yl, pyrazin-2-yl, pyrazin-3-yl, pyrimidin-2-yl or pyrimidin-4-yl.

35. A compound as claimed in claim 1 in which the saturated or unsaturated, mono or polycyclic, homo or heterocylic group represented by Cy consists of 5 to 10 ring atoms.

36. 3-(Aminomethyl)benzoyl-D/L-2ethylthiazol-4-ylglycine3-cyano-4,5,6,7-tetrahydrobenzo[b]thiophene-2amide or a physiologically tolerable salt thereof.

37. A compound of formula (IX)

$$Z_2\text{-CH(Cy)-L-Lp} \quad (IX)$$

wherein

Cy and L are as defined in claim 1, Lp is selected from the group consisting of

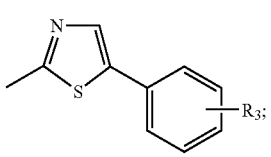

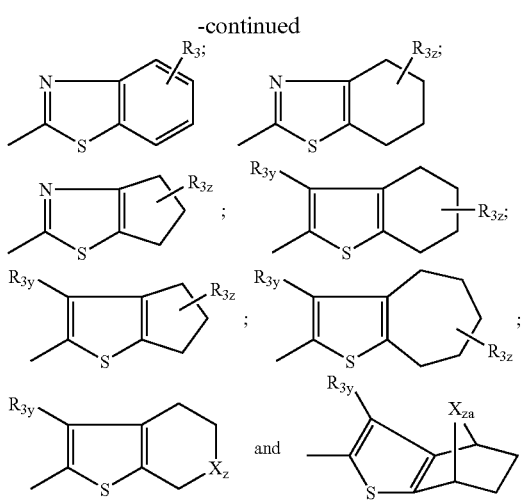

in which:

$R_3$ is an amino acid residue, N-(1–6C)alkylaminocarbonyl, N,N-di(1–6C)alkylaminocarbonyl, N-(1–6C)alkylaminoalkanoyl, N-(1–6C)alkanoylamino(1–6C)alkanoyl, C-hydroxyamino(1–6C)alkanoyl, hydroxy(2–6C)alkanoylamino(1–6C)alkanoyl, di(1–6C)alkylaminosulfonyl, hydrogen, hydroxyl, (1–6C) alkoxy, (1–6C)alkanoyloxy, (1–6C) alkyl, (2–6C)alkenyl (2–6C)alkynyl, (3–6C)alkenyloxycarbonyl, (1–6C)alkanoyl, amino(1–6C)alkyl, amido ($CONH_2$), amino(1–6C)alkanoyl, aminocarbonyl (1–5C)alkanoyl, hydroxy(1–6C)alkyl, carboxy, hydroxy(1–6C)alkanoyl, (1–6C)alkoxy(1–6C)alkanoyl, (1–6C)alkoxy(1–6C)alkyl, (1–6C)alkoxycarbonyl(1–5C)alkyl, (1–6C)alkoxycarbonyl, (1–6C) alkanoylamino, amino, halo, cyano, nitro, thiol, (1–6C) alkylthio, (1–6C)alkylsulfonyl, (1–6C)alkylsulphenyl or hydrazido;

$R_{3y}$ represents $R_3$ or a group of formula $R_k$-G2-$X_a$— in which $G_2$ is absent or represents (1–3C)alkanediyl, $X_a$ is absent or represents O, S, SO, $SO_2$ $NR_L$, CO, OCO, COO, $CONR_L$, $NR_LCO$, $SO_2NR_L$ or $NR_LSO2$; $R_k$ represents a carbocyclic or heterocyclic group, optionally substituted by $R_3$; and $R_L$ represents hydrogen or (1–6C)alkyl; and $R_{3z}$ is oxo or is as defined for $R_{3y}$, $X_{za}$ is $CR_2$ and $X_z$ is O, S or $NR_z$ in which $R_z$ has a value independently selected from a value for $R_{3y}$; and $Z_2$ is $H_2N$ or a salt thereof.

38. A pharmaceutical composition, which comprises a compound as claimed in claim 1 together with at least one pharmaceutically acceptable carrier or excipient.

39. A method of treatment of the human or non-human animal body to combat a condition responsive to a tryptase inhibitor, wherein said condition is selected from the group consisting of asthma, allergic rhinitis, eczema, psoriasis, atopic dermatitis, urticaria, rheumatoid arthritis, conjunctivitis, inflammatory bowel disease, neurogenic inflammation and atherosclerosis, which comprises administering an effective amount of a compound as claimed in claim 1.

40. A method as claimed in claim 39, in which the human or non-human animal body is a human body.

41. A method as claimed in claim 39, in which the condition responsive to a tryptase inhibitor is asthma.

* * * * *